US011096963B2

(12) United States Patent
Corash et al.

(10) Patent No.: US 11,096,963 B2
(45) Date of Patent: Aug. 24, 2021

(54) CRYOPRECIPITATE COMPOSITIONS AND METHODS OF PREPARATION THEREOF

(71) Applicant: Cerus Corporation, Concord, CA (US)

(72) Inventors: Laurence Corash, San Francisco, CA (US); Elan Weiner, Vernon Hills, IL (US); Melody Holtan, Martinez, CA (US); Richard Benjamin, Potomac, MD (US)

(73) Assignee: Cerus Corporation, Concord, CA (US)

( * ) Notice: Subject to any disclaimer, the term of this patent is extended or adjusted under 35 U.S.C. 154(b) by 234 days.

(21) Appl. No.: 15/192,900

(22) Filed: Jun. 24, 2016

(65) Prior Publication Data

US 2017/0027986 A1    Feb. 2, 2017

Related U.S. Application Data

(60) Provisional application No. 62/185,519, filed on Jun. 26, 2015, provisional application No. 62/245,927, filed on Oct. 23, 2015.

(51) Int. Cl.

| | |
|---|---|
| *A61K 35/16* | (2015.01) |
| *A61K 38/36* | (2006.01) |
| *A61K 38/37* | (2006.01) |
| *A61K 35/12* | (2015.01) |
| *A61L 2/00* | (2006.01) |
| *A61M 1/02* | (2006.01) |
| *A61K 41/17* | (2020.01) |
| *A61J 1/18* | (2006.01) |
| *A61K 9/00* | (2006.01) |
| *A61M 1/36* | (2006.01) |
| *A61L 2/07* | (2006.01) |
| *A61L 2/08* | (2006.01) |

(52) U.S. Cl.
CPC ............... *A61K 35/16* (2013.01); *A61J 1/18* (2013.01); *A61K 9/0019* (2013.01); *A61K 38/363* (2013.01); *A61K 38/37* (2013.01); *A61K 41/17* (2020.01); *A61L 2/0047* (2013.01); *A61M 1/0272* (2013.01); *A61M 1/0281* (2013.01); *A61K 2035/124* (2013.01); *A61L 2/07* (2013.01); *A61L 2/081* (2013.01); *A61L 2/087* (2013.01); *A61L 2202/181* (2013.01); *A61L 2202/22* (2013.01); *A61L 2202/23* (2013.01); *A61M 1/3683* (2014.02)

(58) Field of Classification Search
None
See application file for complete search history.

(56) References Cited

U.S. PATENT DOCUMENTS

| | | |
|---|---|---|
| 5,167,656 A | 12/1992 | Lynn |
| 5,288,605 A | 2/1994 | Lin et al. |
| 5,399,719 A | 3/1995 | Wollowitz et al. |
| 5,405,343 A | 4/1995 | Mohr |
| 5,459,030 A | 10/1995 | Lin et al. |
| 5,482,828 A | 1/1996 | Lin et al. |
| 5,556,993 A | 9/1996 | Wollowitz et al. |
| 5,559,250 A | 9/1996 | Cook |
| 5,578,736 A | 11/1996 | Wollowitz et al. |
| 5,585,503 A | 12/1996 | Wollowitz et al. |
| 5,589,462 A * | 12/1996 | Patat ............... A61K 38/1858 424/484 |
| 5,593,823 A | 1/1997 | Wollowitz et al. |
| 5,618,662 A | 4/1997 | Lin et al. |
| 5,625,079 A | 4/1997 | Wollowitz et al. |
| 5,654,443 A | 8/1997 | Wollowitz et al. |
| 5,691,132 A | 11/1997 | Wollowitz et al. |
| 5,712,085 A | 1/1998 | Wollowitz et al. |
| 5,871,900 A | 2/1999 | Wollowitz et al. |
| 5,908,742 A | 6/1999 | Lin et al. |
| 5,965,349 A | 10/1999 | Lin et al. |
| 5,972,593 A | 10/1999 | Wollowitz et al. |
| 6,004,741 A | 12/1999 | Wollowitz et al. |
| 6,004,742 A | 12/1999 | Wollowitz et al. |
| 6,017,691 A | 1/2000 | Wollowitz et al. |
| 6,093,725 A | 7/2000 | Cook et al. |
| 6,099,734 A | 8/2000 | McIarty |
| 6,133,460 A | 10/2000 | Wollowitz et al. |
| 6,143,490 A | 11/2000 | Cook et al. |
| 6,171,777 B1 | 1/2001 | Cook |
| 6,177,441 B1 | 1/2001 | Cook et al. |
| 6,194,139 B1 | 2/2001 | Wollowitz et al. |
| 6,218,100 B1 | 4/2001 | Wollowitz et al. |
| 6,251,580 B1 | 6/2001 | Lin |
| 6,270,952 B1 | 8/2001 | Cook et al. |
| 6,281,225 B1 | 8/2001 | Hearst et al. |
| 6,364,864 B1 | 4/2002 | Mohiuddin |
| 6,410,219 B1 | 6/2002 | Cook et al. |
| 6,420,570 B1 | 7/2002 | Wollowitz |
| 6,433,343 B1 | 8/2002 | Cimino et al. |
| 6,455,286 B1 | 9/2002 | Wollowitz |
| 6,469,052 B2 | 10/2002 | Wollowitz et al. |

(Continued)

FOREIGN PATENT DOCUMENTS

| | | |
|---|---|---|
| GB | 1516698 A | 7/1978 |
| WO | WO-93/00005 A1 | 1/1993 |

(Continued)

OTHER PUBLICATIONS

Utmb Health Blood Transfusion Services. "Plasma". Retrieved on Mar. 15, 2019 from internet URL: https://www.utmb.edu/bloodbank/blood-bank-transfusion-services/component-therapy/plasma (Year: 2019).*

(Continued)

*Primary Examiner* — Allison M Fox
(74) *Attorney, Agent, or Firm* — Morrison & Foerster LLP

(57) ABSTRACT

Provided herein are compositions and kits including a pathogen-inactivated cryoprecipitate suitable for infusion into a subject at least 1 day after thawing. The methods are useful in the efficient preparation of cryoprecipitates with desirable characteristics, including pathogen-inactivated cryoprecipitates that are suitable for infusion into a subject at least 1 day after thawing.

22 Claims, 12 Drawing Sheets

(56) References Cited

U.S. PATENT DOCUMENTS

| | | |
|---|---|---|
| 6,503,699 B1 | 1/2003 | Wollowitz et al. |
| 6,514,987 B1 | 2/2003 | Cook et al. |
| 6,544,727 B1 | 4/2003 | Hei |
| 6,548,242 B2 | 4/2003 | Horowitz et al. |
| 6,565,802 B1 | 5/2003 | Hanley |
| 6,586,749 B2 | 7/2003 | Cimino |
| 6,686,480 B2 | 2/2004 | Wollowitz et al. |
| 6,709,810 B2 | 3/2004 | Cook et al. |
| 6,936,413 B1 | 8/2005 | Bischof |
| 6,949,753 B2 | 9/2005 | Cimino |
| 6,951,713 B2 | 10/2005 | Hei et al. |
| 7,025,877 B1 | 4/2006 | Gheldere et al. |
| 7,037,642 B2 | 5/2006 | Hei |
| 7,068,361 B2 | 6/2006 | Cimino |
| 7,105,093 B2 | 9/2006 | De Gheldere et al. |
| 7,264,608 B2 | 9/2007 | Bischof |
| 7,293,985 B2 | 11/2007 | Cook et al. |
| 7,425,304 B2 | 9/2008 | De Gheldere et al. |
| 7,445,756 B2 | 11/2008 | Moore |
| 7,534,348 B2 | 5/2009 | Reitz |
| 7,611,831 B2 | 11/2009 | Hei |
| 7,655,392 B2 | 2/2010 | Stassinopoulos |
| 8,296,071 B2 | 10/2012 | Edrich et al. |
| 8,439,889 B2 | 5/2013 | Sano |
| 8,900,805 B2 | 12/2014 | Mufti et al. |
| 9,259,525 B2 | 2/2016 | Hei et al. |
| 9,713,627 B2 | 7/2017 | Mufti et al. |
| 10,357,516 B2 | 7/2019 | Mufti |
| 2001/0009756 A1 | 7/2001 | Hei et al. |
| 2001/0018179 A1 | 8/2001 | Hei et al. |
| 2002/0006393 A1 | 1/2002 | Wollowitz |
| 2002/0028432 A1 | 3/2002 | Cook |
| 2002/0042043 A1 | 4/2002 | Stassinopoulos |
| 2002/0115585 A1 | 8/2002 | Hei |
| 2002/0192632 A1 | 12/2002 | Hei et al. |
| 2003/0062483 A1 | 4/2003 | Cimino |
| 2003/0105339 A1 | 6/2003 | Wollowitz |
| 2003/0113704 A1 | 6/2003 | Stassinopoulos et al. |
| 2003/0207247 A1 | 11/2003 | Stassinopoulos et al. |
| 2004/0029897 A1 | 2/2004 | Cook et al. |
| 2004/0180321 A1 | 9/2004 | Cook et al. |
| 2004/0185544 A9 | 9/2004 | Hei |
| 2004/0185553 A9 | 9/2004 | Hei |
| 2004/0197343 A1 | 10/2004 | Dubensky et al. |
| 2004/0228877 A1 | 11/2004 | Dubensky et al. |
| 2005/0142542 A1 | 6/2005 | Hei |
| 2005/0175625 A1 | 8/2005 | Jaffee et al. |
| 2005/0202395 A1 | 9/2005 | Edrich et al. |
| 2005/0249748 A1 | 11/2005 | Dubensky et al. |
| 2005/0281783 A1 | 12/2005 | Kinch et al. |
| 2006/0009399 A1 | 1/2006 | Davis |
| 2006/0115466 A1 | 6/2006 | Stassinopoulos |
| 2007/0031457 A1 | 2/2007 | Dubensky et al. |
| 2007/0190029 A1 | 8/2007 | Pardoll et al. |
| 2007/0190063 A1 | 8/2007 | Bahjat et al. |
| 2007/0207170 A1 | 9/2007 | Dubensky et al. |
| 2007/0207171 A1 | 9/2007 | Dubensky et al. |
| 2010/0133160 A1 | 6/2010 | Hei et al. |
| 2011/0033554 A1 | 2/2011 | Burnouf |
| 2011/0286987 A1 | 11/2011 | Mufti |
| 2013/0143198 A1 | 6/2013 | Sailliol |
| 2015/0157665 A1 | 6/2015 | Mufti et al. |
| 2016/0354533 A1 | 12/2016 | Hei et al. |
| 2017/0202882 A1 | 7/2017 | Vermeij |
| 2017/0304363 A1 | 10/2017 | Corash |
| 2018/0008639 A1 | 1/2018 | Mufti et al. |
| 2018/0185484 A1 | 7/2018 | Greenman et al. |
| 2018/0289873 A1 | 10/2018 | David et al. |
| 2019/0085289 A1 | 3/2019 | Greenman |
| 2019/0209718 A1 | 7/2019 | Church |

FOREIGN PATENT DOCUMENTS

| | | | |
|---|---|---|---|
| WO | WO-1993/17553 A1 | 9/1993 | |
| WO | WO-1994/03054 A1 | 2/1994 | |
| WO | WO-1994/27433 A1 | 12/1994 | |
| WO | WO-95/00141 A1 | 1/1995 | |
| WO | WO-1995/12973 A1 | 5/1995 | |
| WO | WO-1995/19705 A1 | 7/1995 | |
| WO | WO-96/08965 A1 | 3/1996 | |
| WO | WO-96/14739 A1 | 5/1996 | |
| WO | WO-1996/14737 A1 | 5/1996 | |
| WO | WO-1996/14740 A1 | 5/1996 | |
| WO | WO-96/39815 A1 | 12/1996 | |
| WO | WO-96/39820 A1 | 12/1996 | |
| WO | WO-96/40857 A1 | 12/1996 | |
| WO | WO-1996/39818 A1 | 12/1996 | |
| WO | WO-1996/40857 A1 | 12/1996 | |
| WO | WO-97/21346 A1 | 6/1997 | |
| WO | WO-98/18908 A1 | 5/1998 | |
| WO | WO-98/30327 A1 | 7/1998 | |
| WO | WO-1998/30545 A1 | 7/1998 | |
| WO | WO-1999/03976 A2 | 1/1999 | |
| WO | WO-1999/03976 A3 | 1/1999 | |
| WO | WO-1999/26476 A1 | 6/1999 | |
| WO | WO-99/34914 A1 | 7/1999 | |
| WO | WO-99/34915 A1 | 7/1999 | |
| WO | WO-1999/34839 A1 | 7/1999 | |
| WO | WO-1999/63981 A2 | 12/1999 | |
| WO | WO-1999/63981 A3 | 12/1999 | |
| WO | WO-2001/91775 A2 | 12/2001 | |
| WO | WO-2001/91775 A3 | 12/2001 | |
| WO | WO-2003/47650 A2 | 6/2003 | |
| WO | WO-2003/47650 A3 | 6/2003 | |
| WO | WO-2003/049784 A2 | 6/2003 | |
| WO | WO-2003/049784 A3 | 6/2003 | |
| WO | WO-2003/61379 A2 | 7/2003 | |
| WO | WO-2003/61379 A3 | 7/2003 | |
| WO | WO-2003/65787 A2 | 8/2003 | |
| WO | WO-2003/65787 A3 | 8/2003 | |
| WO | WO-2003/078023 A1 | 9/2003 | |
| WO | WO-2003/090794 A1 | 11/2003 | |
| WO | WO-2004/049914 A2 | 6/2004 | |
| WO | WO-2004/049914 A3 | 6/2004 | |
| WO | WO-2004/050029 A2 | 6/2004 | |
| WO | WO-2004/050029 A3 | 6/2004 | |
| WO | WO-2004/050848 A2 | 6/2004 | |
| WO | WO-2004/050848 A3 | 6/2004 | |
| WO | WO-2004/050897 A2 | 6/2004 | |
| WO | WO-2004/050897 A3 | 6/2004 | |
| WO | WO-2004/084936 A2 | 10/2004 | |
| WO | WO-2004/084936 A3 | 10/2004 | |
| WO | WO-2004/110481 A2 | 12/2004 | |
| WO | WO-2004/110481 A3 | 12/2004 | |
| WO | WO-2005/009463 A2 | 2/2005 | |
| WO | WO-2005/009463 A3 | 2/2005 | |
| WO | WO-2005/037233 A2 | 4/2005 | |
| WO | WO-2005/037233 A3 | 4/2005 | |
| WO | WO-2005/067460 A2 | 7/2005 | |
| WO | WO-2005/067460 A3 | 7/2005 | |
| WO | WO-2005/071088 A2 | 8/2005 | |
| WO | WO-2005/071088 A3 | 8/2005 | |
| WO | WO-2005/092372 A2 | 10/2005 | |
| WO | WO-2005/092372 A3 | 10/2005 | |
| WO | WO-2006/050328 A1 | 5/2006 | |
| WO | WO-2007/022511 A2 | 2/2007 | |
| WO | WO-2007/022511 A3 | 2/2007 | |
| WO | WO-2007/022520 A2 | 2/2007 | |
| WO | WO-2007/022520 A3 | 2/2007 | |
| WO | WO-2007/103225 A2 | 9/2007 | |
| WO | WO-2007/103225 A3 | 9/2007 | |
| WO | WO-2007/103261 A2 | 9/2007 | |
| WO | WO-2007/103261 A3 | 9/2007 | |
| WO | WO-2007/117371 A2 | 10/2007 | |
| WO | WO-2007/117371 A3 | 10/2007 | |
| WO | WO-2009/126786 A2 | 10/2009 | |
| WO | WO-2009/126786 A3 | 10/2009 | |
| WO | WO2009118331 A1 | 10/2009 | |
| WO | WO-2012/018484 A2 | 2/2012 | |
| WO | WO-2012/018484 A3 | 2/2012 | |
| WO | WO-2012/071135 A2 | 5/2012 | |
| WO | WO-2012/071135 A3 | 5/2012 | |
| WO | WO-2016/014854 A1 | 1/2016 | |
| WO | WO-2016/057965 A1 | 4/2016 | |

(56) References Cited

FOREIGN PATENT DOCUMENTS

| WO | WO-2016/115535 A1 | 7/2016 |
|---|---|---|
| WO | WO-2017/070619 A1 | 4/2017 |
| WO | WO-2017/120545 A2 | 7/2017 |
| WO | WO-2017/120545 A3 | 7/2017 |
| WO | WO2018119462 A1 | 6/2018 |
| WO | WO-2018/125994 A1 | 7/2018 |
| WO | WO-2018/161020 A1 | 9/2018 |

OTHER PUBLICATIONS

Asselta et al, "The molecular basis of quantitative fibrinogen disorders" Journal of Thrombosis and Haemostasis. 2006, vol. 4, pp. 2115-2129. (Year: 2006).*

Burnouf et al, Transfusion Feb. 2011, 51, pp. 446-447. (Year: 2011).*

Prodouz, K.N. et al., (1992). "Effects of Two Viral Inactivation Methods on Platelets: Laser-UV Radiation and Merocyanine 540-Mediated Photoinactivation," *Blood Cells* 18(1):101-16.

Sofer, G. (Aug. 2002). "Virus Inactivation in the 1990s—and into the 21st Century Part 2, Red Blood Cells and Platelets," *BioPharm* pp. 45-49.

Backholer, L. et al. (2016). "Paired Comparison of Methylene Blue- and Amotosalen-Treated Plasma and Cryoprecipitate," *VoxSanguinis* 10 pages.

Bryant, B. et al. (May 1, 2007). "Pathogen Inactivation: The Definitive Safegaurd for the Blood Supply," pp. 719-733. Retrieved from the internet:URL:http://www.archivesofpathology.org/doi/pdf/10.1043/1543-2165(2007)131[719:PITDSF]2.0.CO;2 [Retrieved on Sep. 22, 2016] p. 724-p. 728.

Burnouf, T. et al. (Nov. 1, 2007). "Preparation and Viral Inactivation of Cryoprecipitate in Blood Banks in Resource-Limited Countries," *ISBT Science Series*, 2(2):121-128.

Cid, J. et al. (Mar. 2013). "Quantitative and Qualitative Analysis of Coagulation Factors in Cryoprecipitate Prepared from Fresh-Frozen Plasma Inactivated with Amotosalen and Ultraviolet A Light," Transfusion, 53(3):600-605.

Dyck, P.J.et al. (Dec. 1994). "A Plasma Exchange Versus Immune Globulin Infusion Trial in Chronic Inflammatory Demyelinating Polyradiculoneuropathy," *Ann. Neurol.* 36(6):838-845.

El-Ekiaby, M. (2010). "Solvent-Detergent Filtered (S/D-F) Fresh Frozen Plasma and Cryoprecipitate Minipools Prepared in a Newly Designed Integral Disposable Processing Bag System," *Transfusion Medicine* 21:48-61.

Ettinger, A. et al. (2012). "Preparation of Cryoprecipitate From Riboflavin and UV Light-Treated Plasma," *Transfusion and Apheresis Science* 46:153-158.

Garwood, M. et al. (Sep. 2003). "The Effect of Methylene Blue Photoinactivation and Methylene Blue Removal on the Quality of Fresh-Frozen Plasma," *Transfusion* 43(9):1238-1247.

Green, I. et al. (Jun. 2016). "The Hemostatic Properties of Thawed Pooled Cryoprecipitate Up to 72 Hours," *Blood Components* 56:1356-1361.

Greenhalgh, D.G. (2007). "Burn Resuscitation," *Journal of Burn Care & Research* 28(4):555-565.

*Guidance for Industry: An Acceptable Circular of Information for the Use of Human Blood and Blood Components U.S. Department of Health and Human Services*, (Aug. 2013), 83 pages.

Hayek, S. et al. (2011). "Burn Resuscitation: Is It Straightforward or a Challenge?," *Annals of Burns and Fire Disasters* XXIV(1):17-21.

Herbrecht, R. et al. (2013). "Comparative Effectiveness and Safety of Pathogen Inactivated (Amotosalen-UVA) and Conventional Plasma for Treatment of Auto-Immmune Thrombotic Thrombocytopenic Purpura (TTP): A 15-Year Retrospective Review," *Blood* 122(21):4820.

Hornsey, V.S. et al. (2009). "Pathogen Reduction of Fresh Plasma Using Riboflavin and Ultraviolet Light: Effects on Plasma Coagulation Proteins," *Transfusion* 49(10):2167-2172.

Inaba, K. (May 2011). "Freeze-Dried Plasma," *J. Trauma* 70(5):S57-S58.

Intercept Blood System, "Platelet and Plasma Synergy: A Single System for Two Components," Cerus Corporation (2006).

Irsch, J. et al. (2015). "Update on Pathogen Inactivation Treatment of Plasma, With the Intercept Blood System: Current Position on Methodological, Clinical and Regulatory Aspect," *Transfusion and Apheresis Science*. 52(2):240-244.

Klein, H.G. et al. (Mar. 1, 2005). "Pathogen Inactivation Technology: Cleaning the Blood Supply," *Journal of Internal Medicine*, 257(3):224-237.

Lozano, M. et al. (Nov. 1, 2013). "Pathogen Inactivation," *Current Opinion in Hematology*, 20(6):540-545.

Mintz, P.D. et al. (2000). "SP71—Preparation of Cryoprecipitate From Photochemically Treated Fresh Frozen Plasma," *Transfusion* 40:63S.

Mintz, P.D. et al. (2004). "Therapeutic Plasma Exchange (TPE) for Thrombotic Thrombocytopenic Purpura (TTP) Using Plasma Prepared With Photochemical Treatment (Intercept Plasma)," *Blood* 104(11):838.

Mintz, P.D. et al. (May 1, 2006). "Photochemically Treated Fresh Frozen Plasma for Transfusion of Patients with Acquired Coagulopathy of Liver Disease," 107(9):3753-3760. Retrieved from the Internet:URL:http://www.bloodjournal.org/content/107/9/3753.full.pdf [retrieved on Sep. 21, 2016]*Discussion*.

Mintz, P.D. et al. (Oct. 2006). "A Randomized, Controlled Phase III Trial of Therapeutic Plasma Exchange With Fresh-Frozen Plasma (FFP) Prepared With Amotosalen and Ultraviolet A Light Compared to Untreated FFP in Thrombotic Thrombocytopenic Purpura," *Transfusion* 46(10):1693-1704.

Mirasol (TerumoBCT)—Webpage. Retrieved from <https://www.terumobct.com/miraso.pdf>, last visited Jun. 18, 2018. 8 pages.

Nascimento, B. et al. (Dec. 1, 2014). "Cryoprecipitate Therapy," 113(6):922-934.

*New and Emerging Health Technology Report: Technologies for the Inactivation/Reduction of Pathogens in Blood Products*, (Jul. 2011) 108 pages.

Octaplas, Octapharma, "Highlights of Prescribing Information," retrieved from <https://www.fda.gov/downloads/biologicsbloodvaccines/.../ucm336161.pdf>, lasted visited Aug. 22, 2018, 8 pages.

Picker, S.M. (Jan. 1, 2013). "Pathogen Reduction Technologies: The Best Solution for Safer Blood?" *Journal of Blood Disorders & Transfusion*, 3(5), 5 pages.

Radosevich, M. et al. (2010, e-pub. Jul. 29, 2009). "Intravenous Immunoglobulin G: Trends in Production Methods, Quality Control and Quality Assurance," *Vox Sanguinis* 98:12-28.

Rummler, S. et al. (2013). "SP57—Efficacy and Safety of Pathogen Reduced Plasma in Plasma Therapy in Germany," Transfusion. 53(supp. 2):77A.

Sailliol, A. et al. (Jan. 2013). "The Evolving Role of Lyophilized Plasma in Remote Damage Control Resuscitation in the French Armed Forces Health Service," *Transfusion* 53(Suppl. 1):65S-71S.

Sheffield, W.P. et al. (2016). "Stability of Coagulation Protein Activities in Single Units of Pools of Cryoprecipitate During Storage At 20-24° C. for Up to 24 H," *VoxSanguinis* 110:12-19.

Solheim, B.G. et al. (Jan. 2000). "Viral safety of Solvent/Detergent-Treated Plasma," *Transfusion* 40(1):84-90.

Spivey, M.A. et al. (1992). "Postfiltration Factor VIII and Fibrinogen Levels in Cryoprecipitate Stored At Room Temperature and At 1 to 6° C.," *Transfusion* 32(4):340-343.

Theraflex (MacoPharma)—Webpage. Retrieved from <https://blood-safety.macopharma.com/category/products/theraflex-mb-plasma-products/product.pdf> lasted visited Jun. 18, 2018, 4 pages.

Ward, D.M. (2011, e-pub. Aug. 31, 2011). "Conventional Apheresis Therapies: A Review," *J. Clin. Apheresis* 26:230-238.

Winters, J.L. (2012). "Plasma Exchange: Concepts, Mechanisms, and An Overview of the American Society for Apheresis Guidelines," *Hematology* 2012:7-12.

Wong, H. et al. (Sep. 22, 2016). "Cryoprecipitate Transfusion: Current Perspectives," *International Journal of Clinical Transfusion Medicine* 4:89-97.

International Preliminary Report on Patentability, dated Apr. 28, 2018, for PCT Application No. PCT/US2016/058318, filed Oct. 21, 2016, 13 pages.

(56) References Cited

OTHER PUBLICATIONS

International Search Report, dated Dec. 20, 2016, for PCT Application No. PCT/US2016/058318, 4 pages.
International Preliminary Report on Patentability dated Dec. 26, 2017, for PCT Application No. PCT/US2016/039428, filed Jun. 24, 2016, 12 pages.
International Search Report dated Dec. 13, 2016, for PCT Application No. PCT/US2016/039428, internationally filed on Jun. 24, 2016, 8 pages.
Written Opinion dated Dec. 13, 2016, for PCT Application No. PCT/US2016/039428, filed on Jun. 24, 2016, 11 pages.
Written Opinion dated Dec. 20, 2016, for PCT Application No. PCT/US2016/058318, filed on Jun. 24, 2016, 12 pages.
U.S. Appl. No. 15/770,186, Corash et al, filed Oct. 21, 2016. (submitted herewith pursuant to the waiver of 37 C.F.R. § 1.98(a)(2)(iii) issued by the Office dated Sep. 21, 2004.).
Circular of Information for the Use of Human Blood and Blood Components (Apr. 2013)., *AABB, American Red Cross, American's Blood Centers, and Armed Services Blood Program*, 42 pages.
Electronic Code of Federal Regulations (2019). Title 21: Food and Drugs, Section 606.122: Circular of Information, retrieved from <https://www.ecfr.gov/cgi-bin/text-idx?SID-36cf34a3930282fa3928d7c7d8de61b0&mc=tr . . . > last visited Jan. 29, 2019.
McQuilten, Z.K. et al. (2017, e-pub. Jun. 27, 2017). "Fibrinogen Concentration and Use of Fibrinogen Supplementation With Cryoprecipitate in Patents With Critical Bleeding Receiving Massive Transfusion: A Bi-National Cohort Study," *British Journal of Haematology* 179:131-141.
Press Release (Oct. 31, 2018). "Cerus Received FDA Breakthrough Device Designation for Pathogen-Reduced Cryoprecipitate," retrieved from <https://www.marketwatch.com/press-release/cerus-receives-fda-breakthrough-device-design . . . > last visited Feb. 8, 2019, 4 pages.
Yazer, M.H. (2018). "Congress Review: Auditing as a Means of Detecting Waste," *ISBT Science Series* 13:29-34.
Singapore Search Report, dated Dec. 12, 2018, for Singapore Patent Application. No. 11201710548R, 5 pages.
Singapore Written Opinion, dated Dec. 12, 2018, for Singapore Patent Application No. 11201710548R, 9 pages.

U.S. Appl. No. 09/238,355, Greenman, W. et al, filed Jan. 27, 1999. (submitted herewith pursuant to the waiver of 37 C.F.R. § 1.98(a)(2)(iii) issued by the Office dated Sep. 21, 2004.).
Anonymous. (Nov. 17, 2005). "Guideline on the Core SPC for Human Albumin Solution (CPMP/PhVWP/BPWG/2231/99 rev. 2)," Committee for Medicinal Products for Human Use (CHMP) pp. 1-10.
Aznar, J.A. et al. (Jan. 1, 2000). "Influence of Methylene Blue Photoinactivation Treatment on Coagulation Factors from Fresh Frozen Plasma, Cryoprecipitates and Cryosupematants," Vox Sanguinis 78:156-160.
European Office Action, dated May 24, 2019, for European Patent Application No. 16738300.9, 5 pages.
O'Shaughnessy, D.F. et al. (May 12, 2004). "Guidelines for the Use of Fresh-Frozen Plasma, Cryoprecipitate and Cryosupematant," British Journal of Haematology 126:11-28.
Yarranton, H. et al. (Sep. 2005). "Coagulation Factor Levels in Cryosupematant Prepared From Plasma Treated With Amotosalen Hydrochloride (S-59) and Ultraviolet A Light," Transfusion 45:1453-1458.
Committee for Medicinal Products for Human Use(CHMP) (Nov. 17, 2005). "Guideline on the Core SPC for 7-12 Human Albumin Solution (CPMP/PhVWP/BPWG/2231/99 rev.2),", 10 pages.
Extended European Search Report, dated Oct. 30, 2019, for European Patent Application No. 16858399.5, 19 pages.
Irsch, J. et al. (2011, e-pub. Jan. 27, 2011). "Pathogen Inactivation of Platelet and Plasma Blood Components for Transfusion Using the Intercept Blood System™," Transfus. Med. Hemother. 38:19-31.
Schlenke, P. et al. (2008). "Photochemical Treatment of Plasma With Amotosalen and UVA Light: Process Validation in Three European Blood Centers," Transfusion 48:697-705, 9 pages.
Singapore Written Opinion, dated Oct. 31, 2019, for Singapore Patent Application No. 11201710548R, 6 pages.
Wiltshire, M. et al. (2013). "Quality of Cryoprecipitate Manufactured From Fresh Frozen Plasma Treated With Methylene Blue or Intercept Pathogen Inactivation Systems," Vox Sanguinis 105(Suppl. 1):157, Abstract P-264, 1 page.
Irsch, J. et al. (Jan. 1, 2010, e-pub. Aug. 30, 2009). "Intercept Plasma: Comparability With Conventional Fresh-Frozen Plasma Based on Coagulation Function—An In Vitro Analysis," Vox Sanguinis 98(1):47-55.

* cited by examiner

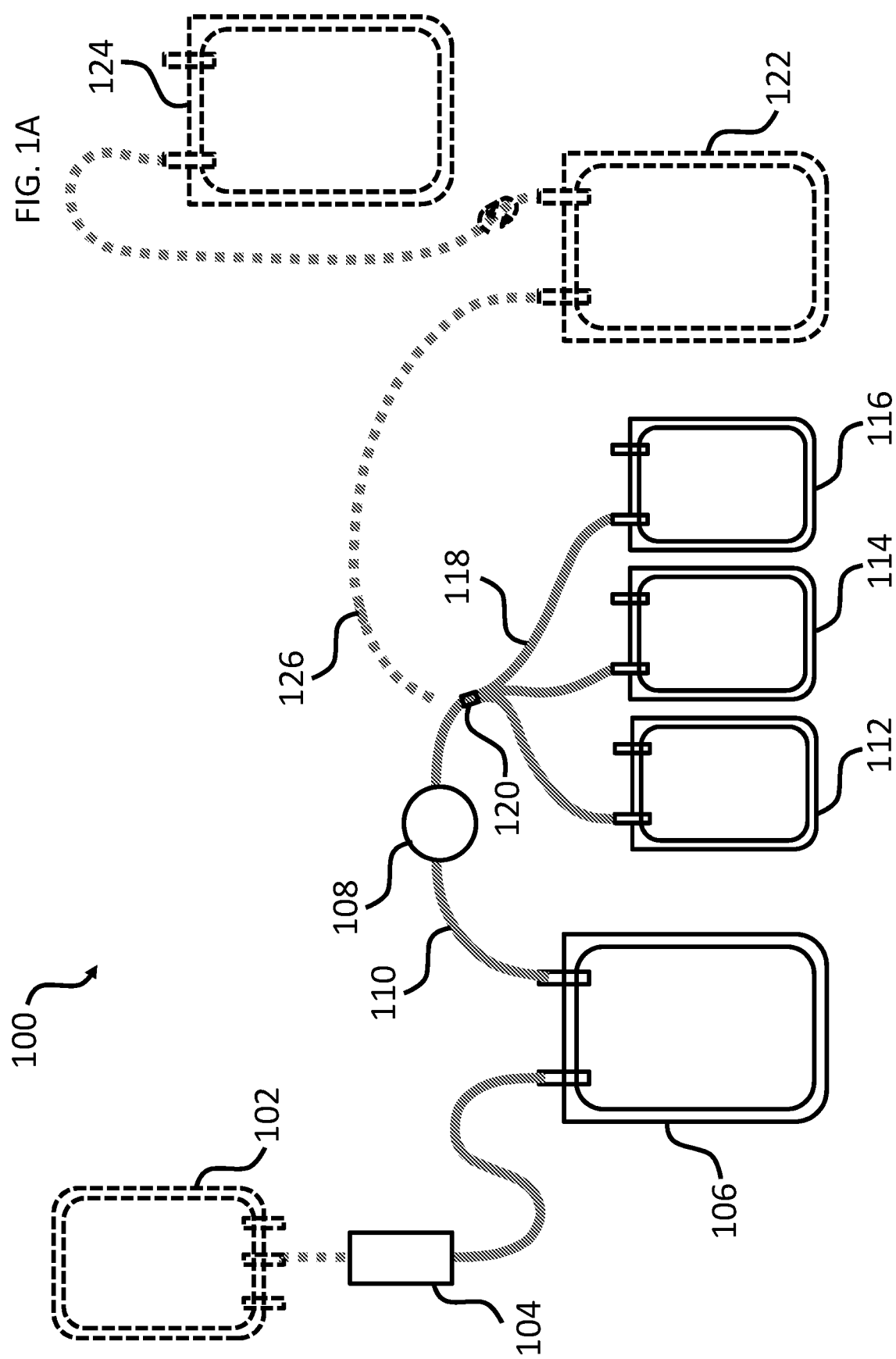

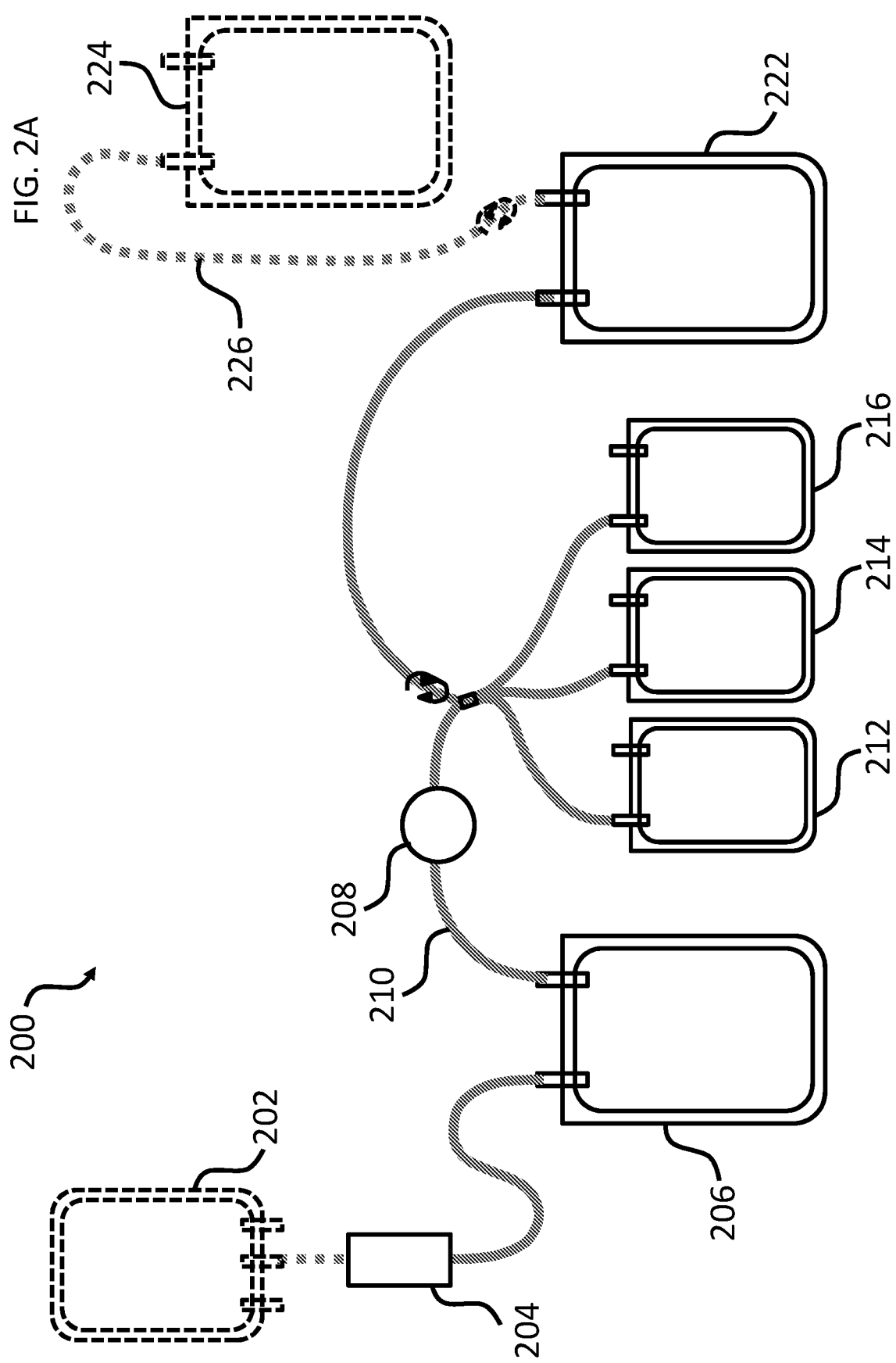

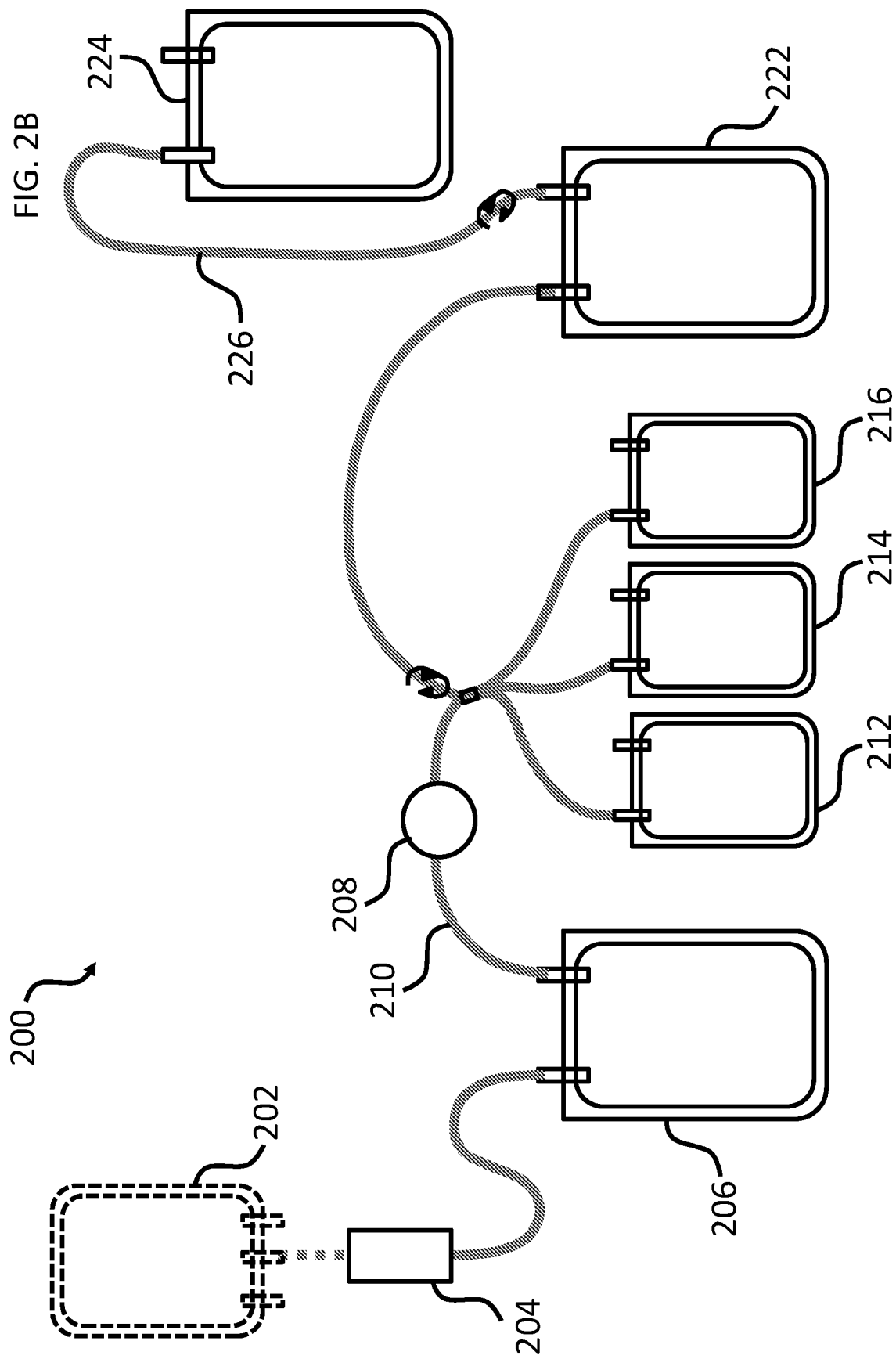

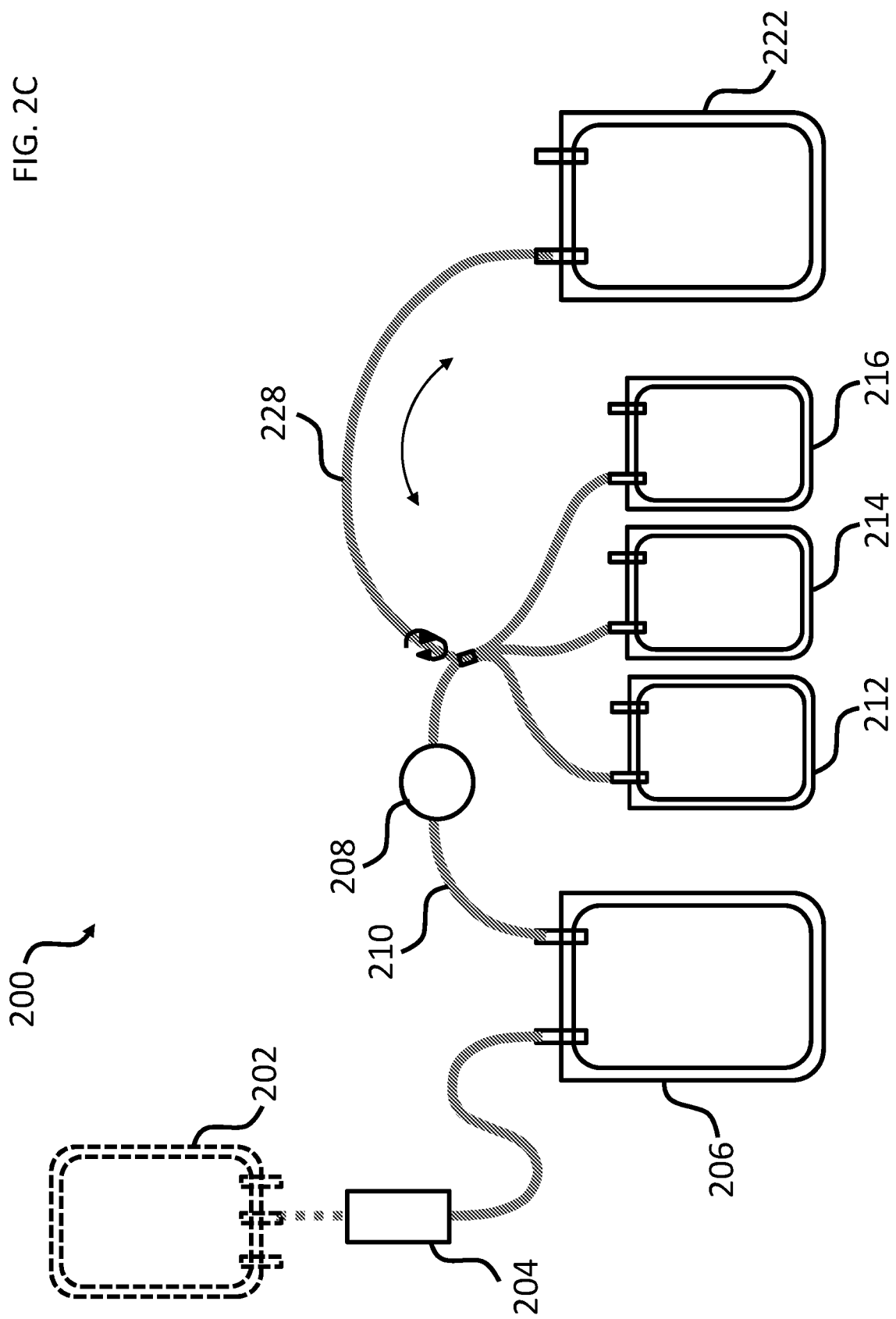

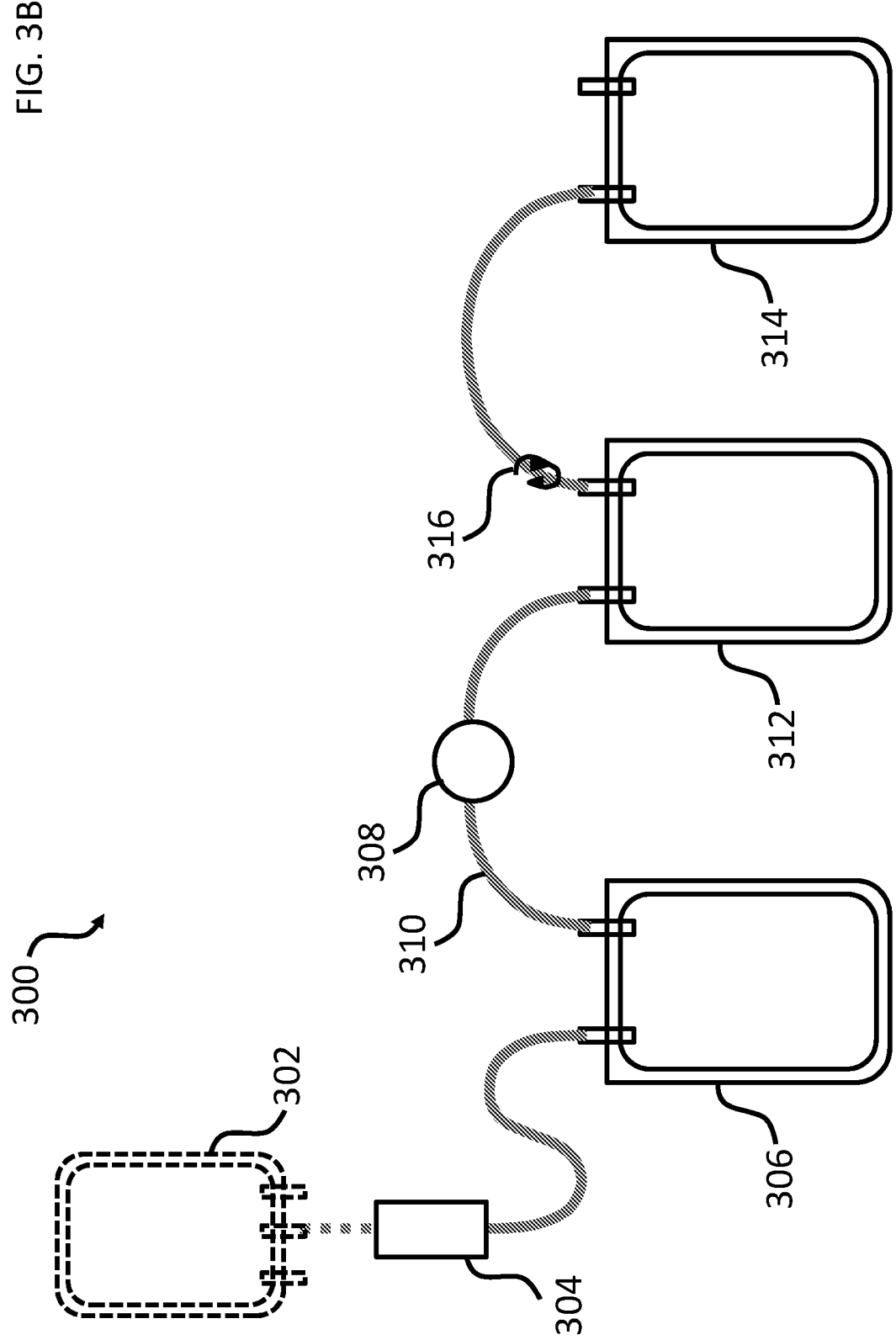

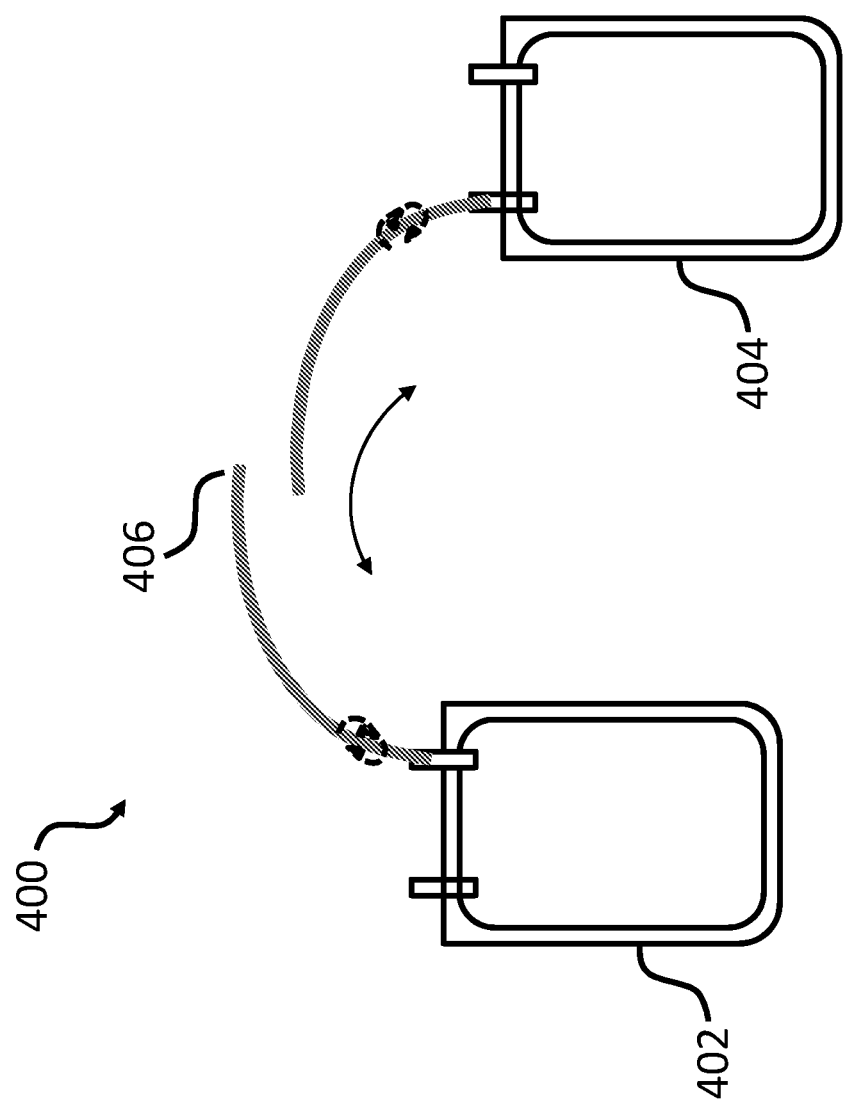

CRYOPRECIPITATE COMPOSITIONS AND METHODS OF PREPARATION THEREOF

CROSS REFERENCE TO RELATED APPLICATIONS

This application claims the priority benefit of U.S. Provisional Application Ser. No. 62/185,519, filed Jun. 26, 2015; and 62/245,927, filed Oct. 23, 2015; each of which is incorporated herein by reference in its entirety.

TECHNICAL FIELD

The methods described herein generally relate to the preparation of cryoprecipitate from plasma. More particularly, the present disclosure relates to improved cryoprecipitate compositions, as well as methods of preparation and kits related thereto, which may be used for infusion into a subject.

BACKGROUND

Blood collection and processing serves a critical role in healthcare worldwide, and millions of units of donated whole blood are collected by blood banks each year. While some whole blood units collected from donors are stored and used for transfusion, most whole blood is instead separated into its clinically therapeutic components of red blood cells, platelets and plasma, for individual storage and use in treating different medical needs and conditions requiring one or more of the particular blood components.

Cryoprecipitate (also known as "cryo") is a blood product comprising a portion of plasma rich in coagulation factors. Cyroprecipitate, also referred to as cryoprecipitated antihaemophilic factor (AHF), cryoprecipitated AHF, is prepared by slow, controlled thawing of frozen plasma (e.g., whole blood-derived fresh frozen plasma, or FFP), for example between 1° and 6° C. (e.g., 4±2° C.), which results in the formation of a white precipitate, and then recovering the precipitate following separation from the liquid plasma portion, also referred to herein as "supernatant," such as by refrigerated centrifugation. The "cryo-poor" remaining plasma, also referred to herein as "cryo-poor plasma" (CPP), "cryoprecipitate-reduced plasma," or "cryosupernatant," is removed from the bag, and the isolated cold-insoluble precipitate is re-suspended in a portion of the plasma left behind and generally re-frozen within 1 hour, and stored frozen until needed for transfusion.

Cryoprecipitate serves as a source of fibrinogen, Factor VIII, Factor XIII, vWF, and fibronectin. This component is used in the control of bleeding associated with fibrinogen deficiency and to treat Factor XIII deficiency when volume considerations preclude the use of frozen plasma and recombinant proteins are not available. It is also indicated as second-line therapy for von Willebrand disease and hemophilia A (Factor VIII deficiency). Coagulation factor preparations other than cryoprecipitate are generally preferred when blood component therapy is needed for management of von Willebrand disease and Factor VIII deficiency. Although many uses of cryoprecipitate products have been replaced by factor concentrates or recombinant factors, cryo is still routinely stocked by many hospital blood banks for use in the replacement of fibrinogen in patients, such as, for example, patients with acquired hypofibrinogenemia and bleeding (e.g., massive hemorrhage). Compatibility testing of blood groups is not strictly necessary for cryoprecipitate; however, transfusion of ABO-compatible cryo is generally preferred when possible.

Cryoprecipitate is often transfused in pools of individual units (e.g., 4-6 unit pool, 5-6 unit pool), instead of as a single product, with a target of increasing a recipient's (e.g., adult recipient) fibrinogen level by, for example, 30-60 mg/dL. Pooling is generally performed after thawing individual units, prior to transfusion. If the label indicates "Pooled Cryoprecipitated AHF," several units of Cryoprecipitated AHF have been pooled. The volume of the pool is generally indicated on the label and, if used, the volume of 0.9% Sodium Chloride, Injection (USP) may be separately listed.

As a measurement of potency (activity) and/or quality for use in transfusion, Cryoprecipitated AHF units should contain designated amounts of Factor VIII and fibrinogen, and generally comprise approximately 5 to 20 mL of plasma. Current US standards require manufacturers to test at least four cryo units each month, and the products must have an average of 150 mg or more of fibrinogen and 80 IU of factor VIII. Some individual products may actually have less than these amounts as long as the average remains above these minimums. Typical values for a unit are substantially higher, and aside from infants it is rare to transfuse just one unit.

Although measurement of Factor VIII is currently required for quality control, cryo is primarily used to maintain fibrinogen levels for proper hemostasis, e.g., in treating disseminated intravascular coagulation (DIC) or high volume hemorrhage. Cryoprecipitate use is generally limited by requirements that it is transfused within 6 hours of thawing or 4 hours of pooling, a time constraint driven by multiple considerations, including for example, the more rapid decrease in Factor VIII activity and the potential for growth of pathogen contaminants, if present. For example, it is known that the half-life for Factor VIII is about 12 hours, as compared to fibrinogen, which has a half-life of about 100-150 hours. The discarding of unused cryoprecipitate that has expired after 4 or 6 hours post-thawing results in product waste and increased costs. Additionally, for indications requiring rapid delivery of cryoprecipitate to the patient (e.g., massive hemorrhage), the time required for thawing and pooling of cryoprecipitate may also be another limitation.

There remains a need for improved methods for preparing cryoprecipitate and improved cryoprecipitate compositions for transfusion and other uses, including for example cryoprecipitate compositions with extended post-thaw expiry, and/or sufficient fibrinogen content that pooling is not required between thawing of the cryo product and administration to a patient. Such improved compositions and methods may provide for greater efficiencies in cryoprecipitate preparation and/or use, such as for example, increased numbers of product units, less wastage, more efficient processes for the provision of required amounts of cryo product to the clinician for use in transfusion, more time between thawing and administration, improved availability and/or product uniformity, and/or access to a larger available donor population.

SUMMARY

The compositions, methods, and kits described herein are useful in providing a cryoprecipitate with desirable characteristics, including, for example, pathogen inactivated cryoprecipitate, and cryoprecipitate suitable for use for a greater duration after thawing.

In one aspect, the present disclosure provides a composition comprising a cryoprecipitate suitable for infusion into a subject at least 1 day after thawing, wherein the cryoprecipitate is pathogen-inactivated. In some embodiments, the composition is suitable for infusion into a subject at least 3 days after thawing. In some embodiments, the composition is suitable for infusion into a subject at least 5 days after thawing. In some embodiments, the composition is suitable for infusion into a subject at least 7 days after thawing. In some embodiments, the composition comprises less than 80 IU of factor VIII per unit of cryoprecipitate. In some embodiments, the composition comprises less than 50 IU of factor VIII per unit of cryoprecipitate. In some embodiments, the composition comprises at least 150 mg of fibrinogen per unit of cryoprecipitate. In some embodiments, the composition further comprises plasma of a volume between about 15 mL and about 20 mL. In some embodiments, the composition comprises cryoprecipitate obtained from about 600 mL of pathogen-inactivated plasma. In some embodiments, the composition comprises cryoprecipitate obtained from about 600 mL of plasma, and the obtained cryoprecipitate has been pathogen-inactivated. In some embodiments, the composition comprises a first cryoprecipitate obtained from about 600 mL of pathogen-inactivated plasma and a second cryoprecipitate obtained from about 600 mL of pathogen-inactivated plasma, wherein the first and the second cryoprecipitates are combined prior to re-freezing for storage. In some embodiments, the composition comprises a first cryoprecipitate obtained from about 600 mL of plasma and a second cryoprecipitate obtained from about 600 mL of plasma, wherein the first and the second cryoprecipitates are combined prior to re-freezing for storage, and wherein the first and the second cryoprecipitates have been pathogen-inactivated after being combined and prior to re-freezing for storage. In some embodiments, the composition comprises a first cryoprecipitate obtained from about 600 mL of plasma and a second cryoprecipitate obtained from about 600 mL of plasma, wherein the first and the second cryoprecipitates are combined prior to re-freezing for storage, and wherein the first and the second cryoprecipitates have been pathogen-inactivated prior to being combined and prior to re-freezing for storage. In some embodiments, the composition comprises cryoprecipitate obtained from at least about 600 mL and less than 650 mL of pathogen-inactivated plasma. In some embodiments, the composition comprises cryoprecipitate obtained from at least about 600 mL and less than 650 mL of plasma, and the obtained cryoprecipitate has been pathogen-inactivated. In some embodiments, the composition comprises a first cryoprecipitate obtained from at least about 600 mL and less than 650 mL of pathogen-inactivated plasma and a second cryoprecipitate obtained from at least about 600 mL and less than 650 mL of pathogen-inactivated plasma, wherein the first and the second cryoprecipitates are combined prior to re-freezing for storage. In some embodiments, the composition comprises a first cryoprecipitate obtained from at least about 600 mL and less than 650 mL of plasma and a second cryoprecipitate obtained from at least about 600 mL and less than 650 mL of plasma, wherein the first and the second cryoprecipitates are combined prior to re-freezing for storage, and wherein the first and the second cryoprecipitates have been pathogen-inactivated after being combined and prior to re-freezing for storage. In some embodiments, the composition comprises a first cryoprecipitate obtained from at least about 600 mL and less than 650 mL of plasma and a second cryoprecipitate obtained from at least about 600 mL and less than 650 mL of plasma, wherein the first and the second cryoprecipitates are combined prior to re-freezing for storage, and wherein the first and the second cryoprecipitates have been pathogen-inactivated prior to being combined and prior to re-freezing for storage. In some embodiments, the composition further comprises plasma of a volume between about 40 mL and about 75 mL. In some embodiments, the composition further comprises plasma of a volume between about 50 mL and about 60 mL. In some embodiments, the composition is stored at room temperature for the at least 1 day after thawing. In some embodiments, the cryoprecipitate has been pathogen-inactivated by photochemical inactivation. In some embodiments, the cryoprecipitate has been pathogen-inactivated by photoinactivation with psoralen. In some embodiments, the psoralen is amotosalen.

In another aspect, the present disclosure provides a method of preparing a cryoprecipitate for infusion into a subject comprising a) preparing a cryoprecipitate from pathogen-inactivated plasma; b) freezing the cryoprecipitate; and c) thawing the frozen cryoprecipitate, wherein the resulting cryoprecipitate of step c) is suitable for infusion into a subject at least 1 day after thawing. In some embodiments, the resulting cryoprecipitate of step c) is suitable for infusion into a subject at least 5 days after thawing. In some embodiments, the method further comprises testing the thawed cryoprecipitate for fibrinogen. In some embodiments, the method does not comprise testing the thawed cryoprecipitate for factor VIII. In some embodiments, the cryoprecipitate is prepared from about 600 mL of pathogen-inactivated plasma. In some embodiments, the method further comprises combining a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to steps b) and c). In some embodiments, the cryoprecipitate is prepared from at least about 600 mL and less than 650 mL of pathogen-inactivated plasma. In some embodiments, the method further comprises combining a first cryoprecipitate prepared from at least about 600 mL and less than 650 mL of pathogen-inactivated plasma and a second cryoprecipitate prepared from at least about 600 mL and less than 650 mL of pathogen-inactivated plasma, wherein the first and the second cryoprecipitates are combined prior to steps b) and c). In some embodiments, the resulting cryoprecipitate of step c) is suitable for infusion into a subject at least 3 days after thawing. In some embodiments, the resulting cryoprecipitate of step c) is suitable for infusion into a subject at least 5 days after thawing. In some embodiments, the resulting cryoprecipitate of step c) is suitable for infusion into a subject at least 7 days after thawing.

In yet another aspect, the present disclosure provides a method of infusing a cryoprecipitate into a subject comprising a) preparing a cryoprecipitate from pathogen-inactivated plasma; b) freezing the cryoprecipitate; c) thawing the frozen cryoprecipitate; and d) infusing the thawed cryoprecipitate into a subject, wherein the infusion occurs at least 1 day after thawing the frozen cryoprecipitate. In some embodiments, the method further comprises testing the thawed cryoprecipitate for fibrinogen. In some embodiments, the method does not comprise testing the thawed cryoprecipitate for factor VIII before transfusing the thawed cryoprecipitate. In some embodiments, the cryoprecipitate is prepared from about 600 mL of pathogen-inactivated plasma. In some embodiments, the method further comprises combining a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to step b). In some embodiments, the cryoprecipitate is prepared from at least about 600 mL and less than 650 mL of pathogen-inactivated plasma. In some embodiments, the method further comprises combining a first cryoprecipitate prepared from at least about 600 mL and less than 650 mL of pathogen-inactivated plasma and a second cryoprecipitate prepared from at least about 600 mL and less than 650 mL of pathogen-inactivated plasma, wherein the first and the second cryoprecipitates are combined prior to step b).

In some embodiments of any of the above embodiments, the resulting cryoprecipitate of step c) comprises less than 80 IU of factor VIII per unit of cryoprecipitate. In some embodiments, the resulting cryoprecipitate of step c) comprises less than 50 IU of factor VIII per unit of cryoprecipitate. In some embodiments of any of the above embodiments, the resulting cryoprecipitate of step c) comprises at least 150 mg of fibrinogen per unit of cryoprecipitate. In some embodiments, the cryoprecipitate of step a) further comprises plasma of a volume between about 15 mL and about 20 mL. In some embodiments, the cryoprecipitate of step a) further comprises plasma of a volume between about 40 mL and about 75 mL. In some embodiments, the cryoprecipitate of step a) further comprises plasma of a volume between about 50 mL and about 60 mL. In some embodiments of any of the above embodiments, the plasma has been pathogen-inactivated by photochemical inactivation. In some embodiments, the cryoprecipitate has been pathogen-inactivated by photoinactivation with psoralen. In some embodiments, the psoralen is amotosalen. In some embodiments of any of the above embodiments, the subject is a human.

In still another aspect, the present disclosure provides a kit comprising a) a container; b) a pathogen-inactivated cryoprecipitate; and c) instructions for using the pathogen-inactivated cryoprecipitate in an infusion into a subject, wherein the instructions indicate that the cryoprecipitate is suitable for infusion into the subject for up to about 7 days after thawing. In some embodiments, the instructions indicate that the cryoprecipitate is suitable for infusion into the subject for up to about 5 days after thawing. In some embodiments, the instructions indicate that the cryoprecipitate is suitable for infusion into the subject for up to about 3 days after thawing.

In still another aspect, the present disclosure provides a method of infusing a cryoprecipitate into a subject, comprising infusing into the subject the composition of any of the above embodiments.

In still another aspect, the present disclosure provides a method infusing a cryoprecipitate into a subject, comprising infusing into the subject a cryoprecipitate produced by the method of any of the above embodiments.

In still another aspect, the present disclosure provides a cryoprecipitate produced by the method of any of the above embodiments.

In still another aspect, the present disclosure provides a composition comprising a cryoprecipitate suitable for infusion into a subject at least 1 day after thawing, wherein the cryoprecipitate is pathogen-inactivated. In some embodiments, the composition is suitable for infusion into a subject at least 3 days after thawing. In some embodiments, the composition is suitable for infusion into a subject at least 5 days after thawing. In some embodiments, the composition comprises cryoprecipitate prepared from at least about 550 mL and less than about 650 mL of pathogen-inactivated plasma. In some embodiments, the composition comprises cryoprecipitate prepared from at least about 550 mL and less than about 650 mL of plasma, and the prepared cryoprecipitate has been pathogen-inactivated. In some embodiments, the composition comprises cryoprecipitate prepared from about 600 mL of pathogen-inactivated plasma. In some embodiments, the composition comprises cryoprecipitate prepared from about 600 mL of plasma, and the prepared cryoprecipitate has been pathogen-inactivated. In some embodiments, the composition comprises cryoprecipitate prepared from 3 units of pathogen-inactivated plasma. In some embodiments, the composition comprises cryoprecipitate prepared from 3 units of plasma, and the prepared cryoprecipitate has been pathogen-inactivated. In some embodiments, the composition comprises a first cryoprecipitate prepared from at least about 550 mL and less than 650 mL of pathogen-inactivated plasma and a second cryoprecipitate prepared from at least about 550 mL and less than 650 mL of pathogen-inactivated plasma, wherein the first and the second cryoprecipitates are combined prior to re-freezing for storage. In some embodiments, the composition comprises a first cryoprecipitate prepared from at least about 550 mL and less than 650 mL of plasma and a second cryoprecipitate prepared from at least about 550 mL and less than 650 mL of plasma, wherein the first and the second cryoprecipitates are combined prior to re-freezing for storage, and wherein the first and the second cryoprecipitates have been pathogen-inactivated after being combined and prior to re-freezing for storage. In some embodiments, the composition comprises a first cryoprecipitate prepared from at least about 550 mL and less than 650 mL of plasma and a second cryoprecipitate prepared from at least about 550 mL and less than 650 mL of plasma, wherein the first and the second cryoprecipitates are combined prior to re-freezing for storage, and wherein the first and the second cryoprecipitates have been pathogen-inactivated prior to being combined and prior to re-freezing for storage. In some embodiments, the composition comprises a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to re-freezing for storage. In some embodiments, the composition comprises a first cryoprecipitate prepared from about 600 mL of plasma and a second cryoprecipitate prepared from about 600 mL of plasma, wherein the first and the second cryoprecipitates are combined prior to re-freezing for storage, and wherein the first and the second cryoprecipitates have been pathogen-inactivated prior to being combined and prior to re-freezing for storage. In some embodiments, the composition comprises a first cryoprecipitate prepared from about 600 mL of plasma and a second cryoprecipitate prepared from about 600 mL of plasma, wherein the first and the second cryoprecipitates are combined prior to re-freezing for storage, and wherein the first and the second cryoprecipitates have been pathogen-inactivated after being combined and prior to re-freezing for storage. In some embodiments, the composition comprises a first cryprecipitate prepared from 3 units of pathogen-inactivated plasma and a second cryoprecipitate prepared from 3 units of pathogen-inactivated plasma, wherein the first and the second cryoprecipitates are combined prior to re-freezing for storage. In some embodiments, the composition comprises a first cryprecipitate prepared from 3 units of plasma and a second cryoprecipitate prepared from 3 units of plasma, wherein the first and the second cryoprecipitates are combined prior to re-freezing for storage, and wherein the first and the second cryoprecipitates have been pathogen-inactivated after being combined and prior to re-freezing for storage. In some embodiments, the composition comprises a first cryprecipitate prepared from 3 units of plasma and a second cryoprecipitate prepared from 3 units of plasma, wherein the first and the second cryoprecipitates are combined prior to re-freezing for storage, and wherein the first and the second cryoprecipitates have been pathogen-inactivated prior to being combined and prior to re-freezing for storage. In some embodiments, the composition comprises cryoprecipitate prepared from 6 units of pathogen-inactivated plasma. In some embodiments, the composition comprises cryoprecipitate prepared from 6 units of plasma, and the prepared cryoprecipitate has been pathogen-inactivated. In some embodiments, the composition comprises cryoprecipitate prepared from plasma obtained from one donor. In some embodiments, the composition comprises cryoprecipitate prepared from plasma obtained from 2-6 donors. In some embodiments, the composition comprises less than 80 IU of factor VIII per unit of cryoprecipitate. In some embodiments, the composition comprises less than 50 IU of factor VIII per unit of cryoprecipitate. In some embodiments, the composition comprises 80-100 IU of factor VIII per unit of cryoprecipitate. In some embodiments, the composition comprises at least 80 IU of factor VIII. In some embodiments, the composition comprises 80-240 IU of factor VIII. In some embodiments, the composition comprises 80-480 IU of factor VIII. In some embodiments, the amount of factor VIII is determined from cryoprecipitate sampled within about 2 hours after thawing. In some embodiments, the amount of factor VIII is determined from cryoprecipitate sampled about 1 day after thawing. In some embodiments, the amount of factor VIII is determined from cryoprecipitate sampled about 3 days after thawing. In some embodiments, the amount of factor VIII is determined from cryoprecipitate sampled about 5 days after thawing. In some embodiments, the composition comprises at least 150 mg of fibrinogen per unit of cryoprecipitate. In some embodiments, the composition comprises at least 250 mg of fibrinogen per unit of cryoprecipitate. In some embodiments, the composition comprises at least 750 mg of fibrinogen. In some embodiments, the composition comprises at least 1500 mg of fibrinogen. In some embodiments, each unit of cryoprecipitate is prepared from 180-250 mL of pathogen-inactivated plasma. In some embodiments, the composition further comprises plasma of a volume between about 5 mL and about 20 mL per unit of cryoprecipitate. In some embodiments, the composition further comprises plasma of a volume greater than about 1 mL and less than or equal to about 75 mL. In some embodiments, the composition further comprises plasma of a volume between about 50 mL and about 60 mL. In some embodiments, the composition further comprises plasma of a volume between about 30 mL and about 120 mL. In some embodiments, the composition is stored at room temperature for at least 1 day after thawing. In some embodiments, the composition is stored at between about 2° C. and about 6° C. for at least 1 day after thawing. In some embodiments, the cryoprecipitate has been pathogen-inactivated by photochemical inactivation. In some embodiments, the cryoprecipitate has been pathogen-inactivated by photochemical inactivation with a psoralen. In some embodiments, the psoralen is amotosalen. In some embodiments, the cryoprecipitate is prepared from plasma that has been pathogen-inactivated in a first container suitable for photochemical inactivation of the plasma under sterile conditions; wherein the first container is coupled to a compound absorption device (CAD) such that the pathogen-inactivated plasma can be transferred from the first container to the CAD under sterile conditions; and wherein the cryoprecipitate is contained within one or more second containers, each of which is coupled to the CAD such that the pathogen-inactivated plasma can be transferred from the CAD to the one or more second containers under sterile conditions, and each of which is suitable for freezing the pathogen-inactivated plasma followed by thawing of the pathogen-inactivated plasma under conditions that provide for the formation of the cryoprecipitate. In some embodiments, each of the one or more second containers is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the one or more second containers. In some embodiments, the cryoprecipitate is prepared from plasma that has been pathogen-inactivated in a first container suitable for photochemical inactivation of the plasma under sterile conditions; wherein the first container is coupled to a compound absorption device (CAD) such that the pathogen-inactivated plasma can be transferred from the first container to the CAD under sterile conditions; wherein the CAD is coupled to one or more second containers, each of which is coupled to the CAD such that the pathogen-inactivated plasma can be transferred from the CAD to the one or more second containers under sterile conditions; and wherein the cryoprecipitate is contained within a third container configured to be coupled to one or more second containers, such that the pathogen-inactivated plasma can be transferred from the CAD to the one or more second containers to the third container under sterile conditions, wherein the third container is suitable for freezing the pathogen-inactivated plasma followed by thawing of the pathogen-inactivated plasma under conditions that provide for the formation of the cryoprecipitate. In some embodiments, the third container is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the third container. In some embodiments, the composition is contained within a container that further comprises a label indicating that the composition is suitable for use for at least about 1 day after thawing. In some embodiments, the composition is contained within a container that further comprises a label indicating that the composition is suitable for use for at least about 3 days after thawing. In some embodiments, the composition is contained within a container that further comprises a label indicating that the composition is suitable for use for at least about 5 days after thawing. In some embodiments, the cryoprecipitate is prepared from plasma other than group O plasma.

In still another aspect, the present disclosure provides a method of preparing a cryoprecipitate for infusion into a subject comprising: a) preparing a cryoprecipitate from pathogen-inactivated plasma; b) freezing the cryoprecipitate; and c) thawing the frozen cryoprecipitate, wherein the resulting cryoprecipitate of step c) is suitable for infusion into a subject at least 1 day after thawing. In some embodiments, the thawed cryoprecipitate comprises at least about 150 mg of fibrinogen per unit of cryoprecipitate. In some embodiments, the thawed cryoprecipitate comprises at least about 750 mg of fibrinogen. In some embodiments, the method does not comprise determining the level of factor VIII before infusing the thawed cryoprecipitate. In some embodiments, the method further comprises determining the level of factor VIII in the thawed cryoprecipitate. In some embodiments, the cryoprecipitate is prepared from at least about 550 mL and less than about 650 mL of pathogen-inactivated plasma. In some embodiments, the cryoprecipitate is prepared from about 600 mL of pathogen-inactivated plasma. In some embodiments, the method further comprises combining a first cryoprecipitate prepared from at least about 550 mL and less than about 650 mL of pathogen-inactivated plasma and a second cryoprecipitate prepared from at least about 550 mL and less than about 650 mL of pathogen-inactivated plasma, wherein the first and the second cryoprecipitates are combined prior to steps b) and c). In some embodiments, the method further comprises combining a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to steps b) and c). In some embodiments, the method further comprises combining a first cryprecipitate prepared from 3 units of pathogen-inactivated plasma and a second cryoprecipitate prepared from 3 units of pathogen-inactivated plasma, wherein the first and the second cryoprecipitates are combined prior to steps b) and c). In some embodiments, the resulting cryoprecipitate of step c) is suitable for infusion into a subject at least 3 days after thawing. In some embodiments, the resulting cryoprecipitate of step c) is suitable for infusion into a subject at least 5 days after thawing. In another aspect, provided herein is a method of infusing a cryoprecipitate into a subject comprising: a) preparing a cryoprecipitate from pathogen-inactivated plasma; b) freezing the cryoprecipitate; c) thawing the frozen cryoprecipitate; and d) infusing the thawed cryoprecipitate into a subject, wherein the infusion occurs at least 1 day after thawing the frozen cryoprecipitate. In some embodiments, the thawed cryoprecipitate comprises at least about 150 mg of fibrinogen per unit of cryoprecipitate. In some embodiments, the thawed cryoprecipitate comprises at least about 750 mg of fibrinogen. In some embodiments, the method does not comprise determining the level of factor VIII before infusing the thawed cryoprecipitate. In some embodiments, the method further comprises determining the level of factor VIII in the thawed cryoprecipitate before infusing the thawed cryoprecipitate. In some embodiments, the cryoprecipitate is prepared from at least about 550 mL and less than about 650 mL of pathogen-inactivated plasma. In some embodiments, the cryoprecipitate is prepared from about 600 mL of pathogen-inactivated plasma. In some embodiments, the method further comprises combining a first cryoprecipitate prepared from at least about 550 mL and less than about 650 mL of pathogen-inactivated plasma and a second cryoprecipitate prepared from at least about 550 mL and less than about 650 mL of pathogen-inactivated plasma, wherein the first and the second cryoprecipitates are combined prior to steps b) and c). In some embodiments, the method further comprises combining a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to steps b) and c). In some embodiments, the method further comprises combining a first cryprecipitate prepared from 3 units of pathogen-inactivated plasma and a second cryoprecipitate prepared from 3 units of pathogen-inactivated plasma, wherein the first and the second cryoprecipitates are combined prior to steps b) and c). In some embodiments, the resulting cryoprecipitate of step c) comprises less than 80 IU of factor VIII per unit of cryoprecipitate. In some embodiments, the resulting cryoprecipitate of step c) comprises at least about 80 IU of factor VIII. In some embodiments, the resulting cryoprecipitate of step c) comprises 80-240 IU of factor VIII. In some embodiments, the resulting cryoprecipitate of step c) comprises 80-480 IU of factor VIII. In some embodiments, the resulting cryoprecipitate of step c) comprises less than 50 IU of factor VIII per unit of cryoprecipitate. In some embodiments of any of the above embodiments, the resulting cryoprecipitate of step c) comprises at least 150 mg of fibrinogen per unit of cryoprecipitate. In some embodiments of any of the above embodiments, the resulting cryoprecipitate of step c) comprises at least 750 mg of fibrinogen. In some embodiments of any of the above embodiments, the cryoprecipitate of step a) further comprises plasma of a volume between about 5 mL and about 20 mL per unit of cryoprecipitate. In some embodiments, the cryoprecipitate of step a) further comprises plasma of a volume greater than about 1 mL and less than or equal to about 75 mL. In some embodiments, the cryoprecipitate of step a) further comprises plasma of a volume between about 50 mL and about 60 mL. In some embodiments, the cryoprecipitate of step a) further comprises plasma of a volume between about 30 mL and about 120 mL. In some embodiments of any of the above embodiments, the plasma has been pathogen-inactivated by photochemical inactivation. In some embodiments, the cryoprecipitate has been pathogen-inactivated by photochemical inactivation with a psoralen. In some embodiments, the psoralen is amotosalen. In some embodiments of any of the above embodiments, the cryoprecipitate is prepared from plasma that has been pathogen-inactivated in a first container suitable for photochemical inactivation of the plasma under sterile conditions; wherein the first container is coupled to a compound absorption device (CAD) such that the pathogen-inactivated plasma can be transferred from the first container to the CAD under sterile conditions; and wherein the cryoprecipitate is frozen and thawed in steps b) and c) within one or more second containers, each of which is coupled to the CAD such that the pathogen-inactivated plasma can be transferred from the CAD to the one or more second containers under sterile conditions, and each of which is suitable for freezing the pathogen-inactivated plasma followed by thawing of the pathogen-inactivated plasma under conditions that provide for the formation of the cryoprecipitate. In some embodiments, each of the one or more second containers is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the one or more second containers. In some embodiments, the cryoprecipitate is prepared from plasma that has been pathogen-inactivated in a first container suitable for photochemical inactivation of the plasma under sterile conditions; wherein the first container is coupled to a compound absorption device (CAD) such that the pathogen-inactivated plasma can be transferred from the first container to the CAD under sterile conditions; and wherein the cryoprecipitate is frozen and thawed in steps b) and c) within a third container configured to be coupled to one or more second containers, such that the pathogen-inactivated plasma can be transferred from the CAD to the one or more second containers to the third container under sterile conditions, wherein the third container is suitable for freezing the pathogen-inactivated plasma followed by thawing of the pathogen-inactivated plasma under conditions that provide for the formation of the cryoprecipitate. In some embodiments, the third container is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the third container. In some embodiments of any of the above embodiments, the subject is a human.

In still another aspect, the present disclosure provides a kit comprising: a) a container; b) a pathogen-inactivated cryoprecipitate; and c) instructions for using the pathogen-inactivated cryoprecipitate in an infusion into a subject, wherein the instructions indicate that the cryoprecipitate is suitable for infusion into the subject for up to about 5 days after thawing.

In still another aspect, the present disclosure provides a kit comprising: a) a container; b) a pathogen-inactivated cryoprecipitate; and c) a label indicating that the pathogen-inactivated cryoprecipitate is suitable for use for up to about 5 days after thawing.

In still another aspect, the present disclosure provides a method of infusing a cryoprecipitate into a subject, comprising infusing into the subject the composition of any of the above embodiments.

In still another aspect, the present disclosure provides a method of infusing a cryoprecipitate into a subject, comprising infusing into the subject a cryoprecipitate produced by any of the above embodiments.

In still another aspect, the present disclosure provides a cryoprecipitate produced by any of the above embodiments.

In still another aspect, the present disclosure provides a method of preparing a pooled cryosupernatant for infusion into a subject comprising: a) freezing at least a first pathogen-inactivated plasma and a second pathogen-inactivated plasma, wherein the first and the second pathogen-inactivated plasmas each have a volume of at least about 550 mL and less than about 650 mL; b) thawing the first pathogen-inactivated plasma under conditions that provide for the formation of a first precipitate and a first supernatant, and thawing the second pathogen-inactivated plasma under conditions that provide for the formation of a second precipitate and a second supernatant; c) separating the first and the second supernatants from the first and the second precipitates to form a first crosupernatant and a second cryosupernatant; and d) combining the first and the second cryosupernatants to form a pooled cryosupernatant. In some embodiments, the first and the second pathogen-inactivated plasmas each have a volume of about 600 mL. In some embodiments, step a) further comprises freezing at least a third pathogen-inactivated plasma and a fourth pathogen-inactivated plasma, wherein the third and the fourth pathogen-inactivated plasmas each have a volume of at least about 550 mL and less than 650 mL; step b) further comprises thawing the third pathogen-inactivated plasma under conditions that provide for the formation of a third precipitate and a third supernatant, and thawing the fourth pathogen-inactivated plasma under conditions that provide for the formation of a fourth precipitate and a fourth supernatant; step c) further comprises separating the third and the fourth supernatants from the third and the fourth precipitates to form a third cryosupernatant and a fourth cryosupernatant; the pooled cryosupernatant formed in step d) is a first pooled supernatant, and step d) further comprises combining the third and the fourth cryosupernatants to form a second pooled cryosupernatant; and the method further comprises e) combining the first pooled cryosupernatant and the second pooled cryosupernatant. In some embodiments, the third and the fourth pathogen-inactivated plasmas each have a volume of about 600 mL. In some embodiments, the first and/or the second pathogen-inactivated plasma have been pathogen-inactivated by photochemical inactivation. In some embodiments, the one or more of the first, second, third, and fourth pathogen-inactivated plasmas have been pathogen-inactivated with a psoralen. In some embodiments, the psoralen is amotosalen. In some embodiments, one or more of the first, second, third, and fourth pathogen-inactivated plasmas have been pathogen-inactivated in a first container suitable for photochemical inactivation of plasma under sterile conditions, wherein the first container is coupled to a compound absorption device (CAD) such that the pathogen-inactivated plasma can be transferred from the first container to the CAD under sterile conditions. In some embodiments, one or more of the first, second, third, and fourth pathogen-inactivated plasmas is frozen in step a) and thawed in step b) within one or more second containers, each of which is coupled to the CAD such that the pathogen-inactivated plasma can be transferred from the CAD to the one or more second containers under sterile conditions, and each of which is suitable for freezing the pathogen-inactivated plasma followed by thawing of the pathogen-inactivated plasma under conditions that provide for the formation of the cryoprecipitate. In some embodiments, one or more of the first, second, third, and fourth pathogen-inactivated plasmas is frozen in step a) and thawed in step b) within a third container configured to be coupled to the one or more second containers, such that the pathogen-inactivated plasma can be transferred from the CAD to the one or more second containers to the third container under sterile conditions, wherein the third container is suitable for freezing the pathogen-inactivated plasma followed by thawing of the pathogen-inactivated plasma under conditions that provide for the formation of the cryoprecipitate. In some embodiments, one or more of the first, second, third, and fourth supernatants is separated from one or more of the first, second, third, and fourth precipitates in step c) within one or more fourth containers, each of which is configured to be coupled to the one or more second containers or to the third container such that the supernatant can be transferred from the one or more second containers or the third container to the one or more fourth containers under sterile conditions to afford a pathogen-inactivated cryosupernatant contained within the one or more fourth containers and a pathogen-inactivated cryoprecipitate contained within the one or more second containers or the third container.

In still another aspect, the present disclosure provides a method of infusing a cryosupernatant into a subject, comprising infusing into the subject a cryosupernatant produced by the method of any of the above embodiments.

In still another aspect, the present disclosure provides a processing set for preparing a pathogen-inactivated cryoprecipitate, comprising a) a first container within which one or more units of a plasma can be photochemically inactivated in the presence of a psoralen under sterile conditions; b) a compound absorption device (CAD) coupled to the first container such that the one or more units of plasma can be transferred from the first container to the compound absorption device under sterile conditions; and c) one or more second containers, each of which is coupled to the compound absorption device such that the one or more units of plasma can be transferred from the compound absorption device to the one or more second containers under sterile conditions to provide pathogen-inactivated plasma suitable for infusion into a subject, wherein the one or more second containers is suitable for freezing the pathogen-inactivated plasma followed by thawing of the pathogen-inactivated plasma under conditions that provide for the formation of a precipitate and a supernatant. In some embodiments, each of the one or more second containers is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the one or more second containers.

In still another aspect, the present disclosure provides a processing set for preparing a pathogen-inactivated cryoprecipitate, comprising a) a first container within which one or more units of a plasma can be photochemically inactivated in the presence of a psoralen under sterile conditions; b) a compound absorption device (CAD) coupled to the first container such that the one or more units of plasma can be transferred from the first container to the compound absorption device under sterile conditions; c) one or more second containers, each of which is coupled to the compound absorption device such that the one or more units of plasma can be transferred from the compound absorption device to the one or more second containers under sterile conditions to provide pathogen-inactivated plasma suitable for infusion into a subject; and d) a third container, which is configured to be coupled to the one or more second containers such that the pathogen-inactivated plasma can be transferred from the one or more second containers to the third container under sterile conditions, wherein the third container is suitable for freezing the pathogen-inactivated plasma followed by thawing of the pathogen-inactivated plasma under conditions that provide for the formation of a precipitate and a supernatant. In some embodiments, the third container is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the third container. In some embodiments, the processing set further comprises an additional container suitable for mixing the one or more units of plasma with a pathogen inactivation compound, wherein the additional container is coupled to the first container such that the one or more units of plasma in admixture with the pathogen-inactivating compound can be transferred from the additional container to the first container under sterile conditions. In some embodiments, the processing set further comprises one or more fourth containers, each of which is configured to be coupled to the one or more second containers or to the third container such that the supernatant can be transferred from the one or more second containers or the third container to the one or more fourth containers under sterile conditions to provide a pathogen-inactivated cryosupernatant contained within the one or more fourth containers and a pathogen-inactivated cryoprecipitate contained within the one or more second containers or the third container. In some embodiments, the third container is coupled to the one or more second containers such that the supernatant can be transferred from the one or more second containers to the third container under sterile conditions to afford a pathogen-inactivated cryosupernatant contained within the third container and a pathogen-inactivated cryoprecipitate contained within the one or more second containers. In some embodiments, the third container is configured to be coupled to the one or more second containers such that the pathogen-inactivated plasma can be transferred from the one or more second containers to the third container under sterile conditions; wherein the third container is suitable for freezing the pathogen-inactivated plasma followed by thawing of the pathogen-inactivated plasma under conditions that provide for the formation of a precipitate and a supernatant; and wherein each of the one or more fourth containers is configured to be coupled to the third container such that the supernatant can be transferred from the third container to the one or more fourth containers under sterile conditions to afford a pathogen-inactivated cryosupernatant contained within the one or more fourth containers and a pathogen-inactivated cryoprecipitate contained within the third container.

In still another aspect, the present disclosure provides a method of preparing a cryoprecipitate for infusion into a subject comprising: a) preparing a cryoprecipitate from pathogen-inactivated plasma; and b) freezing the cryoprecipitate; wherein the cryoprecipitate is suitable for infusion into the subject for up to about 5 days after thawing. In some embodiments, the cryoprecipitate is prepared from at least about 550 mL and less than about 650 mL of pathogen-inactivated plasma. In some embodiments, the cryoprecipitate is prepared from about 600 mL of pathogen-inactivated plasma. In some embodiments, the method further comprises combining a first cryoprecipitate prepared from at least about 550 mL and less than about 650 mL of pathogen-inactivated plasma and a second cryoprecipitate prepared from at least about 550 mL and less than about 650 mL of pathogen-inactivated plasma, wherein the first and the second cryoprecipitates are combined prior to step b). In some embodiments, the first cryoprecipitate is prepared from about 600 mL of pathogen-inactivated plasma, and wherein the second cryoprecipitate is prepared from about 600 mL of pathogen-inactivated plasma. In some embodiments, the method further comprises combining a first cryprecipitate prepared from 3 units of pathogen-inactivated plasma and a second cryoprecipitate prepared from 3 units of pathogen-inactivated plasma, wherein the first and the second cryoprecipitates are combined prior to step b).

In still another aspect, the present disclosure provides a method of preparing a cryoprecipitate for infusion into a subject comprising: a) preparing a cryoprecipitate from plasma; and b) subjecting the cryoprecipitate to pathogen inactivation; wherein the pathogen-inactivated cryoprecipitate is suitable for infusion into the subject for up to about 5 days after storage at between about 2° C. and about 25° C. In some embodiments, the plasma is not pathogen-inactivated. In some embodiments, the method further comprises, after step b): c) freezing the pathogen-inactivated cryoprecipitate; and d) thawing the frozen pathogen-inactivated cryoprecipitate; wherein the pathogen-inactivated cryoprecipitate is suitable for infusion into the subject for up to about 3 days after thawing. In some embodiments, the pathogen-inactivated cryoprecipitate is suitable for infusion into the subject for up to about 5 days after thawing. In some embodiments, the cryoprecipitate is prepared from 1 unit of plasma. In some embodiments, the cryoprecipitate is prepared from at least about 180 mL and less than about 250 mL of plasma. In some embodiments, the prepared cryoprecipitate is resuspended in at least about 30 mL and less than about 70 mL of plasma. In some embodiments, the method further comprises combining at least a first cryoprecipitate prepared from 1 unit of plasma and a second cryoprecipitate prepared from 1 unit of plasma, wherein the first and the second cryoprecipitates are combined prior to step b). In some embodiments, the method further comprises combining at least a first cryoprecipitate prepared from 1 unit of plasma and a second cryoprecipitate prepared from 1 unit of plasma, wherein the first and the second cryoprecipitates are combined after step b). In some embodiments, the first cryoprecipitate is prepared from at least about 180 mL and less than about 250 mL of plasma, and wherein the second cryoprecipitate is prepared from at least about 180 mL and less than about 250 mL of plasma. In some embodiments, combining at least a first cryoprecipitate and a second cryoprecipitate comprises combining 2-12 cryoprecipitates. In some embodiments, the volume of the combined cryoprecipitates is at least about 500 mL and less than about 700 mL. In some embodiments, the first and the second cryoprecipitates are prepared from plasma of the same ABO type. In some embodiments, the first and the second cryoprecipitates are prepared from plasma of different ABO types. In some embodiments, the combined cryopreciptiates are prepared from at least 3 cryoprecipitates, and each of the cryoprecipitates is prepared from plasma of a different ABO type. In some embodiments, the cryoprecipitate is prepared from whole-blood derived plasma. In some embodiments, the cryoprecipitate is prepared from apheresis collected plasma. In some embodiments, the apheresis collected plasma is between about 200 mL and about 800 mL.

It is to be understood that one, some, or all of the properties of the various embodiments described herein may be combined to form other embodiments. These and other aspects will become apparent to one of skill in the art. These and other embodiments are further described by the detailed description that follows.

BRIEF DESCRIPTION OF THE DRAWINGS

FIG. 1A shows an exemplary processing kit in accordance with some embodiments. Dotted components are optional.

FIG. 2A shows an exemplary processing kit in accordance with some embodiments. Dotted components are optional.

FIG. 2B shows an exemplary processing kit in accordance with some embodiments. Dotted components are optional.

FIG. 2C shows an exemplary processing kit in accordance with some embodiments. Dotted components are optional.

FIG. 3B shows an exemplary processing kit in accordance with some embodiments. Dotted components are optional.

FIG. 4 depicts combining two separate cryoprecipitate preparations in accordance with some embodiments.

DETAILED DESCRIPTION

Figure 1B:
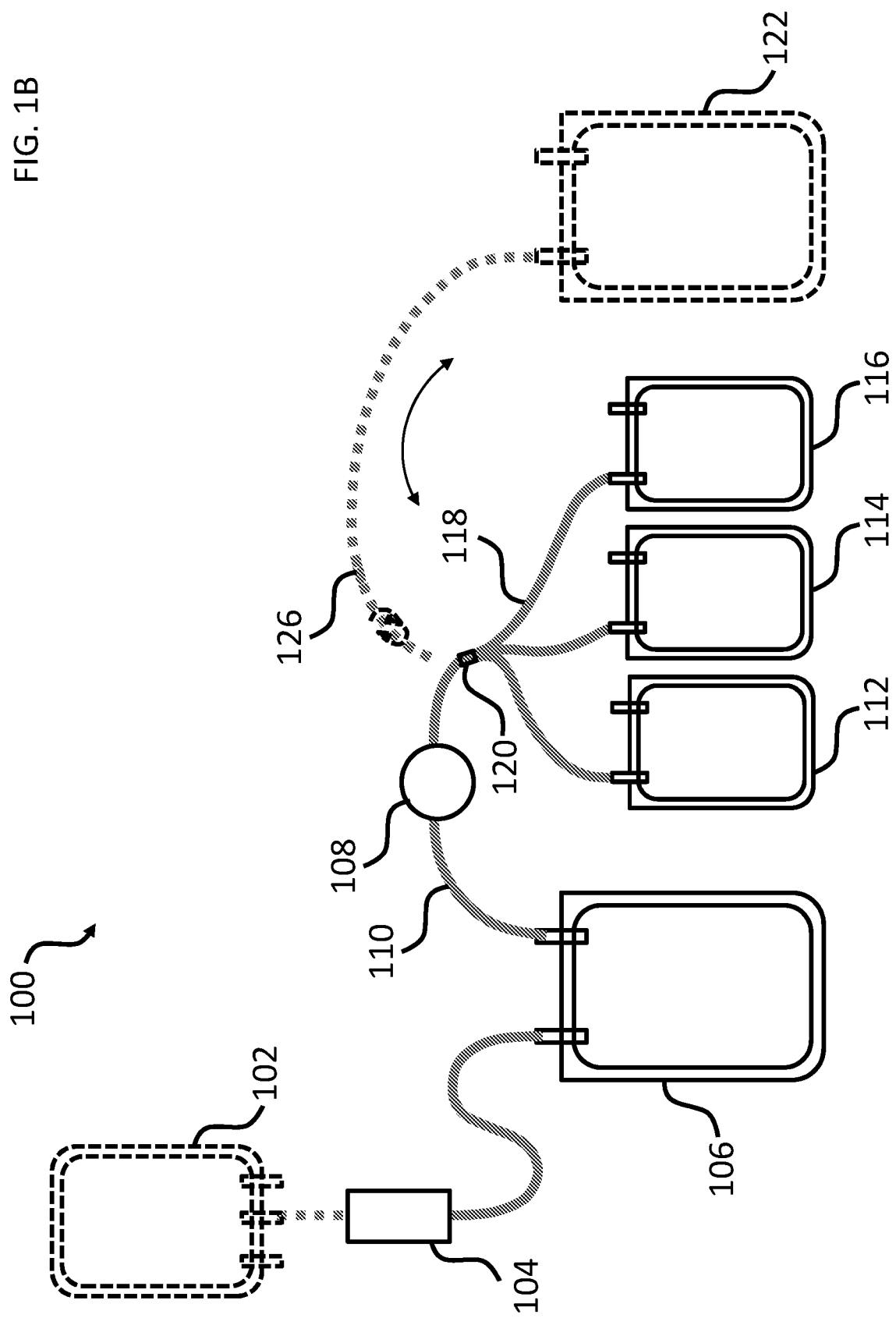
FIG. 1B shows an exemplary processing kit in accordance with some embodiments. Dotted components are optional.

The term "cryoprecipitate" refers to a blood product produced by controlled thawing of frozen plasma (e.g., whole blood-derived fresh frozen plasma, apheresis derived plasma) to form a precipitate comprising one or more coagulation factors including without limitation fibrinogen, Factor VIII, Factor XIII, vWF, and/or fibronectin. Such cryoprecipitate may be recovered from the liquid plasma portion, for example, by refrigerated centrifugation. A cryoprecipitate may be resuspended in any suitable volume of plasma after recovery. Methods for preparing a cryoprecipitate are well known in the art and provided throughout the present disclosure.

The term "plasma" refers to any plasma blood product known in the art. In some embodiments, plasma refers to whole blood-derived fresh frozen plasma. In some embodiments, plasma refers to one or more plasma units from a whole blood donation (e.g., approximately 180-250 mL volume each). In some embodiments, plasma refers to one or more plasma units from an apheresis blood donation (may be up to approximately 700-800 mL each). In some embodiments, plasma refers to a single unit. In some embodiments, plasma may be pooled from multiple units. In some embodiments, plasma may contain one or more additional components, including, without limitation, one or more pathogen-inactivation compounds and/or byproducts of a pathogen-inactivation process.

The term "suitable for infusion" refers to any blood product (e.g., a cryoprecipitate) able to be used for an infusion (e.g., a transfusion) into a subject (e.g., a human patient) according to medical judgement. In some embodiments, suitability refers to having sufficient biological activity for its intended use, i.e., for use where a transfusion of human coagulation factors is indicated, including, without limitation, control of bleeding associated with fibrinogen deficiency, treating Factor XIII deficiency, treating Factor VIII deficiency, treating von Willebrand disease, maintenance of hemostasis, treating disseminated intravascular coagulation (DIC) or high volume hemorrhage, and/or making fibrin sealant. In some embodiments, suitability refers to having sufficient safety, e.g., that the product has undergone a treatment that improves product safety (e.g., pathogen inactivation) and/or demonstrates satisfactory performance with respect to one or more safety-related measurements (such as viral or bacterial titer). Photochemical inactivation of pathogens in blood product units using amotosalen and UVA light as described herein is well established to provide such a blood product (e.g., cryoprecipitate) that is suitable for transfusion into humans. In some embodiments, suitability refers to meeting one or more standards (e.g., having a level of a biological activity or a biological component, a safety criterion, and the like) established by an accrediting agency or regulatory body that governs infusion practices, such as the AABB.

"Pathogen-inactivated" as used herein describes a blood product (e.g., a cryoprecipitate or plasma) that has undergone processing (e.g., by the methods described herein) to inactivate pathogens that may be present. It is understood that a pathogen-inactivated cryoprecipitate may include a cryoprecipitate that has itself undergone pathogen inactivation, or a cryoprecipitate made from a pathogen-inactivated blood product (e.g., plasma, whole blood, and the like). It is further understood that the process does not necessarily inactivate completely all pathogens that may be present, but substantially reduces the amount of one or more pathogens to significantly reduce the risk of a transfusion-associated disease. The inactivation of a pathogen may be assayed by measuring the number of infective pathogens (e.g., virus or bacteria) in a certain volume, and the level of inactivation is typically represented by the log reduction in the infectivity of the pathogen, or log reduction in titer. Methods of assaying log reduction in titer, and measurements thereof for pathogen inactivation are known in the art. Methods of assaying log reduction in titer, and measurements thereof for pathogen inactivation are described, for example, in U.S. Pat. No. 7,655,392, the disclosure of which is hereby incorporated by reference as it relates to assays for pathogen inactivation. As such, for any given pathogen, known amounts can be added to a test unit of cryoprecipitate or plasma to assess how much inactivation results from the process, where typically the pathogen inactivation process results in at least about 1 log reduction in titer, or about 2 log, about 3 log, about 4 log, or at least about 5 log reduction in titer. While the methods as described herein are applicable to any pathogen-inactivation treatment, it is desirable that the pathogen-inactivation treatment is capable of inactivating a variety of pathogens to at least 1 log reduction in titer, including a pathogen selected from the group consisting of HIV-1, HBV, HCV, HTLV-1, HTLV-2, West Nile virus, *Escherichia coli, Klebsiella pneumoniae, Yersinia enterocolitica, Staphylococcus epidermidis, Staphylococcus aureus, Treponema pallidum, Borrelia burgdorferi, Plasmodium falciparum, Trypanosoma cruzi*, and *Babesia microti*.

The term "pathogen inactivation compound" means any suitable compound, such as a small organic compound, that can be used to inactivate a pathogen that may be present in a blood product such as cryoprecipitate or plasma. A "photoactivated pathogen inactivation compound" is a suitable compound that requires some level of light (e.g., ultraviolet light) in order to sufficiently inactivate a pathogen. Such compounds are preferred in the inactivation of pathogens in blood products such as cryoprecipitate or plasma as they provide control over the inactivation process. Such photoactivated pathogen inactivation compounds described herein include psoralens, isoalloxazines, alloxazines, phthalocyanines, phenothiazines, and porphyrins, where these terms are understood to encompass a general class of compounds, i.e. the core compound and suitable derivatives thereof. For example, psoralens or a psoralen generally describes the psoralen core compound and any derivative thereof (e.g. amotosalen), isoalloxazines or an isoalloxazine generally describes the isoalloxazine core and any derivative thereof (e.g. riboflavin), and so forth. Such derivatives comprise the core compound structure as well as additional substituents on the core. Descriptions of such compounds include any salts thereof.

The term "amotosalen" means the compound 3-(2-aminoethoxymethyl)-2,5,9-trimethylfuro[3,2-g]chromen-7-one and any salts thereof. The compound may also be referred to as 3-[(2-aminoethoxy)methyl]-2,5,9-trimethyl-7H-furo[3,2-G][1]benzopyran-7-one-hydrochloride. The compound may also be referred to as 4'-(4-amino-2-oxa)butyl-4,5',8-trimethyl psoralen. Where the inactivation of blood products such as cryoprecipitate or plasma includes adding amotosalen HCl (the HCl salt of amotosalen) to a unit of blood product, the removal of this compound from the unit is not limited to the removal of amotosalen HCl, as the amotosalen can be present in solution as other salts or as the free base. As used in the methods described herein, removal of amotosalen means removal of the compound in any form, e.g. as the free base or as any salt, as measured by the assays described herein. Treatment or processing of blood products by amotosalen inactivation refers to combining a blood product (e.g., unit of cryoprecipitate or plasma, individual unit, pooled) with amotosalen and illuminating with a suitable dose of UVA light in order to inactivate pathogens that may be present. In some embodiments, amotosalen-inactivated cryoprecipitate has been pathogen inactivated, or the plasma from which the cryoprecipitate has been produced has been pathogen inactivated, according to commercial methods, or by similar methods.

The term "under sterile conditions" as used herein refers to maintaining the sterility of the system, for example by connection of two bags from a blood processing set, or refers to a means by which the process does not introduce contamination. For example, as used in the methods described herein, a source unit of blood product such as cryoprecipitate or plasma comprising a tubing for connection to a processing set or container of pathogen inactivation compound comprising a similar tubing may be joined under sterile condition by methods known in the art, for example using a sterile connecting device, which acts to melt or weld the tubing together to provide a sterile flow path between the two containers. Similarly, when methods described herein describe sealing off such tubing, the sealing is done under sterile conditions, for example using a tubing welder.

A "blood-collection bag" can be any bag used for collecting blood from a donor as known in the art. Blood collected in a blood-collection bag that is not attached to other bags may be centrifuged to separate the blood into blood components. Then, the blood-collection bag is sterile docked to a number of satellite bags that corresponds to the number of blood products it has been determined to manufacture from the whole blood. Blood in a blood-collection bag may be processed, such as by centrifuging and/or freezing, in the blood-collection bag before separation into satellite bags, or the blood may be transferred (by gravity or by pumping) from the blood-collection bag to a blood-processing bag.

A "blood-processing bag" is any such bag known in the art, other than the blood-collection bag, used for processing blood. The blood-processing bag may be pre-connected to the blood-collection bag or attached to the blood-collection bag through sterile docking. Blood transferred to a blood-processing bag may be centrifuged. Prior to centrifuging or immediately after centrifuging, the blood-processing bag is sterile docked to a number of satellite bags that corresponds to the number of blood products it has been determined to manufacture from the whole blood.

Blood Collection and Cryoprecipitate Preparation

Whole blood for use in the preparation of cryoprecipitate as described herein may be collected by a variety of procedures known in the art. One of the most common blood collection techniques, is the "manual" collection of whole blood from healthy donors. As commonly understood and as used herein, manual collection refers to a collection method where whole blood is allowed to drain from the donor and into a collection container without the use of external pumps or similar devices. This is in contrast to so-called automated procedures where blood is withdrawn from a donor and further processed by an instrument that typically includes a processing or separation device and pumps for moving blood or blood components into and out of the device. Automated cell separation systems may be used to collect plasma from a donor by an apheresis procedure (e.g., plasmapheresis), while returning other blood components to the donor. Apheresis collected plasma also may be used for the preparation of cryoprecipitate and cryo poor plasma using the methods and kits provided herein.

Regardless of whether the blood collection technique is manual or automated, withdrawing blood from the donor typically includes inserting a vein access device, such as a needle, into the donor's arm (and, more specifically, the donor's vein) and withdrawing blood from the donor through the needle. The "venipuncture" needle typically has attached to it, one end of a plastic tube that provides a flow path for the blood. The other end of the plastic tube terminates in one or more pre-attached plastic blood containers or bags for collecting the blood. The needle, tubing and containers make up a blood collection set which is pre-sterilized and disposed of after a single use. The sterile blood collection container typically serves as the primary container for initial separation of blood components (e.g., separation of plasma from red blood cells and platelets).

The blood collection container and plastic tubing may also include a volume of a liquid anticoagulant, while in the automated technique, a separate container of anticoagulant may be provided from which the anticoagulant is metered into the flow path and mixed with the incoming whole blood. Anticoagulant is required because of the tendency of blood to clot and adhere to the walls of the plastic surfaces which it. Exemplary anticoagulants are well known in the art and may include, but are not limited to, an anticoagulant citrate phosphate dextrose (CPD) solution, an anticoagulant citrate phosphate double dextrose (CP2D) solution, an anticoagulant citrate phosphate dextrose adenine (CPDA) solution (e.g., CPDA-1), an acid citrate dextrose (ACD) solution (e.g., ACD-A), and an anticoagulant sodium citrate 4% w/v solution.

Blood may be identified or characterized with respect to one or more parameters, such as for example, hematocrit. Such identification or characterization is typically prior to or shortly after blood collection, but prior to subjecting the collected whole blood to further processing, such as according to the methods provided herein. In addition, at or near the time of collection and prior to transfusion to a patient, tests may be performed for determining blood type and the presence of pathogens such as virus, bacteria and/or other foreign substances in the donor's blood. Such testing generally requires obtaining a sample of the donor's blood. Generally sampling of blood may be before, during or after donation, but without compromising the sterility of the system and/or the collected blood product. For example, samples may be commonly obtained by finger stick, heel stick or venipuncture. In the case where blood for hemoglobin testing is gathered with a capillary stick, a single-use sterile lancet may be used. Another well-known technique is to simply withdraw or collect the blood remaining in the flow path of the collection set after donation. This involves removing the needle from the donor, inserting the needle into a vacuum sealed sampling vial or tube and allowing the blood from the flow path to drain into the vial. Another alternative is to clamp off the flow path near the collection container and divert the blood being withdrawn from the donor to a collection (sampling) vial or tube. This procedure may employ a particular type of disposable tubing set having a pre-attached sampling site on the main flow path. Blood at or near the sampling site may be obtained by piercing the sampling site with a separately provided needle or other piercing device, and attaching a sampling vial thereto. To minimize the risk that the incoming blood will be exposed to the outside environment, the sample is typically collected after completion of the blood donation. Alternatively, some collection bags or collection sets include diversion pouches to sequester a portion (e.g., the first 20 ml) of blood collected. Another example of a blood sampling system is described in U.S. Pat. No. 5,167,656, which describes blood collection sets with an enlarged sample collection portion included in the flow path. Blood for sampling is collected in the enlarged portion by clamping off the flow path near the collection container and allowing the enlarged tubing portion to fill with blood.

Plasma useful for cryoprecipitate preparation as described herein may be recovered from whole blood by a variety of procedures known in the art. For example, plasma may be recovered by centrifuging whole blood at low speed (e.g., approximately 1000-3000 rpm for approximately 10-20 minutes, optionally under refrigeration), followed by recovery of the plasma fraction. In some embodiments, the plasma may be depleted of platelets (e.g., by centrifugation at higher speeds and/or longer times within the above ranges, such as approximately 2000-3000 rpm for approximately 15-20 minutes, or approximately 5000×g).

Methods for producing a cryoprecipitate from plasma are well known in the art and described and exemplified herein. Typically individual units of whole blood derived plasma used for preparation of cryoprecipitate are frozen within 8 hours of donation and the frozen plasma (e.g., whole blood-derived fresh frozen plasma, or FFP) may be thawed in a temperature controlled apparatus, such as a water bath. The present disclosure also contemplates that whole blood derived plasma frozen within 24 hours of donation and plasma produced by apheresis (e.g., frozen with 8 hours, frozen within 24 hours) may be used. For thawing, the temperature may be sufficiently low (e.g., at approximately 4° C., or between about 1° C. and about 6° C.) so as to result in a controlled, gradual thawing. For example, the thawing may take place over a total time of between about 4 hours and about 7-8 hours, 8-10 hours, or overnight. As discussed in greater detail supra, individual units (e.g., 200 mL units, as defined by an accepted standard such as AABB) of plasma may be used to produce a cryoprecipitate, or more than one individual unit (e.g., 200 mL units) of plasma may be pooled to produce a cryoprecipitate (e.g., 550-650 mL of plasma). For pooled plasma, a larger suitable bag such as a 1000 mL PVC bag (e.g., a Fenwal transfer pack) or any blood product compatible bag of sufficient volume (e.g., 800 mL, 600 mL) may be used to produce the cryoprecipitate. In some embodiments, the total thaw time may be dependent on the volume of plasma; e.g., a 200-250 mL unit of plasma may thaw for approximately 4.5 hours, whereas 550-650 mL of plasma may take approximately 6.5 hours. After thawing, the plasma may be centrifuged, e.g., under refrigeration (such as at approximately 4° C.) for approximately 10-15 minutes at approximately 4200 rcf (optionally with a slow stop) to separate the cryoprecipitate from the cryo-poor plasma (cryosupernatant). The cryoprecipitate may be separated from the cryo-poor plasma, e.g., by inversion to remove the cryo-poor plasma, or through use of a plasma expressor to remove the cryo-poor plasma.

In some embodiments, cryoprecipitate may be frozen after production. As the cryoprecipitate may be derived from plasma that has itself been frozen, "re-freezing" the cryoprecipitate as used herein refers to freezing a cryoprecipitate after producing the cryoprecipitate (e.g., after the initial plasma freezing step, after the precipitation step). Advantageously, this allows the cryoprecipitate to be stored for later use. In some embodiments, cryoprecipitate may be stored at about −18° C. or lower (e.g., according to AABB standards).

After freezing (and optional frozen storage), cryoprecipitate may be thawed. Methods for thawing frozen cryoprecipitate are well known in the art. As a non-limiting example, cryoprecipitate may be thawed in a plasma thawer (e.g., those commercially available from Helmer Scientific). In some embodiments, cryoprecipitate may be thawed at about 35° C. In some embodiments, cryoprecipitate may be thawed for approximately 5-10 minutes. In some embodiments, after thawing, the cryoprecipitate may be mixed, e.g., by agitation. In some embodiments, cryoprecipitate may be allowed to thaw for two or more intervals, which may optionally be separated by one or more mixing steps. In some embodiments, cryoprecipitate may be thawed for approximately 5-10 minutes, mixed, and allowed to continue thawing for approximately 5-10 minutes.

For each of the parameters set forth in the methods provided herein, techniques for determination or measurement of the parameters are well known in the art.

Cryoprecipitate Compositions

Described infra are various exemplary parameters and properties that may characterize a cryoprecipitate (or a composition comprising a cryoprecipitate) of the present disclosure. It will be appreciated by one of skill in the art that these exemplary characteristics and embodiments may be combined in any number or combination, unless otherwise indicated by context. These exemplary characteristics and embodiments may be combined with any of the other embodiments or aspects described elsewhere herein in any number or combination, unless otherwise indicated by context.

Certain aspects of the present disclosure relate to compositions comprising a cryoprecipitate suitable for infusion into a subject. As disclosed herein, these compositions are suitable for infusion into a subject for a longer duration after thawing (e.g., thawing after frozen cryoprecipitate storage) than is currently prescribed by existing guidelines (e.g., the compositions have an extended period before expiry after thawing). Such compositions may find use, inter alia, in treatments (e.g., infusions) related to control of bleeding associated with fibrinogen deficiency, treating Factor XIII deficiency, treating von Willebrand disease, maintenance of hemostasis, treating disseminated intravascular coagulation (DIC) or high volume hemorrhage, and/or making fibrin sealant.

In some embodiments, a cryoprecipitate (or a composition comprising a cryoprecipitate) is suitable for infusion into a subject at least 6 hours, at least 12 hours, at least 24 hours, at least 36 hours, at least 48 hours, at least 60 hours, at least 72 hours, at least 84 hours, at least 96 hours, at least 108 hours, at least 120 hours, at least 132 hours, at least 144 hours, at least 156 hours, or at least 168 hours after thawing. In some embodiments, a cryoprecipitate is suitable for infusion into a subject within 6 hours, within 12 hours, within 24 hours, within 36 hours, within 48 hours, within 60 hours, within 72 hours, within 84 hours, within 96 hours, within 108 hours, within 120 hours, within 132 hours, within 144 hours, within 156 hours, or within 168 hours after thawing. In some embodiments, the cryoprecipitate is suitable for infusion into a subject for a number of hours after thawing that is less than about any of the following numbers of hours: 168, 156, 144, 132, 120, 108, 96, 84, 72, 60, 48, 36, 24, or 12. In some embodiments, the cryoprecipitate is suitable for infusion into a subject for a number of hours after thawing (e.g., after thawing and resuspension of the cryoprecipitate) that is greater than about any of the following numbers of hours: 0, 0.25, 0.5, 1, 2, 3, 4, 5, 6, 12, 24, 36, 48, 60, 72, 84, 96, 108, 120, 132, 144, or 156. That is, the number of hours after thawing for which the cryoprecipitate is suitable for infusion into a subject may be any number of hours within a range having an upper limit of 168, 156, 144, 132, 120, 108, 96, 84, 72, 60, 48, 36, 24, or 12 hours and an independently selected lower limit of 0, 0.25, 0.5, 1, 2, 3, 4, 5, 6, 12, 24, 36, 48, 60, 72, 84, 96, 108, 120, 132, 144, or 156 hours, wherein the upper limit is greater than the lower limit. In some embodiments, the cryoprecipitate is suitable for infusion into a subject immediately after thawing and resuspension of the cryoprecipitate (e.g., 0 hours after thawing). In some embodiments, the cryoprecipitate may be suitable for infusion into a subject for about 0 to about 168 hours, about 0 to about 144 hours, about 0 to about 120 hours after thawing, about 0 to about 96 hours after thawing, about 0 to about 72 hours after thawing, or about 0 to about 48 hours after thawing. In some embodiments, the cryoprecipitate may be suitable for infusion into a subject for about 6 to about 168 hours, about 6 to about 144 hours, or about 6 to about 120 hours after thawing. In some embodiments, the cryoprecipitate may be suitable for infusion into a subject for about 12 to about 168 hours, about 12 to about 144 hours, or about 12 to about 120 hours after thawing. In some embodiments, the cryoprecipitate may be suitable for infusion into a subject for about 24 to about 168 hours, about 24 to about 144 hours, or about 24 to about 120 hours after thawing. In some embodiments, the cryoprecipitate may be suitable for infusion into a subject for about 36 to about 168 hours, about 36 to about 144 hours, or about 36 to about 120 hours after thawing. In some embodiments, the cryoprecipitate may be suitable for infusion into a subject for about 48 to about 168 hours, about 48 to about 144 hours, or about 48 to about 120 hours after thawing.

In some embodiments, a cryoprecipitate (or a composition comprising a cryoprecipitate) is suitable for infusion into a subject at least 1 day, at least 2 days, at least 3 days, at least 4 days, at least 5 days, at least 6 days, or at least 7 days after thawing. In some embodiments, the cryoprecipitate is suitable for infusion into a subject within 1 day, within 2 days, within 3 days, within 4 days, within 5 days, within 6 days, or within 7 days after thawing. In some embodiments, a cryoprecipitate is suitable for infusion into a subject for a number of days after thawing that is less than about any of the following numbers of days: 7, 6, 5, 4, 3, or 2. In some embodiments, the cryoprecipitate is suitable for infusion into a subject for a number of days after thawing (e.g., after thawing and resuspension of the cryoprecipitate) that is greater than about any of the following numbers of days: 0, 1, 2, 3, 4, 5, or 6. In some embodiments, the cryoprecipitate is suitable for infusion into a subject immediately after thawing and resuspension of the cryoprecipitate (e.g., 0 days after thawing). That is, the number of days after thawing for which the cryoprecipitate is suitable for infusion into a subject may be any number of days within a range having an upper limit of 7, 6, 5, 4, 3, or 2 days and an independently selected lower limit of 0, 1, 2, 3, 4, 5, or 6 days, wherein the upper limit is greater than the lower limit. In some embodiments, the cryoprecipitate may be suitable for infusion into a subject for about 0 to about 7 days, about 0 to about 6 days, about 0 to about 5 days, about 0 to about 4 days, about 0 to about 3 days, or about 0 to about 2 days after thawing. In some embodiments, the cryoprecipitate may be suitable for infusion into a subject for about 1 to about 7 days, about 1 to about 6 days, or about 1 to about 5 days after thawing. In some embodiments, the cryoprecipitate may be suitable for infusion into a subject for about 2 to about 7 days, about 2 to about 6 days, or about 2 to about 5 days after thawing.

In some embodiments, a cryoprecipitate (or a composition comprising a cryoprecipitate) is stored at room temperature after thawing, e.g., for the interval between thawing and use (e.g., in an infusion). In some embodiments, a cryoprecipitate (or a composition comprising a cryoprecipitate) is stored at between about 2° C. and about 25° C. after thawing, e.g., for the interval between thawing and use (e.g., in an infusion). In some embodiments, a cryoprecipitate (or a composition comprising a cryoprecipitate) is stored at between about 20° C. and about 24° C. after thawing, e.g., for the interval between thawing and use (e.g., in an infusion). In some embodiments, a cryoprecipitate (or a composition comprising a cryoprecipitate) is stored at about 22° C. after thawing, e.g., for the interval between thawing and use. In some embodiments, a cryoprecipitate (or a composition comprising a cryoprecipitate) is stored at 2° C. and about 6° C. after thawing, e.g., for the interval between thawing and use (e.g., in an infusion). In some embodiments, a cryoprecipitate (or a composition comprising a cryoprecipitate) is stored after thawing, e.g., for the interval between thawing and use (e.g., in an infusion) according to standards set by AABB, the American Red Cross or another accrediting, regulatory, or standard-setting agency.

It is well known in the art that different types of blood donations containing plasma may have different associated volumes. The volume of plasma obtained from a whole blood donation may vary, depending upon, for example, the volume of whole blood collected, the size of the collection bag (e.g., 450 mL, 500 mL), the donor percent hematocrit and processing conditions (e.g., centrifugation conditions). For example, in certain embodiments, a whole blood donation typically yields an approximately 180-250 mL (e.g., approximately 200 mL) unit of plasma (e.g., whole blood derived plasma), whereas the volume of plasma from a single apheresis donation or sample (e.g., apheresis collected plasma) may yield from about 200 mL up to approximately 700-800 mL, depending on a variety of factors including donor size (e.g., body weight). In some embodiments, a cryoprecipitate (or a composition comprising a cryoprecipitate) of the present disclosure may be obtained or prepared from about 180 mL or 200 mL to about 250 mL or 300 mL or 325 mL of plasma. For example, the cryoprecipitate may be obtained from one approximately 200 mL unit (e.g., AABB defined unit, AABB unit volume) volume of plasma, such as from a single whole blood donation. In other embodiments, a cryoprecipitate (or a composition comprising a cryoprecipitate) of the present disclosure may be obtained from at least about 300 mL, at least about 400 mL, at least about 500 mL, or at least about 600 mL or more of plasma. In other embodiments, a cryoprecipitate (or a composition comprising a cryoprecipitate) of the present disclosure may be obtained from at least about 550 mL and less than 650 mL of plasma. In some embodiments, a cryoprecipitate (or a composition comprising a cryoprecipitate) of the present disclosure may be obtained from at least about 570 mL and less than about 620 mL of plasma. In some embodiments, a cryoprecipitate (or a composition comprising a cryoprecipitate) of the present disclosure may be obtained from at least about 600 mL and less than about 650 mL of plasma. In certain embodiments, a cryoprecipitate (or a composition comprising a cryoprecipitate) of the present disclosure may be obtained from about 600 mL of plasma. For example, a cryoprecipitate may be obtained from pooling multiple AABB unit volumes of plasma (e.g., to yield 550-650 mL), a single apheresis sample (e.g., having 550-650 mL or more), or from pooling multiple cryoprecipitates obtained from different samples of plasma.

As such, in some embodiments, a cryoprecipitate (or a composition comprising a cryoprecipitate) of the present disclosure may contain cryoprecipitate obtained or prepared from one donor. In other embodiments, a cryoprecipitate (or a composition comprising a cryoprecipitate) of the present disclosure may contain cryoprecipitate obtained or prepared from more than one donor (e.g., prepared from more than one plasma donation, prepared from more than one plasma unit). In some embodiments, a cryoprecipitate (or a composition comprising a cryoprecipitate) of the present disclosure may contain cryoprecipitate obtained or prepared from 2-12 donors. In some embodiments, a cryoprecipitate (or a composition comprising a cryoprecipitate) of the present disclosure may contain cryoprecipitate prepared from plasma obtained from 2-6 donors. For example, in some embodiments, a cryoprecipitate (or a composition comprising a cryoprecipitate) of the present disclosure may contain cryoprecipitate prepared from plasma obtained from 1, 2, 3, 4, 5, or 6 donors. In some embodiments, a cryoprecipitate (or a composition comprising a cryoprecipitate) of the present disclosure may contain cryoprecipitate obtained or prepared from 7-12 donors. For example, in some embodiments, a cryoprecipitate (or a composition comprising a cryoprecipitate) of the present disclosure may contain cryoprecipitate prepared from plasma obtained from 7, 8, 9, 10, 11 or 12 donors.

In some embodiments, a cryoprecipitate composition of the present disclosure may contain more than one cryoprecipitate (e.g., individual cryoprecipitate preparations). For example, in some embodiments, a cryoprecipitate composition of the present disclosure may contain a first cryoprecipitate obtained from pathogen-inactivated plasma and a second cryoprecipitate obtained from pathogen-inactivated plasma. In some embodiments, a cryoprecipitate composition of the present disclosure may contain a first cryoprecipitate obtained from 2 units of pathogen-inactivated plasma and a second cryoprecipitate obtained from 2 units of pathogen-inactivated plasma. In some embodiments, a cryoprecipitate composition of the present disclosure may contain a first cryoprecipitate obtained from 3 units of pathogen-inactivated plasma and a second cryoprecipitate obtained from 3 units of pathogen-inactivated plasma. In some embodiments, the first and the second cryoprecipitates are combined prior to re-freezing for storage. In some embodiments, the first and the second cryoprecipitates are combined prior to use (e.g., in an infusion), and/or prior to storage at room temperature or under refrigeration. In some embodiments, a cryoprecipitate composition of the present disclosure may contain pathogen-inactivated plasma pooled from at least 3, at least 4, at least 5, or at least 6 units of pathogen-inactivated plasma. In some embodiments, a cryoprecipitate composition of the present disclosure may contain pathogen-inactivated plasma pooled from at least 7, at least 8, at least 9, at least 10, at least 11, or at least 12 units of pathogen-inactivated plasma. In some embodiments, a cryoprecipitate composition of the present disclosure may contain pathogen-inactivated plasma pooled from at least 7, at least 8, at least 9, at least 10, at least 11, or at least 12 units of pathogen-inactivated plasma In certain embodiments, a cryoprecipitate composition of the present disclosure may contain pathogen-inactivated plasma pooled from at least 3 units of pathogen-inactivated plasma. In certain embodiments, a cryoprecipitate composition of the present disclosure may contain pathogen-inactivated plasma pooled from at least 6 units of pathogen-inactivated plasma.

Figure 7:
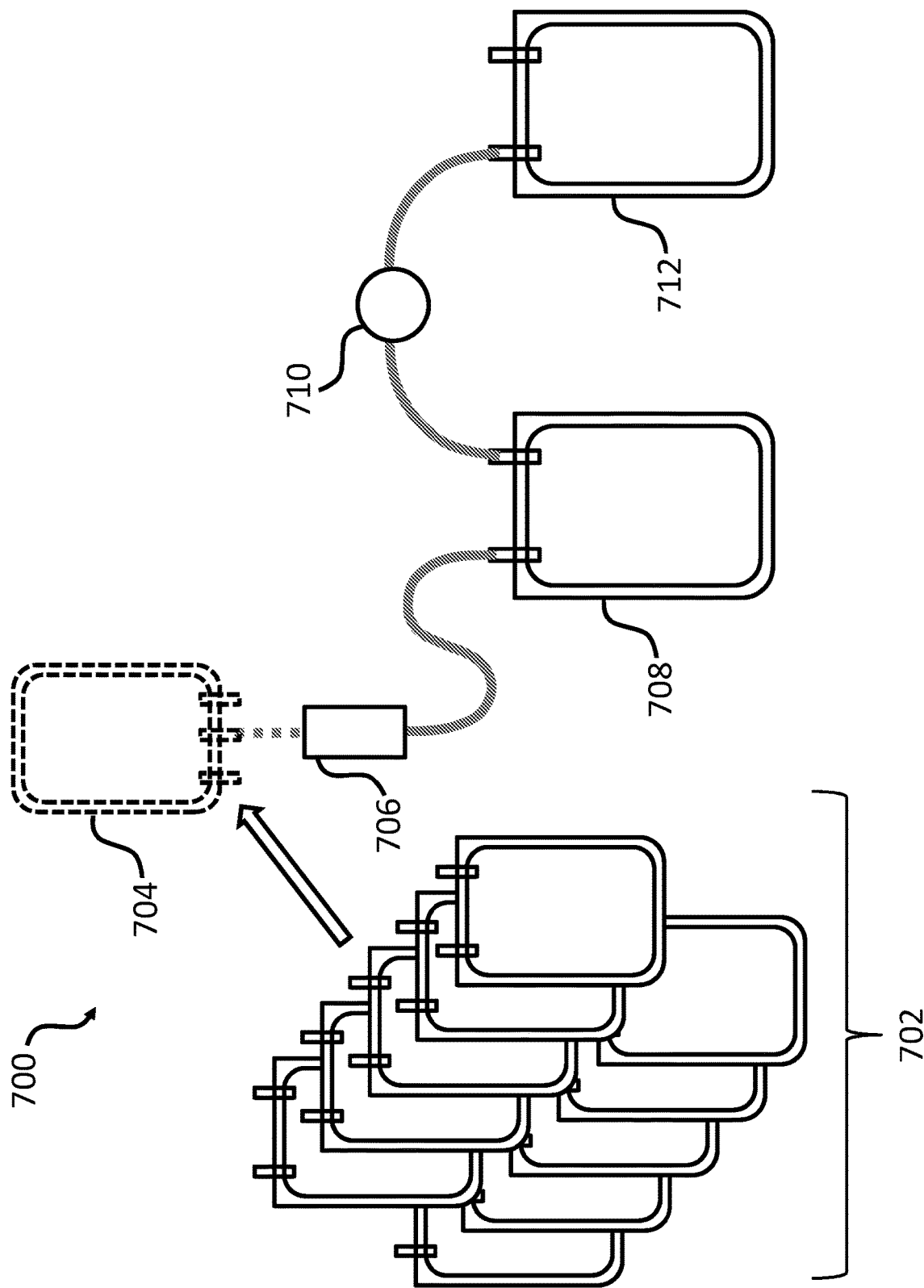
FIG. 7 shows an exemplary processing kit in accordance with some embodiments. Dotted components are optional.

In some embodiments, a cryoprecipitate composition of the present disclosure may be generated from plasma that has not been subject to pathogen inactivation, then the cryoprecipitate itself may be subjected to pathogen-inactivation (and, optionally, frozen for storage after pathogen inactivation). In some embodiments, the pathogen inactivated cryoprecipitate may be stored at 2-25° C. (e.g., 2-6° C., 20-24° C.) until use for infusion. In some embodiments, a cryoprecipitate may be prepared from plasma and subsequently subjected to pathogen inactivation. In some embodiments, the plasma has not been subject to pathogen inactivation. In some embodiments, multiple cryoprecipitate preparations made from plasma (e.g., plasma that has not been subject to pathogen inactivation) may be pooled together, then subject to pathogen inactivation (see, e.g., 700, 702, and 704 as shown in FIG. 7). Advantageously, this enables the pathogen inactivation of a large volume of cryoprecipitate (e.g., a pooled cryoprecipitate composition) in one step and/or one container. In other embodiments, multiple cryoprecipitate preparations prepared from plasma (e.g., plasma that has not been subject to pathogen inactivation) may be subject to pathogen inactivation, then pooled together. In some embodiments, the pathogen-inactivated cryoprecipitate (e.g., pooled cryoprecipitate) is frozen for storage. Any desired volume of cryoprecipitate may be subject to pathogen inactivation and optionally pooled (e.g., before or after pathogen inactivation). For example, in some embodiments, at least two, at least three, at least four, at least five, at least six, at least seven, at least eight, at least nine, at least 10, at least 11, or at least 12 preparations or units of cryoprecipitate may be pooled together, e.g., before or after pathogen inactivation. In some embodiments, the cryoprecipitate is prepared from at least about 550 mL and less than about 650 mL of plasma. In some embodiments, the cryoprecipitate is prepared by pooling two or more cryoprecipitate units (e.g., before or after pathogen inactivation), each cryoprecipitate unit having been prepared from at least about 550 mL and less than about 650 mL of plasma. In some embodiments, the cryoprecipitate is prepared by pooling two or more, three or more, four or more, five or more, six or more, seven or more, eight or more, nine or more, ten or more, eleven or more, or twelve or more cryoprecipitate units (e.g., before or after pathogen inactivation), each cryoprecipitate unit having been prepared from at least about 150 mL and less than about 250 mL of plasma, e.g., about 200 mL of plasma. In some embodiments, the cryoprecipitate is prepared by pooling two or more, three or more, four or more, five or more, six or more, seven or more, eight or more, nine or more, ten or more, eleven or more, or twelve or more cryoprecipitate units (e.g., before or after pathogen inactivation), each cryoprecipitate unit having been prepared from a whole blood derived plasma unit.

In some embodiments, a cryoprecipitate composition of the present disclosure may contain a first cryoprecipitate obtained or prepared from at least about 550 mL and less than 650 mL of pathogen-inactivated plasma, and a second cryoprecipitate obtained or prepared from at least about 550 mL and less than 650 mL of pathogen-inactivated plasma. In some embodiments, a cryoprecipitate composition of the present disclosure may contain a first cryoprecipitate obtained or prepared from at least about 570 mL and less than 620 mL of pathogen-inactivated plasma, and a second cryoprecipitate obtained or prepared from at least about 570 mL and less than 620 mL of pathogen-inactivated plasma. In some embodiments, a cryoprecipitate composition of the present disclosure may contain a first cryoprecipitate obtained or prepared from at least about 600 mL and less than 650 mL of pathogen-inactivated plasma, and a second cryoprecipitate obtained or prepared from at least about 600 mL and less than 650 mL of pathogen-inactivated plasma. In certain embodiments, a cryoprecipitate composition of the present disclosure may contain a first cryoprecipitate obtained or prepared from about 600 mL of pathogen-inactivated plasma, and a second cryoprecipitate obtained or prepared from about 600 mL of pathogen-inactivated plasma. In some embodiments, a cryoprecipitate composition of the present disclosure may contain a first cryoprecipitate obtained or prepared from at least about 150 mL and less than about 250 mL of pathogen-inactivated plasma, and a second cryoprecipitate obtained or prepared from at least about 150 mL and less than about 250 mL of pathogen-inactivated plasma. Individual cryoprecipitates may be combined or pooled after cryoprecipitate production but prior to use and/or re-freezing for storage, and/or individual plasma samples may be combined or pooled prior to cryoprecipitate production.

In some embodiments, a cryoprecipitate may be part of a composition containing plasma at a specific volume. For example, cryoprecipitate is typically resuspended in a volume of plasma remaining after cryoprecipitate production (e.g., some amount of leftover plasma after production of the cryoprecipitate). This volume may then be used or frozen for storage as described herein.

In some embodiments, a composition comprising a cryoprecipitate of the present disclosure includes plasma of a volume that is less than about any of the following volumes (in mL): 150, 140, 130, 120, 110, 100, 90, 80, 76, 75, 74, 73, 72, 71, 70, 69, 68, 67, 66, 65, 64, 63, 62, 61, 60, 59, 58, 57, 56, 55, 54, 53, 52, 51, 50, 45, 40, 35, 30, 25, 20, 19, 18, 17, 16, 15, 14, 13, 12, 11, 10, 9, 8, 7, or 6. In some embodiments, a composition comprising a cryoprecipitate of the present disclosure includes plasma of a volume that is greater than about any of the following volumes (in mL): 5, 6, 7, 8, 9, 10, 11, 12, 13, 14, 15, 16, 17, 18, 19, 20, 25, 30, 35, 40, 45, 50, 51, 52, 53, 54, 55, 56, 57, 58, 59, or 60. That is, the composition comprising a cryoprecipitate of the present disclosure may include plasma of any volume within a range having an upper limit of 150, 140, 130, 120, 110, 100, 90, 80, 76, 75, 74, 73, 72, 71, 70, 69, 68, 67, 66, 65, 64, 63, 62, 61, 60, 59, 58, 57, 56, 55, 54, 53, 52, 51, 50, 45, 40, 35, 30, 25, 20, 19, 18, 17, 16, 15, 14, 13, 12, 11, 10, 9, 8, 7, or 6 mL and an independently selected lower limit of 5, 6, 7, 8, 9, 10, 11, 12, 13, 14, 15, 16, 17, 18, 19, 20, 25, 30, 35, 40, 45, 50, 51, 52, 53, 54, 55, 56, 57, 58, 59, or 60 mL, wherein the upper limit is greater than the lower limit. In some embodiments, a composition comprising a cryoprecipitate of the present disclosure includes between about 5 mL and about 25 mL of plasma, about 5 mL and about 20 mL of plasma, about 10 mL to about 20 mL of plasma, or about 15 mL to about 20 mL of plasma. In other embodiments, a composition comprising a cryoprecipitate of the present disclosure includes between about 30 mL and about 150 mL, between about 75 mL and about 150 mL, between about 30 mL and about 75 mL of plasma, between about 40 mL and about 75 mL of plasma, between about 50 mL and about 75 mL of plasma, between about 60 mL and about 75 mL of plasma, between about 50 mL and about 70 mL of plasma, between about 50 mL and about 65 mL of plasma, between about 50 mL and about 60 mL of plasma, between about 55 mL to about 70 mL of plasma, between about 55 mL to about 65 mL of plasma, between about 55 mL to about 60 mL of plasma, or between about 60 mL and about 70 mL of plasma. In other embodiments, a composition comprising a cryoprecipitate of the present disclosure includes greater than about 1 mL and less than or equal to about 75 mL of plasma, or greater than about 5 mL and less than or equal to about 75 mL of plasma. In some embodiments, the aforementioned plasma volumes comprise the plasma volumes following resuspension of the cryoprecipitate.

In some embodiments, the specific volume of plasma may depend upon the amount of cryoprecipitate (e.g., depend upon the amount of plasma used to produce the cryoprecipitate). In some embodiments, for cryoprecipitate obtained from one AABB unit volume of plasma (e.g., 200 mL), the volume of plasma in the composition may be from about 5 mL to about 25 mL, from about 5 mL to about 20 mL, from about 10 mL to about 20 mL or from about 15 mL to about 20 mL, or any other comparable range as described above. In some embodiments, for cryoprecipitate obtained from more than one AABB unit volume of plasma (e.g., 550-650 mL), or for a pool of multiple cryoprecipitate preparations (e.g., each having been obtained from about 200 mL of plasma), the volume of plasma in the composition may be from about 15 mL to about 75 mL, from about 15 mL to about 60 mL, from about 30 mL to about 75 mL, from about 30 mL to about 60 mL, from about 30 mL to about 40 mL, 40 mL to about 70 mL, from about 45 mL to about 65 mL, from about 50 mL to about 60 mL, or any other comparable range as described above. In certain embodiments, the volume of plasma in the composition may be less than or equal to about 75 mL. In some embodiments, for cryoprecipitate obtained by combining two or more cryoprecipitate preparations, each made from more than one AABB unit volume of plasma (e.g., each being 550-650 mL, for an aggregate total of 1100-1300 mL), the volume of plasma in the composition may be from about 30 mL to about 150 mL, from about 30 mL to about 120 mL, from about 60 mL to about 120 mL, from about 90 mL to about 120 mL, from about 50 mL to about 100 mL, from about 60 mL to about 90 mL, from about 60 mL to about 75 mL from about 50 mL to about 75 mL, or about 75 mL. In certain embodiments, the volume of plasma in the composition obtained by combining two or more cryoprecipitate preparations may be less than or equal to about 75 mL.

As described herein and well known in the art, a cryoprecipitate or cryoprecipitate composition of the present disclosure may be tested for the amount and/or activity of one or more components, including without limitation fibrinogen, Factor VIII, Factor XIII, and/or vWF. In some embodiments, this testing refers to a measurement taken from an individual sample. In other embodiments, it refers to an average based on measurements taken from multiple samples (e.g., random samples of sufficient number to provide a statistically significant sampling). Often, multiple cryoprecipitate compositions (units) may be thawed during a particular period of production (e.g., 1 month of production) and tested to yield a measurement that is held to be representative of those units that were not tested. The un-tested or non-tested samples may then be used in a treatment, such as an infusion. Therefore, "testing" as used herein refers to testing a particular cryoprecipitate composition, or it refers to testing other cryoprecipitate compositions in a defined cross-section of cryoprecipitate compositions (e.g., in which a measurement of one or more individual samples or average of measurements is held to be representative of a cryoprecipitate composition that was not tested). In some embodiments, a cryoprecipitate or cryoprecipitate composition of the present disclosure may be tested prior to re-freezing and/or storage. In some embodiments, a cryoprecipitate or cryoprecipitate composition of the present disclosure may be tested after thawing. In some embodiments, a cryoprecipitate or cryoprecipitate composition of the present disclosure may be tested before use, e.g., in an infusion. As used herein, the terms "testing" and "determining," including grammatical derivatives thereof, may be used interchangeably. Therefore, "determining" as used herein refers to determining an amount of an analyte of interest (including without limitation fibrinogen, Factor VIII, Factor XIII, and/or vWF) in a particular cryoprecipitate composition, or it refers to determining an amount of the analyte of interest in other cryoprecipitate compositions in a defined cross-section of cryoprecipitate compositions (e.g., in which a measurement of one or more individual samples or average of measurements is held to be representative of a cryoprecipitate composition that was not tested, such as a plurality of cryoprecipitate compositions produced by the same methods and/or produced in the same location or general time frame, e.g., within 30 days).

It will be appreciated by one of skill in the art that a cryoprecipitate or cryoprecipitate composition of the present disclosure may be tested at one or more times (e.g., after thawing) for the amount and/or activity of one or more components, including without limitation fibrinogen, Factor VIII, Factor XIII, and/or vWF. For example, a cryoprecipitate or cryoprecipitate composition of the present disclosure may be tested shortly after thawing (e.g., within 2 hours of thawing, within 6 hours of thawing), and/or a cryoprecipitate or cryoprecipitate composition of the present disclosure may be tested at or shortly preceding the time of infusion or the time of expiry post-thaw, which, in some embodiments described herein, may occur up to about 1 day, up to about 2 days, up to about 3 days, up to about 4 days, up to about 5 days, or up to about 7 days after thawing. It is to be understood that any of the exemplary amounts of cryoprecipitate or cryoprecipitate composition components described herein (e.g., fibrinogen, Factor VIII, Factor XIII, and/or vWF) refers to an amount tested or determined shortly after thawing (e.g., within 2 hours of thawing, within 6 hours of thawing) or an amount tested at or shortly preceding the time of infusion or the time of expiry post-thaw (e.g., up to about 1 day, up to about 2 days, up to about 3 days, up to about 4 days, up to about 5 days, or up to about 7 days after thawing).

In some embodiments, a cryoprecipitate or cryoprecipitate composition of the present disclosure may be tested for Factor VIII. Various assays for measuring Factor VIII are known in the art, including without limitation the chromogenic assay, the one-stage clotting or activated partial thromboplastin time (APTT) assay, and the two-stage clotting or activated partial thromboplastin time (APTT) assay. Without wishing to be bound to theory, it is thought that cryoprecipitate having less than a particular amount of Factor VIII, e.g., an AABB standard for Factor VIII such as 80 IU per unit, may advantageously be used for the treatment of many conditions, including without limitation control of bleeding associated with fibrinogen deficiency, treating Factor XIII deficiency, treating von Willebrand disease, maintenance of hemostasis, treating disseminated intravascular coagulation (DIC) or high volume hemorrhage, and/or making fibrin sealant. Advantageously, this cryoprecipitate, preferably containing pathogen inactivated plasma, may be suitable for infusion after a greater duration post-thawing than, e.g., recommended by current AABB standards (such as less than 6 hours).

In some embodiments, a cryoprecipitate or cryoprecipitate composition of the present disclosure contains less than about 80, less than about 75, less than about 70, less than about 65, less than about 60, less than about 55, less than about 50, less than about 45, less than about 40, less than about 35, less than about 30, less than about 25, less than about 20, less than about 15, or less than about 10 IU of Factor VIII per unit of cryoprecipitate (e.g., per unit of cryoprecipitate derived from about 200 mL of plasma). In some embodiments, a composition comprising a cryoprecipitate of the present disclosure includes Factor VIII at an amount that is less than about any of the following amounts (in IU, either absolute or per unit of cryoprecipitate): 480, 450, 400, 350, 300, 250, 225, 200, 175, 150, 125, 100, 95, 90, 85, 80, 75, 70, 65, 60, 55, 50, 45, 40, 35, 30, 25, 20, or 15. In some embodiments, a composition comprising a cryoprecipitate of the present disclosure includes Factor VIII at an amount that is greater than about any of the following amounts (in IU, either absolute or per unit of cryoprecipitate): 10, 15, 20, 25, 30, 35, 40, 45, 50, 55, 60, 65, 70, 75, 80, 85, 90, 95, 100, 125, 150, 175, 200, or 225. That is, the composition comprising a cryoprecipitate of the present disclosure may include Factor VIII at any amount within a range having an upper limit of 480, 450, 400, 350, 300, 250, 225, 200, 175, 150, 125, 100, 95, 90, 85, 80, 75, 70, 65, 60, 55, 50, 45, 40, 35, 30, 25, 20, or 15 IU and an independently selected lower limit of 10, 15, 20, 25, 30, 35, 40, 45, 50, 55, 60, 65, 70, 75, 80, 85, 90, 95, 100, 125, 150, 175, 200, or 225 IU, wherein the upper limit is greater than the lower limit. In other embodiments, a cryoprecipitate or cryoprecipitate composition of the present disclosure contains at least 80 IU of Factor VIII per unit (e.g., 200 mL unit, per unit of cryoprecipitate derived from about 200 mL of plasma) of cryoprecipitate. In some embodiments, a cryoprecipitate or cryoprecipitate composition of the present disclosure contains at least 80 IU of Factor VIII. In some embodiments, a cryoprecipitate or cryoprecipitate composition of the present disclosure contains 80-100 IU of Factor VIII per unit (e.g., 200 mL unit, per unit of cryoprecipitate derived from about 200 mL of plasma) of cryoprecipitate. Factor VIII content of a cryoprecipitate or cryoprecipitate composition of the present disclosure may be expressed per unit volume (e.g., per unit of cryoprecipitate derived from about 200 mL of plasma), or as an absolute amount. In some embodiments, a cryoprecipitate or cryoprecipitate composition of the present disclosure contains less than about 80 IU or less than about 50 IU of Factor VIII per unit (e.g., 200 mL unit, per unit of cryoprecipitate derived from about 200 mL of plasma) of cryoprecipitate at the time of thawing (e.g., within about 1 hour or within about 2 hours of thawing). In some embodiments, a cryoprecipitate or cryoprecipitate composition of the present disclosure contains less than about 80 IU or less than about 50 IU of Factor VIII per unit of cryoprecipitate at or shortly preceding the infusion (e.g., up to about 1 day, up to about 3 days, up to about 5 days, or up to about 7 days after thawing). In some embodiments, a cryoprecipitate or cryoprecipitate composition of the present disclosure contains less than about 80 IU of Factor VIII at or shortly preceding the infusion (e.g., up to about 1 day, up to about 3 days, up to about 5 days, or up to about 7 days after thawing). In some embodiments, a cryoprecipitate or cryoprecipitate composition of the present disclosure contains at least about 80 IU of Factor VIII at or shortly preceding the infusion (e.g., up to about 1 day, up to about 3 days, up to about 5 days, or up to about 7 days after thawing). In some embodiments, a cryoprecipitate or cryoprecipitate composition of the present disclosure contains 80-100 IU of Factor VIII at or shortly preceding the infusion (e.g., up to about 1 day, up to about 3 days, up to about 5 days, or up to about 7 days after thawing). In some embodiments, a cryoprecipitate or cryoprecipitate composition of the present disclosure contains comprises about 80-240 IU (e.g., total IU) of Factor VIII at or shortly preceding the infusion (e.g., up to about 1 day, up to about 3 days, up to about 5 days, or up to about 7 days after thawing). In some embodiments, a cryoprecipitate or cryoprecipitate composition of the present disclosure contains comprises about 80-480 IU (e.g., total IU) of Factor VIII at or shortly preceding the infusion (e.g., up to about 1 day, up to about 3 days, up to about 5 days, or up to about 7 days after thawing). In some embodiments, an amount of factor VIII is determined from cryoprecipitate sampled within about 2 hours, within about 6 hours, within about 1 day, within about 2 days, within about 3 days, within about 4 days, or within about 5 days after thawing.

In some embodiments, a composition contains cryoprecipitate prepared from at least about 550 mL and less than about 650 mL of pathogen-inactivated plasma. In some embodiments, a composition contains two or more cryoprecipitates, each of the two or more cryoprecipitates prepared from at least about 150 mL and less than about 250 mL of plasma, e.g., about 200 mL of plasma. In some embodiments, cryoprecipitate prepared from at least about 550 mL and less than about 650 mL of pathogen-inactivated plasma contains between about 80 and about 200 IU of Factor VIII, e.g., at or shortly preceding the infusion (e.g., up to about 1 day, up to about 3 days, up to about 5 days, or up to about 7 days after thawing). For example, in some embodiments, cryoprecipitate prepared from at least about 550 mL and less than about 650 mL of pathogen-inactivated plasma contains between about 80 and about 200 IU of Factor VIII at the time of thawing (e.g., within about 1 hour or within about 2 hours of thawing). In some embodiments, cryoprecipitate prepared from at least about 550 mL and less than about 650 mL of pathogen-inactivated plasma contains between about 80 and about 200 IU of Factor VIII as determined within about 2 hours, within about 6 hours, within about 1 day, within about 2 days, within about 3 days, within about 4 days, or within about 5 days after thawing.

In some embodiments, a composition contains a first cryoprecipitate prepared from at least about 550 mL and less than about 650 mL of pathogen-inactivated plasma and a second cryoprecipitate prepared from at least about 550 mL and less than about 650 mL of pathogen-inactivated plasma. In some embodiments, a composition containing two cryoprecipitates, each prepared from at least about 550 mL and less than about 650 mL of pathogen-inactivated plasma, contains between about 160 and about 400 IU of Factor VIII, e.g., at or shortly preceding the infusion (e.g., up to about 1 day, up to about 3 days, up to about 5 days, or up to about 7 days after thawing). For example, in some embodiments, a composition containing two cryoprecipitates, each prepared from at least about 550 mL and less than about 650 mL of pathogen-inactivated plasma, contains between about 160 and about 400 IU of Factor VIII at the time of thawing (e.g., within about 1 hour or within about 2 hours of thawing). In some embodiments, a composition containing two cryoprecipitates, each prepared from at least about 550 mL and less than about 650 mL of pathogen-inactivated plasma, contains between about 160 and about 400 IU of Factor VIII as determined within about 2 hours, within about 6 hours, within about 1 day, within about 2 days, within about 3 days, within about 4 days, or within about 5 days after thawing.

In some embodiments, a cryoprecipitate or cryoprecipitate composition of the present disclosure may be tested for fibrinogen. Various assays for measuring fibrinogen are known in the art, including without limitation the Clauss method, prothrombin time-derived assays, immunological assays, and gravimetric assays. In some embodiments, a cryoprecipitate or cryoprecipitate composition of the present disclosure contains an amount of fibrinogen meeting AABB standards. In some embodiments, a cryoprecipitate or cryoprecipitate composition of the present disclosure contains at least about 100, at least about 150, at least about 200, at least about 250, or at least about 300 mg of fibrinogen per unit of cryoprecipitate (e.g., per unit of cryoprecipitate derived from about 200 mL of plasma). In some embodiments, a composition comprising a cryoprecipitate of the present disclosure includes fibrinogen at an amount that is less than about any of the following amounts (in mg, either absolute or per unit of cryoprecipitate): 2500, 2000, 1800, 1500, 1200, 750, 700, 650, 600, 550, 500, 450, 400, 350, 300, 250, 200, or 150. In some embodiments, a composition comprising a cryoprecipitate of the present disclosure includes fibrinogen at an amount that is greater than about any of the following amounts (in mg, either absolute or per unit of cryoprecipitate): 140, 150, 200, 250, 300, 350, 400, 450, 500, 550, 600, 650, 700, 750, 800, 850, 900, 1000, 1100, 1200, or 1500. That is, the composition comprising a cryoprecipitate of the present disclosure may include fibrinogen at any amount within a range having an upper limit of 2500, 2000, 1800, 1500, 1200, 750, 700, 650, 600, 550, 500, 450, 400, 350, 300, 250, 200, or 150 mg and an independently selected lower limit of 140, 150, 200, 250, 300, 350, 400, 450, 500, 550, 600, 650, 700, 750, 800, 850, 900, 1000, 1100, 1200, or 1500 mg, wherein the upper limit is greater than the lower limit. In some embodiments, a cryoprecipitate or cryoprecipitate composition of the present disclosure contains at least about 250 mg or at least about 150 mg of fibrinogen per unit of cryoprecipitate (e.g., per unit of cryoprecipitate derived from about 200 mL of plasma) at the time of thawing (e.g., within about 1 hour or within about 2 hours of thawing). In some embodiments, a cryoprecipitate or cryoprecipitate composition of the present disclosure contains at least about 250 mg or at least about 150 mg of fibrinogen per unit of cryoprecipitate (e.g., per unit of cryoprecipitate derived from about 200 mL of plasma) at or shortly preceding the infusion (e.g., up to about 1 day, up to about 3 days, up to about 5 days, or up to about 7 days after thawing). In some embodiments, a cryoprecipitate or cryoprecipitate composition of the present disclosure contains at least about 250 mg or at least about 150 mg of fibrinogen at the time of thawing (e.g., within about 1 hour or within about 2 hours of thawing). In some embodiments, a cryoprecipitate or cryoprecipitate composition of the present disclosure contains at least about 750 mg of fibrinogen (e.g., total mg of fibrinogen) at or shortly preceding the infusion (e.g., up to about 1 day, up to about 3 days, up to about 5 days, or up to about 7 days after thawing). In some embodiments, a cryoprecipitate or cryoprecipitate composition of the present disclosure contains at least about 750 mg of fibrinogen (e.g., total mg of fibrinogen) at the time of thawing (e.g., within about 1 hour or within about 2 hours of thawing). In some embodiments, an amount of fibrinogen is determined from cryoprecipitate sampled within about 2 hours, within about 6 hours, within about 1 day, within about 2 days, within about 3 days, within about 4 days, or within about 5 days after thawing.

In some embodiments, a composition contains cryoprecipitate prepared from at least about 550 mL and less than about 650 mL of pathogen-inactivated plasma. In some embodiments, a composition contains two or more cryoprecipitates, each of the two or more cryoprecipitates prepared from at least about 150 mL and less than about 250 mL of plasma, e.g., about 200 mL of plasma. In some embodiments, cryoprecipitate prepared from at least about 550 mL and less than about 650 mL of pathogen-inactivated plasma contains between about 700 mg and about 1000 mg of fibrinogen, e.g., at or shortly preceding the infusion (e.g., up to about 1 day, up to about 3 days, up to about 5 days, or up to about 7 days after thawing). For example, in some embodiments, cryoprecipitate prepared from at least about 550 mL and less than about 650 mL of pathogen-inactivated plasma contains between about 700 mg and about 1000 mg of fibrinogen at the time of thawing (e.g., within about 1 hour or within about 2 hours of thawing). In some embodiments, cryoprecipitate prepared from at least about 550 mL and less than about 650 mL of pathogen-inactivated plasma contains between about 700 mg and about 1000 mg of fibrinogen as determined within about 2 hours, within about 6 hours, within about 1 day, within about 2 days, within about 3 days, within about 4 days, or within about 5 days after thawing.

In some embodiments, a composition contains a first cryoprecipitate prepared from at least about 550 mL and less than about 650 mL of pathogen-inactivated plasma and a second cryoprecipitate prepared from at least about 550 mL and less than about 650 mL of pathogen-inactivated plasma. In some embodiments, a composition containing two cryoprecipitates, each prepared from at least about 550 mL and less than about 650 mL of pathogen-inactivated plasma, contains between about 1400 mg and about 2000 mg of fibrinogen, e.g., at or shortly preceding the infusion (e.g., up to about 1 day, up to about 3 days, up to about 5 days, or up to about 7 days after thawing). For example, in some embodiments, a composition containing two cryoprecipitates, each prepared from at least about 550 mL and less than about 650 mL of pathogen-inactivated plasma, contains between about 1400 mg and about 2000 mg of fibrinogen at the time of thawing (e.g., within about 1 hour or within about 2 hours of thawing). In some embodiments, a composition containing two cryoprecipitates, each prepared from at least about 550 mL and less than about 650 mL of pathogen-inactivated plasma, contains between about 1400 mg and about 2000 mg of fibrinogen as determined within about 2 hours, within about 6 hours, within about 1 day, within about 2 days, within about 3 days, within about 4 days, or within about 5 days after thawing.

In some embodiments, a cryoprecipitate or cryoprecipitate composition of the present disclosure may be tested for vWF. Various assays for measuring vWF (such as vWF:RCo and vWF:Ag assays) are known in the art, including without limitation vWF ELISA, platelet agglutination, flow cytometry, and latex immunoassays. In some embodiments, a cryoprecipitate or cryoprecipitate composition of the present disclosure contains an amount of vWF meeting AABB standards. In some embodiments, a cryoprecipitate or cryoprecipitate composition of the present disclosure contains at least about 80, at least about 90, at least about 100, at least about 110, at least about 120, at least about 130, at least about 140, or at least about 150 IU of vWF per unit of cryoprecipitate (e.g., per unit of cryoprecipitate derived from about 200 mL of plasma). In some embodiments, a composition comprising a cryoprecipitate of the present disclosure includes vWF at an amount that is less than about any of the following amounts (in IU, either absolute or per unit of cryoprecipitate): 450, 400, 350, 300, 250, 200, 150, 140, 130, 120, 110, 100, or 90. In some embodiments, a composition comprising a cryoprecipitate of the present disclosure includes vWF at an amount that is greater than about any of the following amounts (in IU, either absolute or per unit of cryoprecipitate): 80, 90, 100, 110, 120, 130, 140, 150, 200, 250, 300, 350, or 400. That is, the composition comprising a cryoprecipitate of the present disclosure may include vWF at any amount within a range having an upper limit of 450, 400, 350, 300, 250, 200, 150, 140, 130, 120, 110, 100, or 90 IU and an independently selected lower limit of 80, 90, 100, 110, 120, 130, 140, 150, 200, 250, 300, 350, or 400 IU, wherein the upper limit is greater than the lower limit. In some embodiments, a cryoprecipitate or cryoprecipitate composition of the present disclosure contains at least about 100 IU or at least about 150 IU of vWF per unit of cryoprecipitate at the time of thawing (e.g., within about 1 hour or within about 2 hours of thawing). In some embodiments, a cryoprecipitate or cryoprecipitate composition of the present disclosure contains at least about 100 IU or at least about 150 IU of vWF per unit of cryoprecipitate at or shortly preceding the infusion (e.g., up to about 1 day, up to about 3 days, up to about 5 days, or up to about 7 days after thawing).

In some embodiments, a cryoprecipitate or cryoprecipitate composition of the present disclosure may be tested for Factor XIII. Various assays for measuring Factor XIII are known in the art, including without limitation the Berichrom assay, the clot solubility assay, and a Factor XIII ELISA. In some embodiments, a cryoprecipitate or cryoprecipitate composition of the present disclosure contains an amount of Factor XIII meeting AABB standards. In some embodiments, a cryoprecipitate or cryoprecipitate composition of the present disclosure contains at least about 40, at least about 50, at least about 60, at least about 70, at least about 80, at least about 90, or at least about 100 IU of Factor XIII per unit of cryoprecipitate (e.g., per unit of cryoprecipitate derived from about 200 mL of plasma). In some embodiments, a composition comprising a cryoprecipitate of the present disclosure includes Factor XIII at an amount that is less than about any of the following amounts (in IU, either absolute or per unit of cryoprecipitate): 300, 275, 250, 225, 200, 175, 150, 125, 100, 90, 80, 70, 60, or 50. In some embodiments, a composition comprising a cryoprecipitate of the present disclosure includes Factor XIII at an amount that is greater than about any of the following amounts (in IU, either absolute or per unit of cryoprecipitate): 40, 50, 60, 70, 80, 90, 100, 125, 150, 175, 200, 225, 250, or 275. That is, the composition comprising a cryoprecipitate of the present disclosure may include Factor XIII at any amount within a range having an upper limit of 300, 275, 250, 225, 200, 175, 150, 125, 100, 90, 80, 70, 60, or 50 IU and an independently selected lower limit of 40, 50, 60, 70, 80, 90, 100, 125, 150, 175, 200, 225, 250, or 275 IU, wherein the upper limit is greater than the lower limit. In some embodiments, a cryoprecipitate or cryoprecipitate composition of the present disclosure contains at least about 100 IU or at least about 150 IU of Factor XIII per unit of cryoprecipitate at the time of thawing (e.g., within about 1 hour or within about 2 hours of thawing). In some embodiments, a cryoprecipitate or cryoprecipitate composition of the present disclosure contains at least about 100 IU or at least about 150 IU of Factor XIII per unit of cryoprecipitate at or shortly preceding the infusion (e.g., up to about 1 day, up to about 3 days, up to about 5 days, or up to about 7 days after thawing).

Any of the above amounts of cryoprecipitate components may be combined in any number or combination described herein. For example, in some embodiments, a cryoprecipitate or cryoprecipitate composition of the present disclosure contains less than about 80 IU or less than about 50 IU of Factor VIII per unit of cryoprecipitate and at least about 250 mg or at least about 150 mg of fibrinogen per unit of cryoprecipitate at the time of thawing (e.g., within about 1 hour or within about 2 hours of thawing). In some embodiments, a cryoprecipitate or cryoprecipitate composition of the present disclosure contains less than about 80 IU or less than about 50 IU of Factor VIII per unit of cryoprecipitate and at least about 250 mg or at least about 150 mg of fibrinogen per unit of cryoprecipitate at or shortly preceding the infusion (e.g., up to about 1 day, up to about 3 days, up to about 5 days, or up to about 7 days after thawing).

In some embodiments, a cryoprecipitate or cryoprecipitate composition of the present disclosure may be prepared from plasma other than group O plasma, e.g., group A, B, and/or AB plasma. In some embodiments, a cryoprecipitate or cryoprecipitate composition of the present disclosure may be prepared from plasma of more than one ABO type. In some embodiments, a cryoprecipitate or cryoprecipitate composition of the present disclosure may be prepared from A, B, and AB type plasma.

In some embodiments, a cryoprecipitate or cryoprecipitate composition of the present disclosure may be contained in a container of the present disclosure. In some embodiments, the container further comprises a label indicating that the composition is suitable for use (e.g., suitable for infusion) for up to about 1 day, 2 days, 3 days, 4 days, 5 days, 6 days, or 7 days after thawing.

Further provided herein is a cryoprecipitate produced by any of the methods of the present disclosure, e.g., including one or more of the aspects and features described above in any order or combination.

Cryoprecipitate Kits or Articles of Manufacture

In some embodiments, a cryoprecipitate or cryoprecipitate composition of the present disclosure, or a cryoprecipitate or cryoprecipitate composition produced by the methods of the present disclosure, may be packaged in a kit or article of manufacture. In some embodiments, a kit or article of manufacture may include a container, a pathogen-inactivated cryoprecipitate, and instructions for using the pathogen-inactivated cryoprecipitate. In some embodiments, a kit or article of manufacture may include a container, a pathogen-inactivated cryoprecipitate, and a label indicating that the pathogen-inactivated cryoprecipitate is suitable for use for up to about 1 day, up to about 2 days, up to about 3 days, up to about 4 days, up to about 5 days, up to about 6 days, or up to about 7 days after thawing. In some embodiments, a kit or article of manufacture may further include any other material or device useful in a treatment (e.g., a transfusion), including without limitation one or more containers, tubing, sterilizing agents or equipment, cannulae, syringes, and the like.

In some embodiments, the instructions may be for using the pathogen-inactivated cryoprecipitate in an infusion into a subject. In some embodiments, the instructions may indicate an expiry date of the cryoprecipitate, e.g., a date by which the cryoprecipitate should be used in a treatment (e.g., an infusion) after thawing. In some embodiments, the instructions may indicate that the cryoprecipitate is suitable for infusion into the subject for up to about 1 day, up to about 2 days, up to about 3 days, up to about 4 days, up to about 5 days, up to about 6 days, or up to about 7 days after thawing. In some embodiments, the instructions may indicate that the cryoprecipitate is suitable for infusion into the subject for up to about 6 hours, up to about 12 hours, up to about 24 hours, up to about 36 hours, up to about 48 hours, up to about 60 hours, up to about 72 hours, up to about 84 hours, up to about 96 hours, up to about 108 hours, up to about 120 hours, up to about 132 hours, up to about 144 hours, up to about 156 hours, or up to about 168 hours after thawing.

Cryoprecipitate Methods

Certain aspects of the present disclosure relate to methods of preparing a cryoprecipitate for infusion into a subject. Certain aspects of the present disclosure relate to methods of infusing a cryoprecipitate into a subject. It is to be understood that any of the cryoprecipitate or cryoprecipitate compositions of the present disclosure may find use in any of the methods described herein. It is to be understood that any of the features or aspects of cryoprecipitate or cryoprecipitate compositions of the present disclosure described herein may find use in any of the methods described herein in any combination.

In some embodiments, the methods of preparing a cryoprecipitate for infusion into a subject and/or methods of infusing a cryoprecipitate into a subject may include preparing a cryoprecipitate or cryoprecipitate composition of the present disclosure from pathogen-inactivated plasma. Any of the exemplary methods of preparing a cryoprecipitate from plasma (e.g., pathogen-inactivated plasma) described herein (e.g., supra), or any methods of preparing a cryoprecipitate from plasma known in the art, may be used. Any of the exemplary methods of pathogen inactivating plasma described herein (e.g., infra), or any methods of pathogen inactivating plasma known in the art, may be used to generate the pathogen-inactivated plasma.

In some embodiments, the methods of preparing a cryoprecipitate for infusion into a subject and/or methods of infusing a cryoprecipitate into a subject may include freezing a cryoprecipitate or cryoprecipitate composition of the present disclosure, e.g., as described supra or as is known in the art.

In some embodiments, the methods of preparing a cryoprecipitate for infusion into a subject and/or methods of infusing a cryoprecipitate into a subject may include thawing a frozen cryoprecipitate or cryoprecipitate composition of the present disclosure, e.g., as described supra or as is known in the art. In some embodiments, the thawed cryoprecipitate or cryoprecipitate composition may be suitable for infusion into a subject as described herein for at least about 1 day, at least about 2 days, at least about 3 days, at least about 4 days, at least about 5 days, at least about 6 days, or at least about 7 days after thawing. In some embodiments, the thawed cryoprecipitate or cryoprecipitate composition may be suitable for infusion into a subject as described herein for at least about 6 hours, at least about 12 hours, at least about 24 hours, at least about 36 hours, at least about 48 hours, at least about 60 hours, at least about 72 hours, at least about 84 hours, at least about 96 hours, at least about 108 hours, at least about 120 hours, at least about 132 hours, at least about 144 hours, at least about 156 hours, or at least about 168 hours after thawing.

In some embodiments, the methods of preparing a cryoprecipitate for infusion into a subject and/or methods of infusing a cryoprecipitate into a subject may include testing the thawed cryoprecipitate (e.g., testing one or more representative random cryoprecipitate preparations) for Factor VIII, e.g., as described herein or known in the art. In some embodiments, the thawed cryoprecipitate may be tested for Factor VIII prior to infusion. In some embodiments, the thawed cryoprecipitate may have been tested for Factor VIII prior to freezing. In other embodiments, the methods of preparing a cryoprecipitate for infusion into a subject and/or methods of infusing a cryoprecipitate into a subject may exclude testing the thawed cryoprecipitate for Factor VIII. In some embodiments, the methods of preparing a cryoprecipitate for infusion into a subject and/or methods of infusing a cryoprecipitate into a subject may include testing the thawed cryoprecipitate for fibrinogen, but exclude testing for Factor VIII.

In some embodiments, the methods of preparing a cryoprecipitate for infusion into a subject and/or methods of infusing a cryoprecipitate into a subject may include testing the thawed cryoprecipitate (e.g., testing one or more representative random cryoprecipitate preparations) for fibrinogen, e.g., as described herein or known in the art. In some embodiments, the thawed cryoprecipitate may be tested for fibrinogen prior to infusion. In some embodiments, the thawed cryoprecipitate may have been tested for fibrinogen prior to freezing. In other embodiments, the methods of preparing a cryoprecipitate for infusion into a subject and/or methods of infusing a cryoprecipitate into a subject may exclude testing the thawed cryoprecipitate for fibrinogen.

In some embodiments, the methods of preparing a cryoprecipitate for infusion into a subject and/or methods of infusing a cryoprecipitate into a subject may include a cryoprecipitate made from about 600 mL of pathogen-inactivated plasma, from at least about 550 mL and less than 650 mL of pathogen-inactivated plasma, from at least about 570 mL and less than 620 mL of pathogen-inactivated plasma, or from at least about 600 mL and less than 650 mL of pathogen-inactivated plasma. Such a cryoprecipitate may be obtained, e.g., from pooling multiple unit volumes of plasma (e.g., 200 mL unit volumes, AABB unit volumes, to yield 550-650 mL), or from pooling multiple cryoprecipitates obtained from different samples of plasma. Individual cryoprecipitates may be combined or pooled after cryoprecipitate production but prior to use, storage at room temperature or under refrigeration, and/or re-freezing for storage; and/or individual plasma samples may be combined or pooled prior to cryoprecipitate production. In some embodiments, two or more cryoprecipitates may be combined prior to using, storing, and/or freezing the cryoprecipitate. In some embodiments, two or more cryoprecipitates may be combined after freezing the cryoprecipitate but prior to infusion.

In some embodiments, the methods of the present disclosure may further comprise infusing a cryoprecipitate or cryoprecipitate composition of the present disclosure into a subject. Methods of infusing a cryoprecipitate into a subject are well known in the art. In some embodiments, the cryoprecipitate may be infused at a rate of about 1 mL, about 2 mL, about 3 mL, about 4 mL, about 5 mL, about 6 mL, about 7 mL, about 8 mL, about 9 mL, or about 10 mL per minute, or for a total duration of about 30 minutes to about 4 hours. In some embodiments, a pool of cryoprecipitates (e.g., equivalent to 2, 3, 4, 5, 6, 7, 8, 9, 10, 11, or 12 units) may be infused. In some embodiments, the infusion is sufficient to raise the subject's fibrinogen level by an amount from about 30 mg/dL to about 60 mg/dL, e.g., by about 40 mg/dL. In some embodiments, the infusion is a transfusion. Further description of cryoprecipitate infusion dosing, response, indications, and preparation may be found, e.g., in the American Red Cross Compendium of Transfusion Practice Guidelines, the disclosure of which is hereby incorporated by reference as it relates to cryoprecipitate infusion dosing, response, indications, and preparation.

Further disclosed herein are methods for preparing a cryoprecipitate for infusion into a subject. In some embodiments, the methods include preparing a cryoprecipitate from pathogen-inactivated plasma (e.g., as described herein) and freezing the cryoprecipitate. In some embodiments, the methods include preparing a cryoprecipitate from pathogen-inactivated plasma (e.g., as described herein) and storing the cryoprecipitate at room temperature or under refrigeration before using in an infusion. In some embodiments, the cryoprecipitate is suitable for infusion into the subject for up to about 1 day, 2 days, 3 days, 4 days, 5 days 6 days, or 7 days after thawing, as described herein. In some embodiments, the cryoprecipitate is prepared from at least about 550 mL and less than about 650 mL of pathogen-inactivated plasma of the present disclosure. In certain embodiments, the cryoprecipitate is prepared from about 600 mL of pathogen-inactivated plasma of the present disclosure.

In some embodiments, the methods further include combining a first cryoprecipitate prepared from at least about 150 mL and less than about 250 mL (e.g., about 200 mL) of pathogen-inactivated plasma of the present disclosure and a second cryoprecipitate prepared from at least about 150 mL and less than about 250 mL (e.g., about 200 mL) of pathogen-inactivated plasma of the present disclosure. In some embodiments, the methods further include combining a first cryoprecipitate prepared from at least about 550 mL and less than about 650 mL of pathogen-inactivated plasma of the present disclosure and a second cryoprecipitate prepared from at least about 550 mL and less than about 650 mL of pathogen-inactivated plasma of the present disclosure. In some embodiments, the first and the second cryoprecipitates are combined prior to freezing the cryoprecipitate. In certain embodiments, the first cryoprecipitate is prepared from about 600 mL of pathogen-inactivated plasma of the present disclosure, and wherein the second cryoprecipitate is prepared from about 600 mL of pathogen-inactivated plasma of the present disclosure.

In some embodiments, the methods further include combining a first cryoprecipitate prepared or obtained from 1-3 (e.g., 3) units of pathogen-inactivated plasma of the present disclosure and a second cryoprecipitate prepared or obtained from 1-3 (e.g., 3) units of pathogen-inactivated plasma of the present disclosure. In some embodiments, the first and the second cryoprecipitates are combined prior to freezing the cryoprecipitate.

In any of the methods of the present disclosure, the subject may be a human. In other embodiments, the subject may be a veterinary subject.

Cryoprecipitate Processing

Cryoprecipitate processing and the handling of blood products typically involves the use of blood compatible bag systems, which are well known in the art, as described, for example, in U.S. Pat. Nos. 5,405,343, 7,025,877, and 8,439,889, the disclosures of which are incorporated by reference herein for the disclosure of blood handling bags and systems. In general, a blood handling system includes more than one plastic container, typically plastic bags, where the bags are integrally connected with plastic tubing. Some of the containers described herein include such plastic bags as are known in the storage and handling of blood products, including cryoprecipitates. Blood handling bags typically can be designed to hold various volumes of fluid, including, but not limited to, volumes ranging from 50 mL to 2 liters, for example having up to a 1 liter capacity, up to a 1.5 liter capacity, or up to a 2 liter capacity. Examples of common blood-collection bags include such bags with volumes of 350 mL, 450 mL and 500 mL, among others. It is understood that when a method refers to a bag, it includes any such plastic bags used in blood handling. Where such bags are referred to as "removal bag", "product bag", "transfer bag", "collection bag," or "illumination bag", it is understood that these bags are typical blood handling bags, or are similar to such bags in nature. Plastic bags suitable for use according to the present disclosure include for example, those comprising PL2410, as well as other suitable plastics known in the art. Plastic bag materials include polyvinyl chloride, polyolefins, ethylene vinyl acetate, ethylene vinyl acetate blended with other plastics, and the like.

As described herein, where tubing is described as connecting e.g. two bags of a processing set, it is understood that the tubing may be joined at some point therebetween by another component of the connection between the two bags. For example, a removal bag connected to a product bag by tubing includes wherein the tubing comprises a filter between the two bags, i.e. the tubing is divided by a filter such that fluid flows from one bag to the other through the tubing and filter. In one example, tubing connecting a removal bag and a product bag can include a filter to remove any loose particles from fluid flowing from the removal device to the product bag, i.e. the tubing is divided by, or interrupted by the filter between the bags. Such filters are designed to remove any small particles that may come off of the removal device, while allowing platelets to pass through the filter. The tubing between bags allows for fluid to flow from one bag to another, which can be blocked to prevent the flow until necessary, e.g. as part of the processing the fluid in one bag may be prevented from flowing to the next bag until required for the next step in a process. As such an openable seal, such as a clamp, plug, valve or the like is included in or on the tubing connecting the bags, where the clamp, plug, valve or the like can be selectively opened as required, for example to transfer the fluid from one bag to the next. In certain preferred embodiments, the tubing between bags comprises a breakable seal, such as a breakable valve, whereupon breaking the breakable seal allows for the blood solution to flow between the bags through the tubing. It is understood that the breakable seal is contained within the connection between containers, such that sterility of the system is maintained. It is also understood that a tubing comprising a filter, or a breakable seal, includes where the tubing may be interrupted by the filter or the seal, for example the tubing runs from one bag and is connected to the filter or seal (an incoming portion of the tubing), and the tubing continues from another portion of the filter or seal to another bag (an outgoing portion of the tubing). In such a configuration, fluid flows from the first bag, through the incoming portion of the tubing, through the filter or seal, and through the outgoing portion of the tubing and into the other bag.

Different bags within a blood bag system can be used for different steps of a process. For example, a system of bags to be used for the pathogen inactivation of a unit of cryoprecipitate or plasma can include a container with pathogen inactivation compound contained within, a bag for receiving the unit of cryoprecipitate or plasma and a pathogen inactivation compound (e.g. an illumination bag), a bag for the illumination of the unit of cryoprecipitate or plasma when the pathogen inactivation method includes illumination (e.g., an illumination bag, and typically the same bag to receive the unit of cryoprecipitate or plasma and pathogen inactivation compound), a bag for the removal of pathogen inactivation compounds and/or by-products thereof from the treated unit of cryoprecipitate or plasma (e.g., referred to as a removal bag), and one or more bags for containing the final cryoprecipitate or plasma product, i.e. the pathogen inactivated cryoprecipitate or plasma unit that has the concentration of the inactivation compound and/or by-products thereof reduced to below a desired concentration, which is ready for use, can be stored for later use (e.g., referred to as a product bag), or in the case of plasma can be used to generate a cryoprecipitate. Each bag in the system is typically made up of a plastic material. For example, the container for containing a solution of pathogen inactivation compound can be made of a suitable plastic such as PL2411 (Baxter Healthcare), or other plastics such as polyvinyl chloride, polyolefins, ethylene vinyl acetate, ethylene vinyl acetate blended with other plastics, and the like. This container is also overwrapped with a material that is impermeable to light of a wavelength that will activate the photoactive pathogen inactivation compound (for example suitable plastic such as PL2420, Baxter Healthcare). The illumination bag for a photoactivated pathogen inactivation compound requires a clear, durable thermoplastic material that is translucent to light of the selected wavelength. Suitable plastics that are translucent to light in the UVA wavelength range include polyvinyl chloride, polyolefins, ethylene vinyl acetate, ethylene vinyl acetate blended with other plastics, or other blends of thermoplastic polymers. Such suitable plastics include PL2410 (Baxter Healthcare) and PL732 (Baxter Healthcare). Similar materials may be used to make the removal bag and the product bag. The product bags include those made of PL2410. Suitable bag materials are discussed, for example, in PCT publication number WO 2003078023, and U.S. Pat. No. 7,025,877, the disclosures of which are hereby incorporated by reference as it relates to such bag materials and related materials. In all cases, the materials used in preparing the processing set have to be sterilizable by known methods such as steam and gamma or electron beam radiation used to ensure sterility of the processing set. While these are exemplary materials for making the bags, the methods described herein are applicable to processes using any suitable bag material as would be readily available to one skilled in the art, and can also be used with containers other than bags. The bags used for illumination, removal, and storage are also designed to allow for gases such as oxygen and carbon dioxide to go into and out of the blood bag, so that the blood products therein have adequate oxygen supply and carbon dioxide levels during the processing and storage.

Pathogen Inactivation

Blood products, including cryoprecipitate or plasma blood products, may contain pathogens, or may be contaminated with pathogens during processing. As such, it is desirable to subject such blood products to a process in order to reduce the risk of transfusion-transmitted diseases. In some embodiments, plasma may be subjected to one or more treatments to inactivate pathogens (i.e., pathogen inactivation). In some embodiments, the pathogen-inactivated plasma may then be used to produce a cryoprecipitate, as described herein. In some embodiments, cryoprecipitate itself may be subjected to one or more treatments to inactivate pathogens (i.e., pathogen inactivation).

Various methods are available to mitigate the risk of transfusion-associated disease transmission in cryoprecipitate or plasma-containing blood products. Aside from screening and detection of pathogens and subsequent elimination of contaminated blood products, processes that incorporate treatments to inactivate pathogens (i.e., pathogen inactivation) that may be present are available. Ideally, such a process results in the inactivation of a broad range of pathogens such as viruses, bacteria and parasites that may be present in the blood product. In certain preferred embodiments, the method of pathogen inactivation requires addition of an amount of pathogen inactivation compound to a unit of cryoprecipitate or plasma. For example, pathogen inactivation may involve the addition of a low molecular weight compound that inactivates various pathogens.

In some embodiments, pathogen inactivation may involve photochemical inactivation (e.g., photoinactivation), which involves the addition of a photosensitizer that, when activated by illumination using light of suitable wavelengths, will inactivate a variety of pathogens that may be present. Two such methods include the addition of amotosalen or riboflavin to the blood product, with subsequent illumination with UV light. Other methods include illumination with UV light without addition of a photosensitizer, as well as illumination with other photoactive compounds, including psoralen derivatives other than amotosalen, isoalloxazines other than riboflavin, alloxazines, dyes such as phthalocyanines, phenothiazine dyes (e.g. methylene blue, azure B, azure C, thionine, toluidine blue), porphyrin derivatives (e.g. dihematoporphyrin ether, hematoporphyrin derivatives, benzoporphyrin derivatives, alkyl-substituted sapphyrin), and merocyanine 540 (Prodouz et al., Blood Cells 1992, 18(1): 101-14; Sofer, Gail, BioPharm, August 2002).

In some embodiments, the pathogen inactivation is carried out using an INTERCEPT® Blood System (Cerus), such as the INTERCEPT® Blood System for Plasma. The INTERCEPT® Blood System is well known in the art as a system for pathogen inactivation, with widespread adoption in European blood centers and FDA approval in the United States. For greater description of the INTERCEPT® Blood System and pathogen inactivation methods and compositions related thereto, see, e.g., U.S. Pat. Nos. 5,399,719, 5,556,993, 5,578,736, 5,585,503, 5,593,823, 5,625,079, 5,654,443, 5,712,085, 5,871,900, 5,972,593, 6,004,741, 6,004,742, 6,017,691, 6,194,139, 6,218,100, 6,503,699, 6,544,727, 6,951,713, 7,037,642, and 7,611,831; and PCT publication numbers WO 1995000141, WO 1996014739, WO 1997021346, WO 1998030327, WO 1999034914, and WO1999034915, the disclosures of each of which are hereby incorporated by reference as they relate to pathogen inactivation in blood products.

As described above, plasma or cryoprecipitate may be subjected to pathogen inactivation. An exemplary process for using the INTERCEPT® Blood System to pathogen inactivate plasma is as follows. A sample of plasma (e.g., containing one or more than one plasma units, AABB units) in the illumination container may be brought into contact with amotosalen from the amotosalen container (e.g., by connecting through tubing and breaking the amotosalen container cannula to release the amotosalen). After sealing the illumination container, it may be illuminated with UV according to manufacturer's protocols. Once illuminated, the plasma may be transferred through tubing into one or more storage containers through a compound adsorption device (CAD). Optionally, if more than one storage container of plasma is to be pooled, they may be pooled into a larger blood bag (e.g., a 600-650 mL bag for three plasma units, e.g., 200 mL units, AABB plasma units; such as a 600 mL PVC transfer pack). Cryoprecipitate may then be prepared (e.g., in the larger blood bag) as described herein. Liquid plasma may then be removed, e.g., by draining into one or more bags. Optionally, more than one cryoprecipitate sample may be produced; if so, the individual cryoprecipitates samples may be combined in a single container through use of a sterile dock/tubing. Cryoprecipitate may then be frozen and stored. It will be understood by one of skill in the art that alternative steps, combinations of steps, and order of steps may be followed.

In some embodiments, plasma or cryoprecipitate may be pathogen-inactivated in a container (e.g., a blood bag or other container described herein) suitable for photochemical inactivation of plasma under sterile conditions. This container may be coupled to a CAD (e.g., as described and/or referenced above) such that plasma can be transferred from the container to the CAD under sterile conditions. In some embodiments, the CAD may further be coupled to one or more second containers, such that the plasma can be transferred from the CAD to the one or more second containers under sterile conditions. For example, one 600 mL PVC transfer pack or other larger blood bag may be used for a single second container, or more than one (e.g., three) smaller blood bags (e.g., sized for one AABB unit) may be used as second containers. The one or more second containers may be suitable for freezing pathogen-inactivated plasma followed by thawing the pathogen-inactivated plasma under conditions that provide for the formation of cryoprecipitate. In some embodiments, a third container may be coupled to the one or more second containers, such that the pathogen-inactivated plasma can be transferred from the CAD to the one or more second containers to the third container under sterile conditions. The third container may be suitable for freezing pathogen-inactivated plasma followed by thawing the pathogen-inactivated plasma under conditions that provide for the formation of cryoprecipitate. For example, pathogen-inactivated plasma from multiple (e.g., three) second containers may be transferred to and combined within a larger third container (e.g., a 600-650 mL bag) for subsequent cryoprecipitate preparation.

Other pathogen inactivation systems include, for example, those described in PCT publication numbers WO 2012071135; WO 2012018484; WO 2003090794; WO 2003049784; WO 1998018908; WO 1998030327; WO 1996008965; WO 1996039815; WO 1996039820; WO 1996040857; WO 1993000005; US patent application number US 20050202395; and U.S. Pat. Nos. 8,296,071 and 6,548,242, the disclosures of which are hereby incorporated by reference as they relate to pathogen inactivation in blood products. Where addition of a compound to the blood product is used for pathogen inactivation, whether the method requires illumination or not, in some instances it is desirable to remove any residual pathogen inactivation compound or by-product thereof.

Some pathogen inactivation methods may require the use of a removal device, i.e. a device for reducing the concentration of pathogen inactivation compound, such as a small organic compound, and by-products thereof, in a unit of cryoprecipitate or plasma while substantially maintaining a desired biological activity of the cryoprecipitate or plasma. In some instances, the removal device comprises porous adsorbent particles in an amount sufficient to reduce the pathogen inactivation compound to below a desired concentration, wherein the adsorbent particles have an affinity for the pathogen inactivation compound, where it is understood that such adsorbent particle can be selected to best adsorb the compound or compounds to be removed, with minimal effect on components that should not be removed or damaged by contact with the adsorbent particle. A variety of adsorbent particles are known, including generally particles made from any natural or synthetic material capable of interacting with compounds to be removed, including particulates made of natural materials such as activated carbon, silica, diatomaceous earth, and cellulose, and synthetic materials such as hydrophobic resins, hydrophilic resins or ion exchange resins. Such synthetic resins include, for example, carbonaceous materials, polystyrene, polyacrylic, polyacrylic ester, cation exchange resin, and polystyrene-divinylbenzene. Detailed description of such removal devices suitable for use in the methods as described herein can be found in PCT publication numbers WO 1996040857, WO 1998030327, WO 1999034914, and WO 2003078023, the disclosures of which are hereby incorporated by reference with respect to the discussion of such removal devices and the adsorbent particles and other materials used to prepare such devices. Exemplary adsorbent particles include, but are not limited to, Amberlite (Rohm and Haas) XAD-2, XAD-4, XAD-7, XAD-16, XAD-18, XAD-1180, XAD-1600, XAD-2000, XAD-2010; Amberchrom (Toso Haas) CG-71m, CG-71c, CG-161m, CG161c; Diaion Sepabeads (Mitsubishi Chemicals) HP20, SP206, SP207, SP850, HP2MG, HP20SS, SP20MS; Dowex (Dow Chemical) XUS-40285, XUS-40323, XUS-43493 (also referred to as Optipore V493 (dry form) or Optipore L493 (hydrated form)), Optipore V503, Optipore SD-2; Hypersol Macronet (Purolite) MN-100, MN-102, MN-150, MN-152, MN-170, MN-200, MN-202, MN-250, MN-252, MN-270, MN-300, MN-400, MN-500, MN-502, Purosorb (Purolite) PAD 350, PAD 400, PAD 428, PAD 500, PAD 550, PAD 600, PAD 700, PAD 900, and PAD 950. The material used to form the immobilized matrix comprises a low melting polymer, such as nylon, polyester, polyethylene, polyamide, polyolefin, polyvinyl alcohol, ethylene vinyl acetate, or polysulfone. In one example, the adsorbent particles immobilized in a matrix are in the form of a sintered medium. While it is understood that the methods and devices described herein encompass removal devices as are known in the art, such methods and devices may be exemplified using the removal device of an amotosalen inactivated blood product as is commercially available. Some such removal devices contain Hypersol Macronet MN-200 adsorbent contained within a sintered matrix, where the sintered matrix comprises PL2410 plastic as a binder. In one instance, the removal device comprises Hypersol Macronet MN-200 adsorbent in a sintered matrix comprising PL2410, wherein the Hypersol Macronet MN-200 is in an amount of about 5 g dry weight equivalent.

As various resins may require different processing when used to make the removal devices useful in the methods and devices as described herein, comparison of amounts of adsorbent resins described herein, unless otherwise indicated, are comparison of the dry weight of the resin. For example, the resins are dried to <5% water prior to processing, and the equivalent of the dry weight of adsorbent is used in comparing amounts of resin in use. For example, Hypersol Macronet MN-200 is processed to stabilize the adsorbent, or what is typically referred to as wetting the adsorbent, so as to be directly usable upon contact with a blood product unit. Such a wetted sample may include, for example, about 50% glycerol or other suitable wetting agent. In some embodiments, the adsorbent resin is a polystyrene-divinylbenzene resin. In some embodiments, the polystyrene-divinylbenzene resin is Hypersol Macronet MN-200. In some embodiments, the adsorbent is contained within a sintered matrix, wherein the sintered matrix comprises PL2410 binder. In some embodiments, Hypersol Macronet MN-200 adsorbent is contained within a sintered matrix to provide a removal device.

Cryosupernatant Preparation

It will be appreciated by one of skill in the art that, in the process of generating a cryoprecipitate or cryoprecipitate composition of the present disclosure, cryosupernatant is also produced or formed. Such cryosupernatant may have medical uses of interest, such as infusion into a patient.

As such, disclosed herein are methods of preparing a pooled cryosupernatant for infusion into a subject. In some embodiments, the methods comprise freezing at least a first pathogen-inactivated plasma and a second pathogen-inactivated plasma. In some embodiments, the first and the second pathogen-inactivated plasmas have a combined volume of at least about 550 mL and less than about 650 mL. In some embodiments, the first and the second pathogen-inactivated plasmas each have a volume of at least about 550 mL and less than about 650 mL. In some embodiments, the first and the second pathogen-inactivated plasmas have a combined volume of about 600 mL. In some embodiments, the first and the second pathogen-inactivated plasmas each have a volume of about 600 mL. In some embodiments, three units (e.g., AABB plasma units) may be used.

In some embodiments, the first and the second pathogen-inactivated plasmas may then be thawed under conditions that provide for the formation of cryoprecipitates (e.g., as described herein). In some embodiments, each cryoprecipitate may then be separated from the corresponding cryosupernatant. In some embodiments, the two cryosupernatants may then be combined to form a pooled cryosupernatant.

In some embodiments, two pooled cryosupernatants (prepared, e.g., as described above) may be combined. For example, two pooled cryosupernatants may be combined, where each of the pooled cryosupernatants is obtained by pooling cryosupernatants obtained from pathogen-inactivated plasmas totaling at least about 550 mL and less than about 650 mL, e.g., as described above. As such, in some embodiments, a pooled cryosupernatant may be obtained from 1100-1300 mL of pathogen-inactivated plasma.

In some embodiments, plasma or cryoprecipitate may be pathogen-inactivated in a container (e.g., a blood bag or other container described herein) suitable for photochemical inactivation of plasma under sterile conditions. This container may be coupled to a CAD (e.g., as described and/or referenced above) such that plasma can be transferred from the container to the CAD under sterile conditions. In some embodiments, this container may be coupled to an additional (e.g., upstream) container suitable for mixing the one or more units of plasma with a pathogen-inactivating compound (e.g., as described and/or referenced herein). In some embodiments, the additional container is coupled to the first container such that the one or more units of plasma in admixture with the pathogen-inactivating compound can be transferred from the additional container to the first container under sterile conditions. In some embodiments, the CAD may further be coupled to one or more second containers, such that the plasma can be transferred from the CAD to the one or more second containers under sterile conditions. For example, one 600 mL PVC transfer pack or other larger blood bag may be used for a single second container, or more than one (e.g., three) smaller blood bags (e.g., sized for one AABB unit) may be used as second containers. The one or more second containers may be suitable for freezing pathogen-inactivated plasma followed by thawing the pathogen-inactivated plasma under conditions that provide for the formation of cryoprecipitate. In some embodiments, a third container may be coupled to the one or more second containers, such that the pathogen-inactivated plasma can be transferred from the CAD to the one or more second containers to the third container under sterile conditions. The third container may be suitable for freezing pathogen-inactivated plasma followed by thawing the pathogen-inactivated plasma under conditions that provide for the formation of cryoprecipitate. For example, pathogen-inactivated plasma from multiple (e.g., three) second containers may be transferred to and combined within a larger third container (e.g., a 600-650 mL bag) for subsequent cryoprecipitate preparation. In some embodiments, cryosupernatant may be separated from cryoprecipitate in one or more fourth containers (e.g., one or more 600-650 mL bags). In some embodiments, the one or more fourth containers may be configured to be coupled to one or more second containers or a third container, as described above, such that the supernatant can be transferred from the one or more second containers or the third container to the one or more fourth containers under sterile conditions to afford a pathogen-inactivated cryosupernatant contained within the one or more fourth containers and a pathogen-inactivated cryoprecipitate contained within the one or more second containers or the third container.

Further disclosed herein are methods for infusing a cryosupernatant of the present disclosure into a subject.

Processing Sets

Certain aspects of the present disclosure relate to processing sets. The processing sets of the present disclosure may find use, inter alia, in preparing a pathogen-inactivated cryoprecipitate, e.g., as described herein.

In some embodiments, a processing set of the present disclosure includes a first container within which a psoralen of the present disclosure can be photoactivated in the presence of one or more units of plasma under sterile conditions (e.g., as described and/or referenced herein). In some embodiments, the processing set further includes a compound absorption device (CAD) coupled to the first container such that the one or more units of plasma can be transferred from the first container to the compound absorption device under sterile conditions. In some embodiments, the processing set further includes one or more second containers. In some embodiments, each of the one or more second containers is coupled to the compound absorption device such that the one or more units of plasma can be transferred from the compound absorption device to the one or more second containers under sterile conditions, e.g., to provide pathogen-inactivated plasma suitable for infusion into a subject. As non-limiting examples, the one or more second containers could include one 600 mL PVC transfer pack or other larger blood bag, or more than one (e.g., three) smaller blood bags (e.g., sized for one AABB unit). In some embodiments, the one or more second containers are suitable for freezing the pathogen-inactivated plasma followed by thawing of the pathogen-inactivated plasma under conditions that provide for the formation of a precipitate and a supernatant.

In some embodiments, a processing set of the present disclosure further includes a third container. In some embodiments, the third container is configured to be coupled to the one or more second containers such that the pathogen-inactivated plasma can be transferred from the one or more second containers to the third container under sterile conditions. In some embodiments, the third container is suitable for freezing the pathogen-inactivated plasma followed by thawing of the pathogen-inactivated plasma under conditions that provide for the formation of a precipitate and a supernatant. In some embodiments, the third container may be e.g., a 600-650 mL bag.

In some embodiments, a processing set of the present disclosure further includes one or more fourth containers. In some embodiments, the one or more fourth containers are configured to be coupled to the one or more second containers as described above or to the third container as described above such that the supernatant can be transferred from the one or more second containers or the third container to the one or more fourth containers under sterile conditions, e.g., to afford a pathogen-inactivated cryosupernatant of the present disclosure contained within the one or more fourth containers and a pathogen-inactivated cryoprecipitate of the present disclosure contained within the one or more second containers or the third container. In some embodiments, the fourth container is suitable for storage of a pathogen-inactivated cryoprecipitate of the present disclosure under conditions in which the pathogen-inactivated cryoprecipitate is frozen. In some embodiments, two or more fourth containers are used. The two or more fourth containers may be configured to be coupled to one another while each of the two or more fourth containers contains pathogen-inactivated cryoprecipitate such that the cryoprecipitate contained within the two or more fourth containers can be combined in one of the two or more fourth containers. In some embodiments, a fourth container may be e.g., a 600-650 mL bag. Non-limiting examples of processing sets of the present disclosure are as follows.

In some embodiments, a processing set includes a first container within which a psoralen can be photoactivated in the presence of one or more units of plasma under sterile conditions; a compound absorption device (CAD) coupled to the first container such that the plasma can be transferred from the first container to the compound absorption device under sterile conditions; one or more second containers, each of which is coupled to the compound absorption device such that the plasma can be transferred from the compound absorption device to the one or more second containers under sterile conditions to provide pathogen-inactivated plasma suitable for infusion into a subject; and a third container, which is configured to be coupled to the one or more second containers such that the pathogen-inactivated plasma can be transferred from the one or more second containers to the third container under sterile conditions. In some embodiments, the one or more second containers are suitable for freezing the pathogen-inactivated plasma followed by thawing of the pathogen-inactivated plasma under conditions that provide for the formation of a precipitate and a supernatant. In some embodiments, the third container is coupled to the one or more second containers such that the supernatant can be transferred from the one or more second containers to the third container under sterile conditions to afford a pathogen-inactivated cryosupernatant contained within the third container and a pathogen-inactivated cryoprecipitate contained within the one or more second containers.

In other embodiments, a processing set includes a first container within which a psoralen can be photoactivated in the presence of one or more units of plasma under sterile conditions; a compound absorption device (CAD) coupled to the first container such that the plasma can be transferred from the first container to the compound absorption device under sterile conditions; one or more second containers, each of which is coupled to the compound absorption device such that the plasma can be transferred from the compound absorption device to the one or more second containers under sterile conditions to provide pathogen-inactivated plasma suitable for infusion into a subject; a third container, which is configured to be coupled to the one or more second containers such that the pathogen-inactivated plasma can be transferred from the one or more second containers to the third container under sterile conditions; and one or more fourth containers, each of which is configured to be coupled to the third container such that the supernatant can be transferred from the third container to the one or more fourth containers under sterile conditions to afford a pathogen-inactivated cryosupernatant contained within the one or more fourth containers and a pathogen-inactivated cryoprecipitate contained within the third container. In some embodiments, the third container is suitable for freezing the pathogen-inactivated plasma followed by thawing of the pathogen-inactivated plasma under conditions that provide for the formation of a precipitate and a supernatant.

Further non-limiting examples of processing sets are illustrated in FIGS. 1A-3B. Exemplary processing set 100 shown in FIG. 1A includes optional plasma bag 102 containing the donor plasma to be pathogen inactivated, container 104 that contains a pathogen inactivation compound (PIC, e.g., a psoralen), and bag 106 for photoactivation of the plasma (e.g., a first container of the present disclosure). Photoactivation bag 106 is coupled to CAD 108 through tubing 110, which allows for the transfer of plasma after photoactivation to the CAD. CAD 108 in turn is coupled to three smaller blood bags 112, 114, and 116 (e.g., second containers of the present disclosure) through tubing 118, which allows the plasma to pass through the CAD (e.g., to remove free photoproducts and/or unreacted pathogen inactivation compound) before being collected in the smaller blood bags. Optional larger bag 122 for freezing the plasma to form cryoprecipitate (e.g., a third container of the present disclosure) and optional larger bag 124 for separating the cryoprecipitate from the cryosupernatant (e.g., a fourth container of the present disclosure), which may be sterile docked (e.g., using sterile connect 126) to the tubing between the CAD 108 and the three-way lead 120 of tubing 118 after collection of the PI plasma in the three bags, are also depicted.

An alternative configuration for processing set 100 is shown in FIG. 1B, where the cryoprecipitate is separated from the cryosupernatant by flowing the cryosupernatant from sterile-docked third container 122 back into the three smaller blood bags 112, 114, and 116 (e.g., second containers of the present disclosure), rather than into the optional fourth container 124.

Figure 1C:
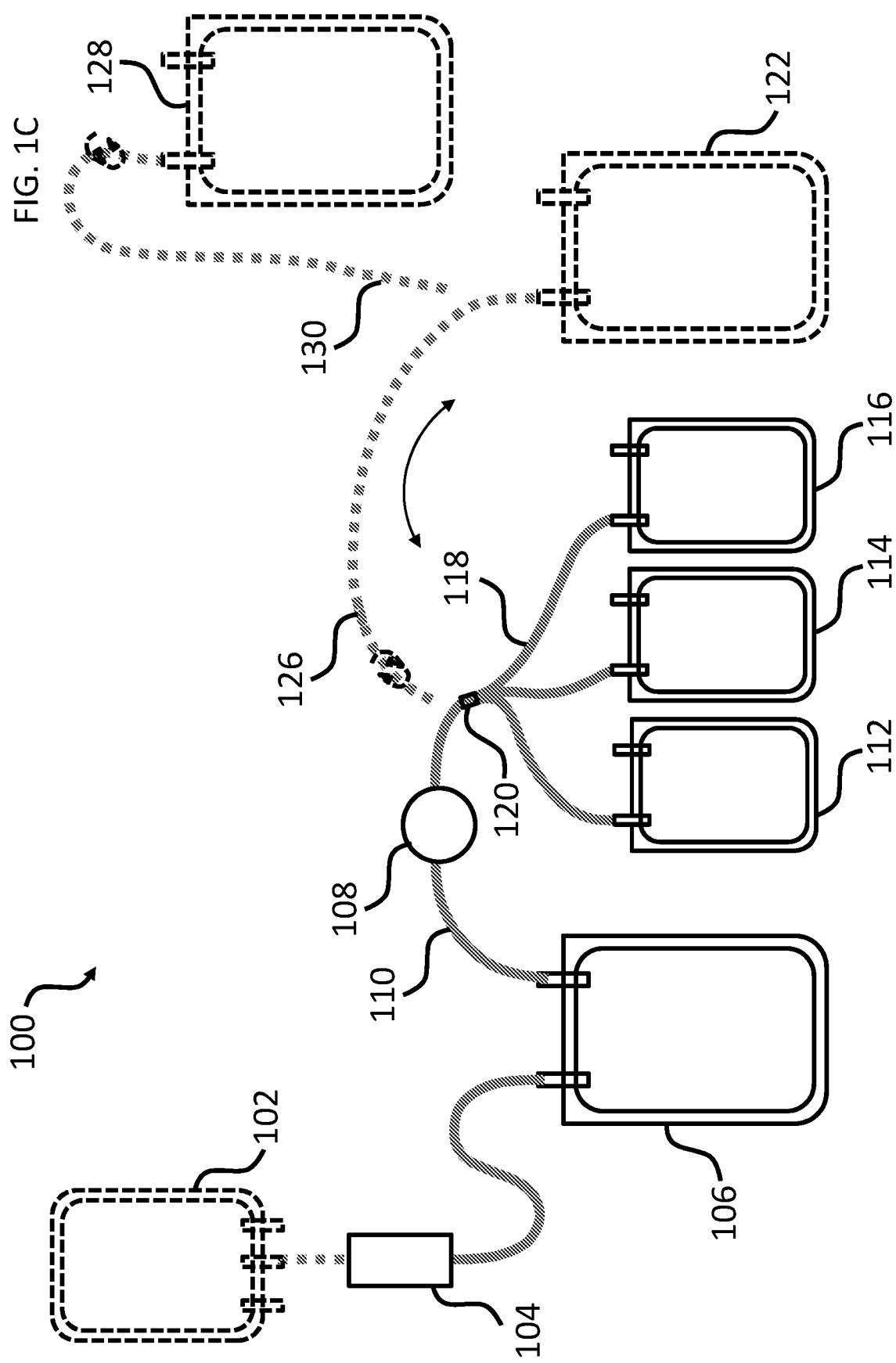
FIG. 1C shows an exemplary processing kit in accordance with some embodiments. Dotted components are optional.

Another alternative configuration for processing set 100 is shown in FIG. 1C. This configuration includes optional container 128 that is sterile connected or docked with third container 122 through sterile connect 130. This configuration allows two cryosupernatant preparations made from pathogen-inactivated plasma (e.g., prepared in 122 and 128) to be combined.

The exemplary processing set 200 shown in FIG. 2A, includes optional plasma bag 202 containing the donor plasma to be pathogen inactivated, container 204 that contains a pathogen inactivation compound (PIC), photoactivation bag 206, and CAD 208 coupled to photoactivation bag 206 with tubing 210 as described above, and additionally a pre-attached (e.g., integrated) third container 222. After collection of the pathogen-inactivated plasma in the three bags 212, 214, and 216, the three units of PI plasma are pooled by transferring into larger bag 222 (e.g., a third container of the present disclosure) for freezing to form cryoprecipitate and for separating cryoprecipitate from the cryosupernatant. As shown in FIG. 2B, cryosupernatant bag 224 (e.g., a fourth container of the present disclosure) may be used to collect the cryosupernatant after freezing (this is depicted as an optional component in FIG. 2A). This cryosupernatant bag may be connected to the larger freezing bag via tubing with common tubing clamp 226. An alternative configuration is shown in FIG. 2C, where the cryoprecipitate is separated from the cryosupernatant by flowing the cryosupernatant back into the three smaller blood bags 212, 214, and 216 (e.g., second containers of the present disclosure) using tubing 228, rather than into the fourth container 224 shown in FIG. 2B.

Figure 3A:
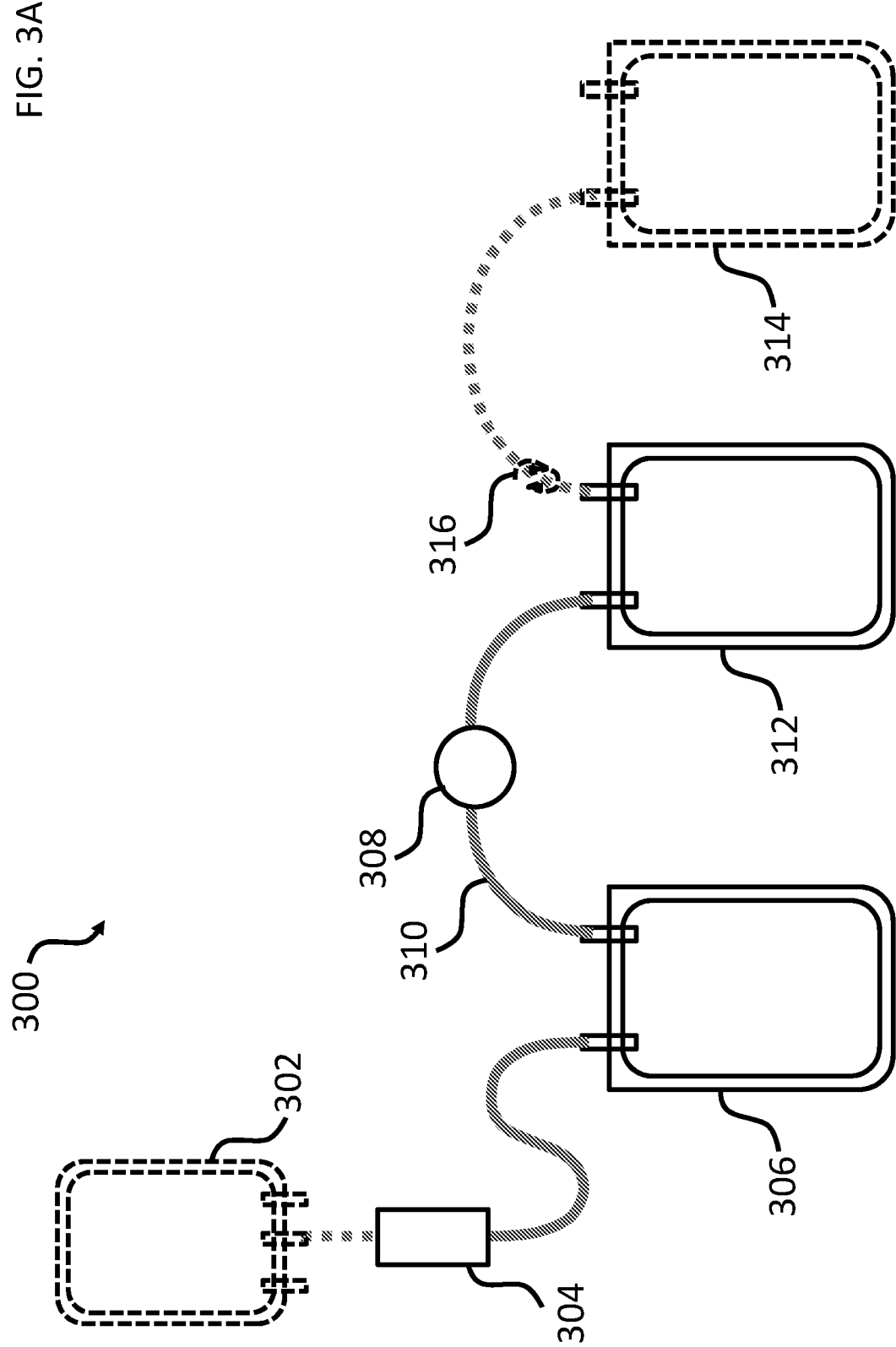
FIG. 3A shows an exemplary processing kit in accordance with some embodiments. Dotted components are optional.

The exemplary processing set 300 shown in FIG. 3A includes optional plasma bag 302 containing the donor plasma to be pathogen inactivated, container 304 that contains a pathogen inactivation compound (PIC), photoactivation bag 306, and CAD 308 coupled to photoactivation bag 306 with tubing 310 as described above. However, in this example, a single, larger (e.g., 800 mL) bag 312 (e.g., a third container of the present disclosure) replaces the three smaller bags (e.g., 212, 214, and 216). This bag 312 may be used for pathogen-inactivated plasma collection after photoactivation, as well as freezing/thawing for production of cryoprecipitate. The optional bag for cryosupernatant (e.g., 314) also depicted could be a pre-attached (e.g., integrated) part of the set with clamp 316 or alternatively sterile docked after PI plasma collection. In FIG. 3B, this cryosupernatant bag 314 (e.g., a fourth container of the present disclosure) is an integral part of set 300 coupled to the cryoprecipitate bag 312 (e.g., via tubing and a tubing clamp 316) and used to collect the cryosupernatant.

In any of the processing sets of the present disclosure, the first container (e.g., 106, 206, and/or 306) and the CAD (e.g., 108, 208, and/or 308) may be separated in a sterile manner from the rest of the components, such as the PI plasma and cryoprecipitate containers (e.g., 112, 114, 116, 212, 214, 216, and/or 312), e.g., before freezing.

As described herein, in some embodiments, two or more cryoprecipitate preparations of the present disclosure can be combined or pooled. Exemplary technique 400 for this pooling is shown in FIG. 4. Containers 402 and 404 contain a first and a second cryoprecipitate preparation, respectively. They are combined in FIG. 4 by sterile docking, e.g., using sterile connect 406. The technique illustrated in FIG. 4 may be applied to any of the cryoprecipitate preparations described herein, e.g., the cryoprecipitate preparations made from pathogen-inactivated plasma contained in containers 122, 222, and/or 312.

Figure 5:
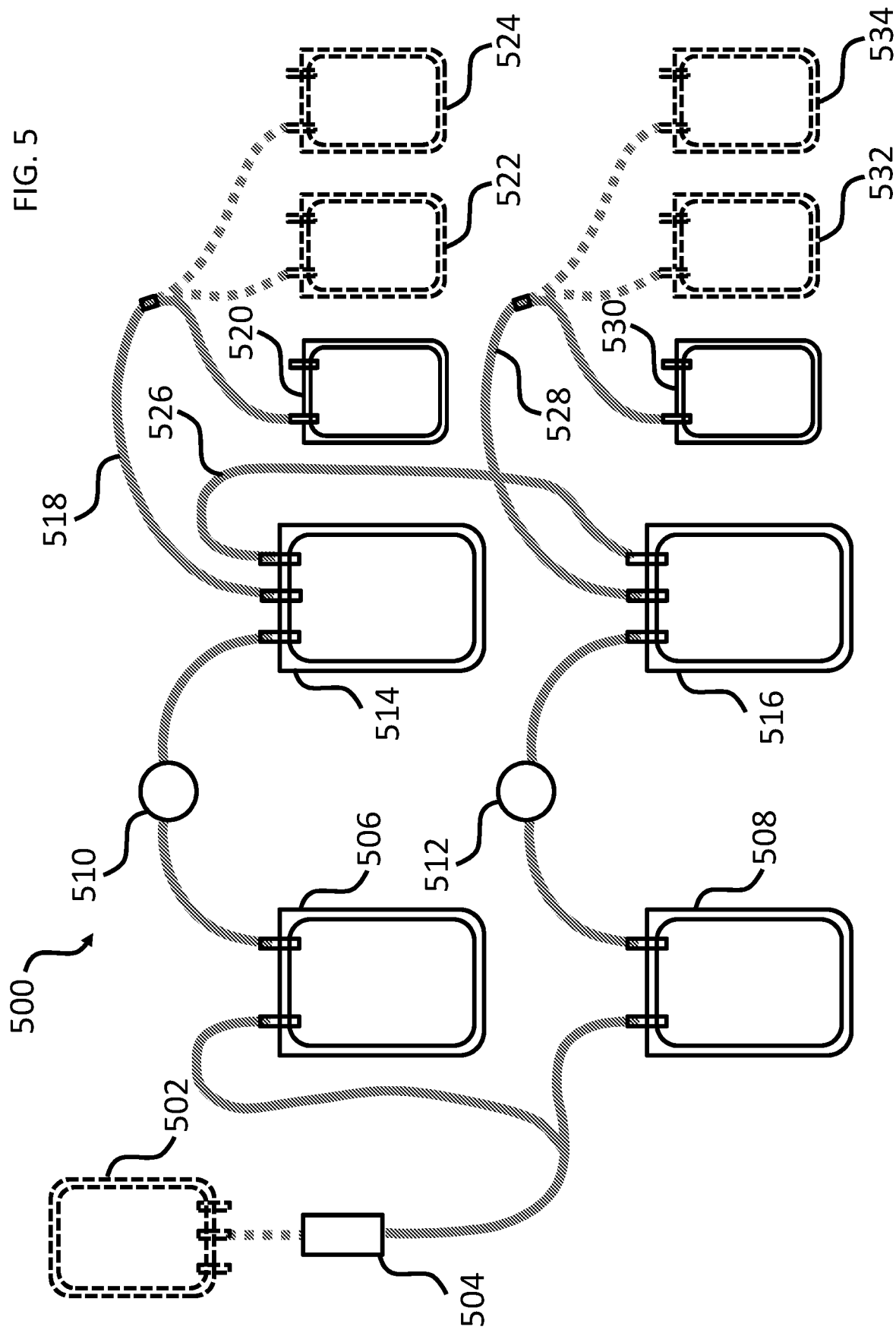
FIG. 5 shows an exemplary processing kit in accordance with some embodiments. Dotted components are optional.

Exemplary processing set 500 is shown in FIG. 5. Integrated processing set 500 allows for the production and combining or pooling of two larger cryoprecipitate preparations, e.g., as described herein. Processing set 500 includes one or more optional plasma containers (e.g., as shown by optional plasma container 502). Container(s) 502 is coupled to container 504, which contains a pathogen inactivation compound (PIC). Pathogen-inactivated plasma is then split into first and second photoactivation bags 506 and 508 (respectively), which in turn are coupled to first and second CADs 510 and 512 (respectively). CADs 510 and 512 are then coupled to first and second bags 514 and 516 (respectively), which are used for pathogen-inactivated plasma collection after photoactivation, as well as freezing/thawing for production of cryoprecipitate. For example, in some embodiments, 514 and/or 516 are larger (e.g., 800 mL) bags (e.g., third containers of the present disclosure), similar to bag 312 described above. Bag 514 is connected (e.g., through tubing 518) to cryosupernatant bags 520, 522, and 524 (e.g., fourth containers of the present disclosure) for collection of cryo-poor plasma. Similarly, bag 516 is connected (e.g., through tubing 528) to cryosupernatant bags 530, 532, and 534 (e.g., fourth containers of the present disclosure) for collection of cryo-poor plasma. In some embodiments, bags 514 and 516 are themselves connected via tubing 526, e.g., to allow the pathogen-inactivated cryoprecipitate preparations contained therein to be combined or pooled.

Figure 6:
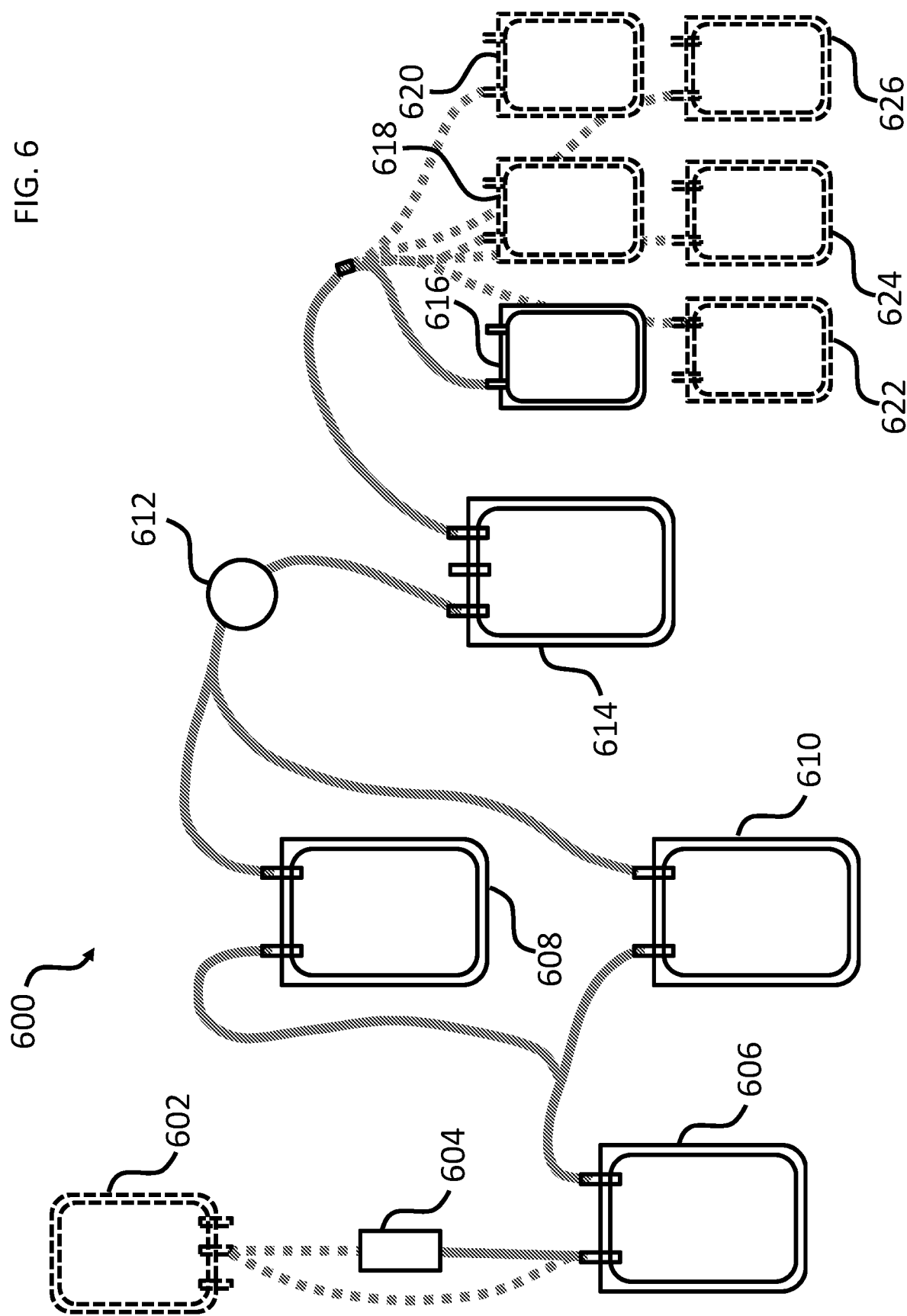
FIG. 6 shows an exemplary processing kit in accordance with some embodiments. Dotted components are optional.

Exemplary processing set 600 is shown in FIG. 6. Integrated processing set 600 represents another configuration that allows for the production and combining or pooling of two larger cryoprecipitate preparations, e.g., as described herein. Processing set 600 includes one or more optional plasma containers (e.g., as shown by optional plasma container 602). Container(s) 602 is coupled to container 604, which contains a pathogen inactivation compound (PIC). Container 604 is then coupled to mixing container 606, which is used to contain the plasma/PIC mixture (optionally, as depicted in FIG. 6, container 602 may be coupled directly to mixing container 606 without 604 as an intermediary). The plasma/PIC mixture is then split into first and second photoactivation bags 608 and 610 (respectively). After photoactivation, the split plasma/PIC mixtures are then passed through CAD 612 and into bag 614, which is used for pathogen-inactivated plasma collection after photoactivation, as well as freezing/thawing for production of cryoprecipitate. In some embodiments, bag 614 is a larger (e.g., 800 mL) bag (e.g., a third container of the present disclosure), similar to bag 312 described above. One or more cryosupernatant bags (e.g., bags 616, 618, 620, 622, 624, and 626) are connected to bag 614 for collection of cryo-poor plasma.

Exemplary processing set 700 is shown in FIG. 7. Integrated processing set 700 allows for the combining or pooling of multiple cryoprecipitate preparations into a single cryoprecipitate pool, which can then be subject to pathogen inactivation to yield a pooled, pathogen-inactivated cryoprecipitate preparation. Advantageously, this allows for multiple cryoprecipitate preparations to be subject to pathogen inactivation in a single step. As shown in FIG. 7, multiple cryoprecipitate preparations 702 are pooled into cryoprecipitate pool 704. In some embodiments, 702 includes 2, 3, 4, 5, 6, 7, 8, 9, 10, 11, or 12 separate cryoprecipitate preparations. In some embodiments, each cryoprecipitate preparation of 702 is between about 40 mL and about 60 mL. Cryoprecipitate pool 704 is then coupled to container 706, which contains a pathogen inactivation compound (PIC). Container 706 is coupled to photoactivation bag 708, which is coupled to CAD 710. After the cryoprecipitate is mixed with the PIC, photoactivated, and passed through CAD 710, the pathogen-inactivated cryoprecipitate pool enters container 712. In some embodiments, the pathogen-inactivated cryoprecipitate pool is frozen and/or stored in container 712.

It is to be understood that any of the processing sets of the present disclosure may be used in any of the methods of the present disclosure, or used to contain and/or process any of the cryoprecipitates, cryoprecipitate compositions, and/or cryosupernatants of the present disclosure.

The disclosure is illustrated further by the following examples, which are not to be construed as limiting the disclosure in scope or spirit to the specific procedures described in them.

EXAMPLES

Example 1

Preparation of Pathogen Inactivated Cryoprecipitate

Multiple blood group O negative units of liquid plasma units from the day of draw were pooled and split to obtain multiple plasma units for processing, each with a final volume 585 to 650 mL. Pathogen inactivation and preparation of cryoprecipitate was undertaken with the pooled plasma units. The plasma was subjected to photochemical pathogen inactivation using the commercially available INTERCEPT Blood System for Plasma (Cerus Corporation). In the case of four of the pooled units subjected to INTERCEPT treatment, the pathogen inactivated plasma collected in the 3 storage bags of the INTERCEPT processing set was transferred to a single 1000 mL transfer bag as large volume unit preparations. Two other of the pooled units subjected to INTERCEPT treatment were maintained in the 3 storage bags as smaller volume individual "single unit" preparations. The pathogen inactivated plasma units were then frozen at −30° C. for use in the preparation of cryoprecipitate.

For preparing cryoprecipitate, units were thawed in a temperature controlled 4° C. water bath, with a total thaw time of approximately 6 hr 30 minute for the large cryo units and 4 hr 30 mm for the single cryo units. The thawed units were centrifuged for 12 minutes at 4° C. at 4200 rcf, with a slow deceleration. Cryo-poor supernatants were removed from the cryoprecipitates, while maintaining a small amount of plasma for re-suspension. Following resuspension, the cryoprecipitate units were frozen for storage at −30° C.

The frozen, stored cryoprecipitate units were thawed in a Helmer plasma thawer set at 35° C., with the cryoprecipitate full dissolved with no visible particulate matter. Thawed units were stored in a temperature controlled cabinet at 22° C., with samples removed at defined intervals of <2 hr, 6 hr, 24 hr and 5 days for analytical testing. Samples were tested for Factor VIII (FVIII) and Fibrinogen (FIB), with resulting data in the following Table 1.

TABLE 1

Fibrinogen and Factor VIII in cryoprecipitate preparations.

|  | 2 hr | 6 hr | 24 hr | 5 days |
|---|---|---|---|---|
| Large volume (n = 4), 60.2 ± 4.9 mL | | | | |
| Cryo FIB (mg) | 492.7 ± 70.7 | 498.7 ± 74.0 | 501.3 ± 61.46 | 482.9 ± 74.8 |
| Cryo FIB (mg/unit*) | 181.2 ± 24.3 | 183.5 ± 26.6 | 184.4 ± 21.22 | 177.6 ± 26.7 |
| Cryo FVIII (IU) | 182.6 ± 37.9 | 176.3 ± 26.9 | 177.6 ± 73.4 | 145.7 ± 37.5 |
| Cryo FVIII (IU/unit*) | 67.2 ± 13.7 | 64.9 ± 9.6 | 65.2 ± 26.6 | 53.6 ± 13.5 |
| Single unit (n = 2), 24.1 ± 11.5 mL | | | | |
| Cryo FIB (mg) | 315.4 ± 49.1 | 315.5 ± 38.8 | 301.2 ± 35.4 | 274.2 ± 55.3 |
| Cryo FIB (mg/unit*) | 192.6 ± 4.2 | 183.5 ± 26.6 | 184.4 ± 3.1 | 167.0 ± 11.4 |
| Cryo FVIII (IU) | 94.5 ± 32.5 | 89.2 ± 40.0 | 82.4 ± 33.0 | 69.3 ± 40.0 |
| Cryo FVIII (IU/unit*) | 57.0 ± 12.2 | 53.4 ± 17.3 | 49.5 ± 13.5 | 41.1 ± 19.0 |

*Based on AABB unit volume of 200 mL

Example 2

Preparation of Pathogen Inactivated Cryoprecipitate

Multiple plasma units obtained from blood group A donors were pooled to obtain plasma preparations with volumes of about 650 mL each (e.g., large volume). Pathogen inactivation and preparation of cryoprecipitate was undertaken with the pooled plasma units. The plasma was subjected to photochemical pathogen inactivation using the commercially available INTERCEPT Blood System for Plasma (Cerus Corporation) to yield three individual pathogen-inactivated plasma (PI plasma) units from each pool. The three PI plasma units (3 containers, see e.g., 112, 114, and 116 in FIG. 1B) generated from each INTERCEPT processing set were combined by transferring into a single 600 mL transfer bag and frozen at −30° C. for use in the preparation of cryoprecipitate.

For preparing cryoprecipitate, pooled units were thawed in a temperature controlled 4° C. water bath, with a total thaw time of approximately 6 hr 15 minutes. The thawed units were centrifuged for 12 minutes at 4° C. at 4200 rcf, with a slow deceleration. Cryo-poor plasma supernatants were removed from the cryoprecipitates by transfer into the three previous containers, 60 mL of plasma added back to the cryoprecipitate for re-suspension, and the cryoprecipitate units were frozen for storage at −30° C.

The frozen, stored cryoprecipitate units were thawed in a Helmer plasma thawing system at 37° C., with the cryoprecipitate fully dissolved with no visible particulate matter. Thawed units were stored in a temperature controlled cabinet at 22° C., with samples removed at defined intervals at least through day 5 post-thaw for analytical testing of Factor VIII (FVIII) and Fibrinogen (FIB), with resulting data in the following Table 2:

TABLE 2

Fibrinogen and Factor VIII in cryoprecipitate preparations.

|  | <2 hr | 6 hr | 24 hr | 48 hr |
|---|---|---|---|---|
| Cryo FIB (mg) | | | | |
| Cryo prep 1 | 960.5 | 926.5 | 942.0 | 937.8 |
| Cryo prep 2 | 661.4 | 676.0 | 670.0 | 683.3 |
| Cryo FVIII (IU) | | | | |
| Cryo prep 1 | 273.8 | 277.6 | 277.9 | 188.1 |
| Cryo prep 2 | 252.9 | 260.8 | 248.9 | 174.2 |

Example 3

Preparation of PI Cryoprecipitate and Cryo-Poor Plasma

Pathogen inactivated (PI) cryoprecipitate and cryo-poor plasma supernatant were prepared as three large volume (647±2 mL) input pools of 2-3 units of ABO matched whole blood derived plasma in CPD anticoagulant within 8 hr of draw.

The pooled plasma was subjected to photochemical pathogen inactivation using amotosalen and UVA, with the commercially available INTERCEPT Blood System for Plasma. Baseline samples were collected prior to INTERCEPT treatment, and pathogen inactivation was performed according to the manufacturer's package insert. The three PI plasma units (3 containers, see e.g., 112, 114, and 116 in FIG. 1B) generated from each INTERCEPT processing set were combined by sealing above the connection, sterilely connecting a 600 mL transfer bag, and transferring by gravity flow. After sampling, pathogen inactivated plasma preparations were subjected to rapid freezing and stored at −30° C. for use in the preparation of cryoprecipitate.

For preparing cryoprecipitate, the frozen plasma was thawed in a 4° C. water bath within approximately 12 hr, and centrifuged at 4,000×g for 12 mm to sediment the cryoprecipitate. The cryo-poor plasma was removed using a plasma expressor and transferred back into the three plasma bags of the INTERCEPT processing set, leaving approximately 60 mL of plasma for resuspension of the cryoprecipitate. The cryoprecipitate bag and CPP bags were separated and sealed using a tubing sealer, and frozen at −30° C. for storage.

For characterization, the frozen cryoprecipitate and cryo-supernatants were thawed at 37° C. in a QuickThaw™ Plasma Thawing System (Helmer, Noblesville, Ind.) and held at room temperature (22° C., 2 units) or refrigerated (4° C., 1 unit) for sterile sampling at times 0 hr, 6 hr, 24 hr, day 3 and day 5 post-thaw for analytical testing. In vitro assays for cryoprecipitate and cryo-poor plasma supernatant characterization included total fibrinogen and Factor VIII, as measured on diluted samples, using an AMAX coagulation analyzer. Table 3 includes total fibrinogen and Factor FVIII content for each of the three cryoprecipitate preparations.

TABLE 3

Fibrinogen and Factor VIII in cryoprecipitate preparations.

|  | 0 hr | 6 hr | 24 hr | D 3 | D 5 |
|---|---|---|---|---|---|
| Cryo FIB (mg) | | | | | |
| Cryo prep 1 (22° C.) | 901 | 857 | 887 | ND | 887 |
| Cryo prep 2 (22° C.) | 788 | 908 | ND | 771 | 995 |
| Cryo prep 3 (4° C.) | 772 | 896 | 969 | ND | 907 |

TABLE 3-continued

Fibrinogen and Factor VIII in cryoprecipitate preparations.

|  | 0 hr | 6 hr | 24 hr | D 3 | D 5 |
|---|---|---|---|---|---|
| Cryo FVIII (IU) | | | | | |
| Cryo prep 1 (22° C.) | 278 | 319 | 280 | ND | 286 |
| Cryo prep 2 (22° C.) | 319 | 347 | ND | 268 | 229 |
| Cryo prep 3 (4° C.) | 316 | 307 | 322 | ND | 218 |

ND: not determined.

Fibrinogen and Factor VIII were also determined for cryo-poor plasma by the same method. At time 0 hr, fibrinogen content was 772 mg, 746 mg and 736 mg total for preps 1, 2 and 3, respectively. Also, at time 0 hr, FVIII content was 54, 46 and 70 IU total for preps 1, 2 and 3, respectively.

Example 4

Preparation of PI Cryoprecipitate and Cryo-Poor Plasma

Pathogen inactivated (PI) cryoprecipitate and cryo-poor plasma supernatant were prepared as large volume (585 to 650 mL) input of whole blood derived FFP, whole blood derived PF24 or apheresis plasma (apheresis FFP) obtained from blood group A, B and/or O donors. Six replicates were prepared from pools of 5 to 6 iso-group units of whole blood derived plasma collected in CP2D anticoagulant to yield approximately 1700 mL. The pooled plasma was split into two components (target 625 mL±25 mL, FFP and PF24) and stored at room temperature for up to 8 hr (FFP) or 24 hr (PF24) prior to subjecting the plasma to photochemical pathogen inactivation using the commercially available INTERCEPT Blood System, and freezing. Two units were maintained as untreated controls without pathogen inactivation (target 215-235 mL, FFP and PF24). Additionally, six replicates of apheresis plasma were collected in ACD anticoagulant from a maximum of two iso-group donors and split into two components: one (target 625+25 mL) which was stored at room temperature for up to 8 hr prior to subjecting the plasma to pathogen inactivation and freezing, and the other maintained as untreated control. Baseline samples were collected prior to INTERCEPT treatment, and pathogen inactivation was performed according to the manufacturer's package insert. The three PI plasma units (3 containers, see e.g., FIG. 1B) generated from each INTERCEPT processing set were combined by transferring into a single 800 mL transfer bag (Terumo) and frozen for use in the preparation of cryoprecipitate. Controls were frozen without pathogen inactivation treatment.

For preparing cryoprecipitate, the combined frozen plasma was thawed in a temperature controlled 2-6° C. refrigerator, with a total thaw time of approximately 24 hr. The thawed plasma was centrifuged to sediment the cryoprecipitate, and the cryo-poor plasma supernatants were removed from the cryoprecipitate using a plasma expressor and transferred into the three previous containers, leaving sufficient plasma to result in about 60 mL of resuspended cryoprecipitate, the cryoprecipitate bag separated from the three cryo-poor plasma bags using a tube sealer, and the cryoprecipitate and CPP units frozen for storage.

For characterization, the frozen cryoprecipitate and cryosupernatants were thawed at 37° C. in a QuickThaw™ Plasma Thawing System (Helmer, Noblesville, Ind.) and held at room temperature (20-24° C.) for sterile sampling at times 0, 24 and 120 hours post-thaw for analytical testing. In vitro assays for cryoprecipitate and/or cryosupernatant include a panel of coagulation parameters (e.g., PT, aPTT, thrombin generation), coagulation factors and hemostatic system proteins (e.g., fibrinogen, Factors II, V, VII, VIII (VIII:C), IX, X, XI, XIII, vWF, ADAMTS-13), and other proteins and markers and/or function (e.g., antithrombin III, Protein C, Protein S, Alpha-2-PI, thrombin-antithrombin complexes, Factor VIIa, NAPTT, C3a, Ig's, ROTEM).

Analysis of FVIII, FXIII and fibrinogen was performed using an AMAX Destiny Plus coagulation analyzer and Stago Diagnostic reagents. The following Tables 4 and 5 include total fibrinogen and FVIII at times 0, 24 and 120 hours post-thaw for containers of cryoprecipitate product prepared from whole blood derived FFP, whole blood derived PF24 and apheresis derived FFP, with ABO blood types as listed, and support an extended post-thaw expiry for cryoprecipitate as disclosed herein.

TABLE 4

Total fibrinogen content (mg) after post-thaw storage.

| Plasma Unit | | t = 0 | t = 24 hr | t = 120 hr |
|---|---|---|---|---|
| WBD FFP Group O | Average | 758 | 786 | 793 |
| | SD | 192.4 | 229.8 | 183.8 |
| WBD FFP Group A | Average | 767 | 827 | 794 |
| | SD | 91.0 | 52.7 | 81.6 |
| WBD FFP All groups | Average | 762 | 806 | 794 |
| | SD | 134.7 | 150.8 | 127.2 |
| PF24 Group O | Average | 762 | 768 | 775 |
| | SD | 150.5 | 183.1 | 196.7 |
| PF24 Group A | Average | 693 | 682 | 695 |
| | SD | 77.0 | 97.3 | 64.5 |
| PF24 All groups | Average | 728 | 725 | 735 |
| | SD | 113.5 | 139.5 | 138.1 |
| Aph FFP Group O | Average | 923 | 914 | 963 |
| | SD | 195.3 | 281.2 | 239.1 |
| Aph FFP Group A and B | Average | 954 | 1041 | 1052 |
| | SD | 17.2 | 93.4 | 100.7 |
| Aph FFP All groups | Average | 942 | 978 | 1008 |
| | SD | 99.9 | 186.1 | 158.3 |

TABLE 5

Total Factor VIII content (IU) after post-thaw storage.

| Plasma Unit | | t = 0 | t = 24 hr | t = 120 hr |
|---|---|---|---|---|
| WBD FFP Group O | Average | 178 | 158 | 138 |
| | SD | 50.7 | 46.8 | 5.1 |
| WBD FFP Group A | Average | 226 | 195 | 204 |
| | SD | 30.7 | 34.9 | 45.5 |
| WBD FFP All groups | Average | 202 | 176 | 171 |
| | SD | 45.7 | 42.2 | 46.2 |
| PF24 Group O | Average | 197 | 175 | 168 |
| | SD | 14.7 | 12.6 | 6.5 |
| PF24 Group A | Average | 197 | 211 | 243 |
| | SD | 14.7 | 14.1 | 32.7 |
| PF24 All groups | Average | 197 | 193 | 206 |
| | SD | 13.2 | 23.3 | 45.9 |
| Aph FFP Group O | Average | 184 | 72 | 67 |
| | SD | 52.4 | 16.8 | 18.8 |
| Aph FFP Group A and B | Average | 269 | 110 | 100 |
| | SD | 65.9 | 48.8 | 29.0 |
| Aph FFP All groups | Average | 235 | 91 | 83 |
| | SD | 70.8 | 37.0 | 27.6 |

Example 5

PI Cryoprecipitate from Two Cryo Preparations

Pathogen inactivated cryoprecipitate compositions of the present disclosure may be combined to yield a cryoprecipitate composition with higher levels of desired factors, such as for example fibrinogen and Factor VIII. More specifically, a first cryoprecipitate is prepared from a large volume input of approximately 600 mL of FFP (e.g., 2-3 units, pooled) that is subjected to pathogen inactivation (e.g., INTERCEPT Blood System), as described in Example 2 above and illustrated in FIG. 1B. Following sedimentation of the cryoprecipitate, the cryo-poor supernatant is transferred back into the three containers for storage, leaving sufficient plasma for resuspension of the cryoprecipitate in approximately 35 mL. In addition, a second cryoprecipitate is prepared from a large volume input of approximately 600 mL of FFP (e.g., 2-3 units, pooled) of the same ABO type as the first cryoprecipitate and subjected to pathogen inactivation treatment in a similar manner. The container with the second cryoprecipitate is separated from the three cryo-poor plasma bags using a tube sealer, prior to combining with the first cryoprecipitate (FIG. 1C). The second cryoprecipitate (labeled Cryo "freeze" #2) is connected using a sterile connecting device to the container with the first cryoprecipitate, which has also been separated from its corresponding three cryo-poor plasma bags, and the two cryoprecipitate preparations combined by transfer prior to re-freezing or storage at room temperature for use.

Example 6

Preparation of Pathogen Inactivated Pooled Cryoprecipitate

In another method for preparing improved cryoprecipitate of the present disclosure, pathogen inactivated (PI) cryoprecipitate is prepared from pooled cryoprecipitate units. For example, in one embodiment, ten cryoprecipitate units are individually prepared from whole blood derived frozen FFP units of the same ABO type. The plasma units are thawed in a temperature controlled 4° C. water bath and centrifuged for 12 minutes at 4° C. at 4200 rcf, with a slow deceleration. Cryo-poor plasma supernatants are removed from the cryoprecipitate using a plasma expressor, leaving sufficient plasma to completely resuspend the cryoprecipitate in approximately 50 mL units. The expressed cryo-poor plasma is transferred to a separate container and stored frozen for use, such as plasma fractionation. Containers with the cryoprecipitate units are connected using a sterile connecting device to provide for aseptic transfer and pooling of the cryoprecipitate contents. After pooling, the approximately 500 mL of cryoprecipitate is subjected to photochemical pathogen inactivation with amotosalen and UVA in a processing set (e.g., FIG. 7, INTERCEPT Blood System for Plasma). The pathogen inactivated cryo (PI Cryo) is stored frozen at −30° C. until use.

Example 7

Preparation of Pathogen Inactivated Cryoprecipitate

Multiple plasma units obtained from blood donors are pooled to obtain plasma preparations with volumes of about 650 mL each. Pathogen inactivation and preparation of cryoprecipitate are undertaken with the pooled plasma units. The plasma is subjected to photochemical pathogen inactivation using the commercially available INTERCEPT Blood System for Plasma (Cerus Corporation). The PI plasma generated from the INTERCEPT processing set is transferred to one large container (see e.g., 800 mL bag 312 in FIG. 3B), which is frozen at −30° C. for use in the preparation of cryoprecipitate.

For preparing cryoprecipitate, frozen PI plasma is thawed in a temperature controlled 4° C. water bath, with a total thaw time of approximately 6 hr 30 minute for the large cryo unit. The thawed product is centrifuged for 12 minutes at 4° C. at 4200 rcf, with a slow deceleration. Cryo-poor supernatant is removed from the cryoprecipitate (see e.g., bag 314 in FIG. 3B), while maintaining a small amount of plasma for re-suspension. Following resuspension, the cryoprecipitate is frozen for storage at −30° C.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Wherever an open-ended term is used to describe a feature or element, it is specifically contemplated that a closed-ended term can be used in place of the open-ended term without departing from the spirit and scope of the disclosure. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the description and does not pose a limitation on the scope of the description unless otherwise claimed. No language in the specification should be construed as indicating any non-claimed element as essential to the practice of the compositions, methods, and kits disclosed herein.

Preferred embodiments are described herein. Variations of those preferred embodiments may become apparent to those working in the art upon reading the foregoing description. It is expected that skilled artisans will be able to employ such variations as appropriate, and the practice of the compositions, methods, and kits described herein otherwise than as specifically described herein. Accordingly, the compositions, methods, and kits described herein include all modifications and equivalents of the subject matter recited in the claims appended hereto as permitted by applicable law. Moreover, any combination of the above-described elements in all possible variations thereof is encompassed by the description unless otherwise indicated herein or otherwise clearly contradicted by context.

LIST OF EMBODIMENTS

Embodiment 1

A composition comprising a cryoprecipitate suitable for infusion into a subject at least 1 day after thawing, wherein the cryoprecipitate is pathogen-inactivated.

Embodiment 2

The composition of embodiment 1, wherein the composition is suitable for infusion into a subject at least 3 days after thawing.

Embodiment 3

The composition of embodiment 2, wherein the composition is suitable for infusion into a subject at least 5 days after thawing.

Embodiment 4

The composition of any one of embodiments 1-3, wherein the composition comprises cryoprecipitate prepared from at least about 550 mL and less than about 650 mL of pathogen-inactivated plasma.

Embodiment 5

The composition of any one of embodiments 1-4, wherein the composition comprises cryoprecipitate prepared from about 600 mL of pathogen-inactivated plasma.

Embodiment 6

The composition of any one of embodiments 1-3, wherein the composition comprises cryoprecipitate prepared from at least about 550 mL and less than about 650 mL of plasma, and wherein the prepared cryoprecipitate has been pathogen-inactivated.

Embodiment 7

The composition of any one of embodiments 1-3 and 6, wherein the composition comprises cryoprecipitate prepared from about 600 mL of plasma, and wherein the prepared cryoprecipitate has been pathogen-inactivated.

Embodiment 8

The composition of any one of embodiments 1-5, wherein the composition comprises cryoprecipitate prepared from 3 units of pathogen-inactivated plasma.

Embodiment 9

The composition of any one of embodiments 1-3, 6, and 7, wherein the composition comprises cryoprecipitate prepared from 3 units of plasma, and wherein the prepared cryoprecipitate has been pathogen-inactivated.

Embodiment 10

The composition of any one of embodiments 1-3, wherein the composition comprises a first cryoprecipitate prepared from at least about 550 mL and less than 650 mL of pathogen-inactivated plasma and a second cryoprecipitate prepared from at least about 550 mL and less than 650 mL of pathogen-inactivated plasma, wherein the first and the second cryoprecipitates are combined prior to re-freezing for storage.

Embodiment 11

The composition of any one of embodiments 1-3 and 10, wherein the composition comprises a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to re-freezing for storage.

Embodiment 12

The composition of any one of embodiments 1-3, wherein the composition comprises a first cryoprecipitate prepared from at least about 550 mL and less than 650 mL of plasma and a second cryoprecipitate prepared from at least about 550 mL and less than 650 mL of plasma, wherein the first and the second cryoprecipitates are combined prior to re-freezing for storage, and wherein the first and the second cryoprecipitates have been pathogen-inactivated after being combined and prior to re-freezing for storage.

Embodiment 13

The composition of any one of embodiments 1-3 and 10, wherein the composition comprises a first cryoprecipitate prepared from about 600 mL of plasma and a second cryoprecipitate prepared from about 600 mL of plasma, wherein the first and the second cryoprecipitates are combined prior to re-freezing for storage, and wherein the first and the second cryoprecipitates have been pathogen-inactivated after being combined and prior to re-freezing for storage.

Embodiment 14

The composition of any one of embodiments 1-3, wherein the composition comprises a first cryoprecipitate prepared from at least about 550 mL and less than 650 mL of plasma and a second cryoprecipitate prepared from at least about 550 mL and less than 650 mL of plasma, wherein the first and the second cryoprecipitates are combined prior to re-freezing for storage, and wherein the first and the second cryoprecipitates have been pathogen-inactivated prior to being combined and prior to re-freezing for storage.

Embodiment 15

The composition of any one of embodiments 1-3 and 10, wherein the composition comprises a first cryoprecipitate prepared from about 600 mL of plasma and a second cryoprecipitate prepared from about 600 mL of plasma, wherein the first and the second cryoprecipitates are combined prior to re-freezing for storage, and wherein the first and the second cryoprecipitates have been pathogen-inactivated prior to being combined and prior to re-freezing for storage.

Embodiment 16

The composition of any one of embodiments 1-3, wherein the composition comprises a first cryoprecipitate prepared from at least about 550 mL and less than 650 mL of pathogen-inactivated plasma and a second cryoprecipitate prepared from at least about 550 mL and less than 650 mL of pathogen-inactivated plasma, wherein the first and the second cryoprecipitates are combined prior to re-freezing for storage.

Embodiment 17

The composition of any one of embodiments 1-3 and 10, wherein the composition comprises a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to re-freezing for storage.

Embodiment 18

The composition of any one of embodiments 1-3, wherein the composition comprises a first cryoprecipitate prepared from 3 units of pathogen-inactivated plasma and a second cryoprecipitate prepared from 3 units of pathogen-inactivated plasma, wherein the first and the second cryoprecipitates are combined prior to re-freezing for storage.

Embodiment 19

The composition of any one of embodiments 1-3 and 10-18, wherein the composition comprises cryoprecipitate prepared from 6 units of pathogen-inactivated plasma.

Embodiment 20

The composition of any one of embodiments 1-19, wherein the composition comprises cryoprecipitate prepared from plasma obtained from one donor.

Embodiment 21

The composition of any one of embodiments 1-19, wherein the composition comprises cryoprecipitate prepared from plasma obtained from 2-6 donors.

Embodiment 22

The composition of any one of embodiments 1-21, wherein the composition comprises less than 80 IU of factor VIII per unit of cryoprecipitate.

Embodiment 23

The composition of embodiment 22, wherein the composition comprises less than 50 IU of factor VIII per unit of cryoprecipitate.

Embodiment 24

The composition of any one of embodiments 1-21, wherein the composition comprises 80-100 IU of factor VIII per unit of cryoprecipitate.

Embodiment 25

The composition of any one of embodiments 1-21, wherein the composition comprises at least 80 IU of factor VIII.

Embodiment 26

The composition of embodiment 25, wherein the composition comprises 80-240 IU of factor VIII.

Embodiment 27

The composition of embodiment 25, wherein the composition comprises 80-480 IU of factor VIII.

Embodiment 28

The composition of any one of embodiments 1-27, wherein the amount of factor VIII is determined from cryoprecipitate sampled within about 2 hours after thawing.

Embodiment 29

The composition of any one of embodiments 1-27, wherein the amount of factor VIII is determined from cryoprecipitate sampled about 1 day after thawing.

Embodiment 30

The composition of any one of embodiments 2-27, wherein the amount of factor VIII is determined from cryoprecipitate sampled about 3 days after thawing.

Embodiment 31

The composition of any one of embodiments 3-27, wherein the amount of factor VIII is determined from cryoprecipitate sampled about 5 days after thawing.

Embodiment 32

The composition of any one of embodiments 1-31, wherein the composition comprises at least 150 mg of fibrinogen per unit of cryoprecipitate.

Embodiment 33

The composition of any one of embodiments 1-32, wherein the composition comprises at least 250 mg of fibrinogen per unit of cryoprecipitate.

Embodiment 34

The composition of any one of embodiments 4-33, wherein the composition comprises at least 750 mg of fibrinogen.

Embodiment 35

The composition of any one of embodiments 10-33, wherein the composition comprises at least 1500 mg of fibrinogen.

Embodiment 36

The composition of any one of embodiments 8-35, wherein each unit of cryoprecipitate is prepared from 180-250 mL of pathogen-inactivated plasma.

Embodiment 37

The composition of any one of embodiments 1-36, wherein the composition further comprises plasma of a volume between about 5 mL and about 20 mL per unit of cryoprecipitate.

Embodiment 38

The composition of any one of embodiments 4-37, wherein the composition further comprises plasma of a volume greater than about 1 mL and less than or equal to about 75 mL.

Embodiment 39

The composition of any one of embodiments 4-38, wherein the composition further comprises plasma of a volume between about 40 mL and about 75 mL.

Embodiment 40

The composition of any one of embodiments 4-38, wherein the composition further comprises plasma of a volume between about 50 mL and about 60 mL.

Embodiment 41

The composition of any one of embodiments 10-37, wherein the composition further comprises plasma of a volume between about 30 mL and about 120 mL.

Embodiment 42

The composition of any one of embodiments 1-41, wherein the composition is stored at room temperature for at least 1 day after thawing.

Embodiment 43

The composition of any one of embodiments 1-41, wherein the composition is stored at between about 2° C. and about 6° C. for at least 1 day after thawing.

Embodiment 44

The composition of any one of embodiments 1-43, wherein the cryoprecipitate has been pathogen-inactivated by photochemical inactivation.

Embodiment 45

The composition of embodiment 44, wherein the cryoprecipitate has been pathogen-inactivated by photochemical inactivation with a psoralen.

Embodiment 46

The composition of embodiment 45, wherein the psoralen is amotosalen.

Embodiment 47

The composition of any one of embodiments 44-46, wherein the cryoprecipitate is prepared from plasma that has been pathogen-inactivated in a first container suitable for photochemical inactivation of the plasma under sterile conditions;
wherein the first container is coupled to a compound absorption device (CAD) such that the pathogen-inactivated plasma can be transferred from the first container to the CAD under sterile conditions; and
wherein the cryoprecipitate is contained within one or more second containers, each of which is coupled to the CAD such that the pathogen-inactivated plasma can be transferred from the CAD to the one or more second containers under sterile conditions, and each of which is suitable for freezing the pathogen-inactivated plasma followed by thawing of the pathogen-inactivated plasma under conditions that provide for the formation of the cryoprecipitate.

Embodiment 48

The composition of embodiment 47, wherein each of the one or more second containers is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the one or more second containers.

Embodiment 49

The composition of embodiment 47 or embodiment 48, wherein the cryoprecipitate is prepared from plasma that has been pathogen-inactivated in a first container suitable for photochemical inactivation of the plasma under sterile conditions;
wherein the first container is coupled to a compound absorption device (CAD) such that the pathogen-inactivated plasma can be transferred from the first container to the CAD under sterile conditions;
wherein the CAD is coupled to one or more second containers, each of which is coupled to the CAD such that the pathogen-inactivated plasma can be transferred from the CAD to the one or more second containers under sterile conditions; and
wherein the cryoprecipitate is contained within a third container configured to be coupled to one or more second containers, such that the pathogen-inactivated plasma can be transferred from the CAD to the one or more second containers to the third container under sterile conditions, wherein the third container is suitable for freezing the pathogen-inactivated plasma followed by thawing of the pathogen-inactivated plasma under conditions that provide for the formation of the cryoprecipitate.

Embodiment 50

The composition of embodiment 49, wherein the third container is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the third container.

Embodiment 51

The composition of any one of embodiments 1-50, wherein the composition is contained within a container that further comprises a label indicating that the composition is suitable for use for at least about 1 day after thawing.

Embodiment 52

The composition of any one of embodiments 2-50, wherein the composition is contained within a container that further comprises a label indicating that the composition is suitable for use for at least about 3 days after thawing.

Embodiment 53

The composition of any one of embodiments 3-50, wherein the composition is contained within a container that further comprises a label indicating that the composition is suitable for use for at least about 5 days after thawing.

Embodiment 54

The composition of any one of embodiments 1-53, wherein the cryoprecipitate is prepared from plasma other than group O plasma.

Embodiment 55

A method of preparing a cryoprecipitate for infusion into a subject comprising:
  a) preparing a cryoprecipitate from pathogen-inactivated plasma;
  b) freezing the cryoprecipitate; and
  c) thawing the frozen cryoprecipitate, wherein the resulting cryoprecipitate of step c) is suitable for infusion into a subject at least 1 day after thawing.

Embodiment 56

The method of embodiment 55, wherein the resulting cryoprecipitate of step c) is suitable for infusion into a subject at least 5 days after thawing.

Embodiment 57

The method of embodiment 55 or embodiment 56, wherein the thawed cryoprecipitate comprises at least about 150 mg of fibrinogen per unit of cryoprecipitate.

Embodiment 58

The method of embodiment 55, wherein the thawed cryoprecipitate comprises at least about 750 mg of fibrinogen.

Embodiment 59

The method of any one of embodiments 55-58, wherein the method does not comprise determining the level of factor VIII before infusing the thawed cryoprecipitate.

Embodiment 60

The method of any one of embodiments 55-58, further comprising determining the level of factor VIII in the thawed cryoprecipitate.

Embodiment 61

The method of any one of embodiments 55-60, wherein the cryoprecipitate is prepared from at least about 550 mL and less than about 650 mL of pathogen-inactivated plasma.

Embodiment 62

The method of any one of embodiments 55-61, wherein the cryoprecipitate is prepared from about 600 mL of pathogen-inactivated plasma.

Embodiment 63

The method of any one of embodiments 55-60, further comprising combining a first cryoprecipitate prepared from at least about 550 mL and less than about 650 mL of pathogen-inactivated plasma and a second cryoprecipitate prepared from at least about 550 mL and less than about 650 mL of pathogen-inactivated plasma, wherein the first and the second cryoprecipitates are combined prior to steps b) and c).

Embodiment 64

The method of any one of embodiments 55-60, further comprising combining a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to steps b) and c).

Embodiment 65

The method of any one of embodiments 55-60, further comprising combining a first cryprecipitate prepared from 3 units of pathogen-inactivated plasma and a second cryoprecipitate prepared from 3 units of pathogen-inactivated plasma, wherein the first and the second cryoprecipitates are combined prior to steps b) and c).

Embodiment 66

The method of any one of embodiments 55-65, wherein the resulting cryoprecipitate of step c) is suitable for infusion into a subject at least 3 days after thawing.

Embodiment 67

The method of embodiment 66, wherein the resulting cryoprecipitate of step c) is suitable for infusion into a subject at least 5 days after thawing.

Embodiment 68

A method of infusing a cryoprecipitate into a subject comprising:
  a) preparing a cryoprecipitate from pathogen-inactivated plasma;
  b) freezing the cryoprecipitate;
  c) thawing the frozen cryoprecipitate; and
  d) infusing the thawed cryoprecipitate into a subject, wherein the infusion occurs at least 1 day after thawing the frozen cryoprecipitate.

Embodiment 69

The method of embodiment 68, wherein the thawed cryoprecipitate comprises at least about 150 mg of fibrinogen per unit of cryoprecipitate.

Embodiment 70

The method of embodiment 68, wherein the thawed cryoprecipitate comprises at least about 750 mg of fibrinogen.

Embodiment 71

The method of any one of embodiments 68-70, wherein the method does not comprise determining the level of factor VIII before infusing the thawed cryoprecipitate.

Embodiment 72

The method of any one of embodiments 68-70, further comprising determining the level of factor VIII in the thawed cryoprecipitate before infusing the thawed cryoprecipitate.

Embodiment 73

The method of any one of embodiments 68-72, wherein the cryoprecipitate is prepared from at least about 550 mL and less than about 650 mL of pathogen-inactivated plasma.

Embodiment 74

The method of any one of embodiments 68-73, wherein the cryoprecipitate is prepared from about 600 mL of pathogen-inactivated plasma.

Embodiment 75

The method of any one of embodiments 68-72, further comprising combining a first cryoprecipitate prepared from at least about 550 mL and less than about 650 mL of pathogen-inactivated plasma and a second cryoprecipitate prepared from at least about 550 mL and less than about 650 mL of pathogen-inactivated plasma, wherein the first and the second cryoprecipitates are combined prior to steps b) and c).

Embodiment 76

The method of any one of embodiments 68-72, further comprising combining a first cryoprecipitate prepared from about 600 mL of pathogen-inactivated plasma and a second cryoprecipitate prepared from about 600 mL of pathogen-inactivated plasma, wherein the first and the second cryoprecipitates are combined prior to steps b) and c).

Embodiment 77

The method of any one of embodiments 68-72, further comprising combining a first crypecipitate prepared from 3 units of pathogen-inactivated plasma and a second cryoprecipitate prepared from 3 units of pathogen-inactivated plasma, wherein the first and the second cryoprecipitates are combined prior to steps b) and c).

Embodiment 78

The method of any one of embodiments 55-77, wherein the resulting cryoprecipitate of step c) comprises less than 80 IU of factor VIII per unit of cryoprecipitate.

Embodiment 79

The method of any one of embodiments 55-77, wherein the resulting cryoprecipitate of step c) comprises at least about 80 IU of factor VIII.

Embodiment 80

The method of embodiment 79, wherein the resulting cryoprecipitate of step c) comprises 80-240 IU of factor VIII.

Embodiment 81

The method of embodiment 79, wherein the resulting cryoprecipitate of step c) comprises 80-480 IU of factor VIII.

Embodiment 82

The method of embodiment 79, wherein the resulting cryoprecipitate of step c) comprises less than 50 IU of factor VIII per unit of cryoprecipitate.

Embodiment 83

The method of any one of embodiments 55-82, wherein the resulting cryoprecipitate of step c) comprises at least 150 mg of fibrinogen per unit of cryoprecipitate.

Embodiment 84

The method of any one of embodiments 55-82, wherein the resulting cryoprecipitate of step c) comprises at least 750 mg of fibrinogen.

Embodiment 85

The method of any one of embodiments 55-82, wherein the resulting cryoprecipitate of step c) comprises at least 1500 mg of fibrinogen.

Embodiment 86

The method of any one of embodiments 55-85, wherein the cryoprecipitate of step a) further comprises plasma of a volume between about 5 mL and about 20 mL per unit of cryoprecipitate.

Embodiment 87

The method of any one of embodiments 61, 62, 75, 76, and 79-86, wherein the cryoprecipitate of step a) further comprises plasma of a volume greater than about 1 mL and less than or equal to about 75 mL.

Embodiment 88

The method of any one of embodiments 61, 62, 75, 76, and 79-86, wherein the cryoprecipitate of step a) further comprises plasma of a volume between about 40 mL and about 75 mL.

Embodiment 89

The method of any one of embodiments 61, 62, 75, 76, and 79-86, wherein the cryoprecipitate of step a) further comprises plasma of a volume between about 50 mL and about 60 mL.

Embodiment 90

The method of any one of embodiments 63, 64, and 75-86, wherein the cryoprecipitate of step a) further comprises plasma of a volume between about 30 mL and about 120 mL.

Embodiment 91

The method of any one of embodiments 55-90, wherein the plasma has been pathogen-inactivated by photochemical inactivation.

Embodiment 92

The method of embodiment 91, wherein the cryoprecipitate has been pathogen-inactivated by photochemical inactivation with a psoralen.

Embodiment 93

The method of embodiment 92, wherein the psoralen is amotosalen.

Embodiment 94

The method of any one of embodiments 55-93, wherein the cryoprecipitate is prepared from plasma that has been pathogen-inactivated in a first container suitable for photochemical inactivation of the plasma under sterile conditions;
  wherein the first container is coupled to a compound absorption device (CAD) such that the pathogen-inactivated plasma can be transferred from the first container to the CAD under sterile conditions; and
  wherein the cryoprecipitate is frozen and thawed in steps b) and c) within one or more second containers, each of which is coupled to the CAD such that the pathogen-inactivated plasma can be transferred from the CAD to the one or more second containers under sterile conditions, and each of which is suitable for freezing the pathogen-inactivated plasma followed by thawing of the pathogen-inactivated plasma under conditions that provide for the formation of the cryoprecipitate.

Embodiment 95

The method of embodiment 94, wherein each of the one or more second containers is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the one or more second containers.

Embodiment 96

The method of embodiment 94 or embodiment 95, wherein the cryoprecipitate is prepared from plasma that has been pathogen-inactivated in a first container suitable for photochemical inactivation of the plasma under sterile conditions;
  wherein the first container is coupled to a compound absorption device (CAD) such that the pathogen-inactivated plasma can be transferred from the first container to the CAD under sterile conditions; and
  wherein the cryoprecipitate is frozen and thawed in steps b) and c) within a third container configured to be coupled to one or more second containers, such that the pathogen-inactivated plasma can be transferred from the CAD to the one or more second containers under sterile conditions, wherein the third container is suitable for freezing the pathogen-inactivated plasma followed by thawing of the pathogen-inactivated plasma under conditions that provide for the formation of the cryoprecipitate.

Embodiment 97

The method of embodiment 96, wherein the third container is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the third container.

Embodiment 98

The method of any one of embodiments 55-97, wherein the subject is a human.

Embodiment 99

A kit comprising:
a) a container;
b) a pathogen-inactivated cryoprecipitate; and
c) instructions for using the pathogen-inactivated cryoprecipitate in an infusion into a subject, wherein the instructions indicate that the cryoprecipitate is suitable for infusion into the subject for up to about 5 days after thawing.

Embodiment 100

A kit comprising:
a) a container;
b) a pathogen-inactivated cryoprecipitate; and
c) a label indicating that the pathogen-inactivated cryoprecipitate is suitable for use for up to about 5 days after thawing.

Embodiment 101

A method of infusing a cryoprecipitate into a subject, comprising infusing into the subject the composition of any one of embodiments 1-54.

Embodiment 102

A method of infusing a cryoprecipitate into a subject, comprising infusing into the subject a cryoprecipitate produced by the method of any one of embodiments 55-98.

Embodiment 104

A cryoprecipitate produced by the method of any one of embodiments 55-98.

Embodiment 105

A method of preparing a pooled cryosupernatant for infusion into a subject comprising:
a) freezing at least a first pathogen-inactivated plasma and a second pathogen-inactivated plasma, wherein the first and the second pathogen-inactivated plasmas each have a volume of at least about 550 mL and less than about 650 mL;
b) thawing the first pathogen-inactivated plasma under conditions that provide for the formation of a first precipitate and a first supernatant, and thawing the second pathogen-inactivated plasma under conditions that provide for the formation of a second precipitate and a second supernatant;

c) separating the first and the second supernatants from the first and the second precipitates to form a first crosupernatant and a second cryosupernatant; and d) combining the first and the second cryosupernatants to form a pooled cryosupernatant.

Embodiment 106

The method of embodiment 105, wherein the first and the second pathogen-inactivated plasmas each have a volume of about 600 mL.

Embodiment 107

The method of embodiment 105 or embodiment 106, wherein step a) further comprises freezing at least a third pathogen-inactivated plasma and a fourth pathogen-inactivated plasma, wherein the third and the fourth pathogen-inactivated plasmas each have a volume of at least about 550 mL and less than 650 mL;

wherein step b) further comprises thawing the third pathogen-inactivated plasma under conditions that provide for the formation of a third precipitate and a third supernatant, and thawing the fourth pathogen-inactivated plasma under conditions that provide for the formation of a fourth precipitate and a fourth supernatant;

wherein step c) further comprises separating the third and the fourth supernatants from the third and the fourth precipitates to form a third cryosupernatant and a fourth cryosupernatant;

wherein the pooled cryosupernatant formed in step d) is a first pooled supernatant, and step d) further comprises combining the third and the fourth cryosupernatants to form a second pooled cryosupernatant;

and wherein the method further comprises:

e) combining the first pooled cryosupernatant and the second pooled cryosupernatant.

Embodiment 108

The method of embodiment 107, wherein the third and the fourth pathogen-inactivated plasmas each have a volume of about 600 mL.

Embodiment 109

The method of any one of embodiments 105-108, wherein the first and/or the second pathogen-inactivated plasma have been pathogen-inactivated by photochemical inactivation.

Embodiment 110

The method of embodiment 109, wherein the one or more of the first, second, third, and fourth pathogen-inactivated plasmas have been pathogen-inactivated with a psoralen.

Embodiment 111

The method of embodiment 110, wherein the psoralen is amotosalen.

Embodiment 112

The method of any one of embodiments 109-111, wherein one or more of the first, second, third, and fourth pathogen-inactivated plasmas have been pathogen-inactivated in a first container suitable for photochemical inactivation of plasma under sterile conditions, wherein the first container is coupled to a compound absorption device (CAD) such that the pathogen-inactivated plasma can be transferred from the first container to the CAD under sterile conditions.

Embodiment 113

The method of embodiment 112, wherein one or more of the first, second, third, and fourth pathogen-inactivated plasmas is frozen in step a) and thawed in step b) within one or more second containers, each of which is coupled to the CAD such that the pathogen-inactivated plasma can be transferred from the CAD to the one or more second containers under sterile conditions, and each of which is suitable for freezing the pathogen-inactivated plasma followed by thawing of the pathogen-inactivated plasma under conditions that provide for the formation of the cryoprecipitate.

Embodiment 114

The method of embodiment 113, wherein one or more of the first, second, third, and fourth pathogen-inactivated plasmas is frozen in step a) and thawed in step b) within a third container configured to be coupled to the one or more second containers, such that the pathogen-inactivated plasma can be transferred from the CAD to the one or more second containers to the third container under sterile conditions, wherein the third container is suitable for freezing the pathogen-inactivated plasma followed by thawing of the pathogen-inactivated plasma under conditions that provide for the formation of the cryoprecipitate.

Embodiment 115

The method of embodiment 114, wherein one or more of the first, second, third, and fourth supernatants is separated from one or more of the first, second, third, and fourth precipitates in step c) within one or more fourth containers, each of which is configured to be coupled to the one or more second containers or to the third container such that the supernatant can be transferred from the one or more second containers or the third container to the one or more fourth containers under sterile conditions to afford a pathogen-inactivated cryosupernatant contained within the one or more fourth containers and a pathogen-inactivated cryoprecipitate contained within the one or more second containers or the third container.

Embodiment 116

A method of infusing a cryosupernatant into a subject, comprising infusing into the subject a cryosupernatant produced by the method of any one of embodiments 105-115.

Embodiment 117

A processing set for preparing a pathogen-inactivated cryoprecipitate, comprising a) a first container within which one or more units of a plasma can be photochemically inactivated in the presence of a psoralen under sterile conditions;

b) a compound absorption device (CAD) coupled to the first container such that the one or more units of plasma can be transferred from the first container to the compound absorption device under sterile conditions; and
c) one or more second containers, each of which is coupled to the compound absorption device such that the one or more units of plasma can be transferred from the compound absorption device to the one or more second containers under sterile conditions to provide pathogen-inactivated plasma suitable for infusion into a subject, wherein the one or more second containers is suitable for freezing the pathogen-inactivated plasma followed by thawing of the pathogen-inactivated plasma under conditions that provide for the formation of a precipitate and a supernatant.

Embodiment 118

The processing set of embodiment 117, wherein each of the one or more second containers is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the one or more second containers.

Embodiment 119

A processing set for preparing a pathogen-inactivated cryoprecipitate, comprising
a) a first container within which one or more units of a plasma can be photochemically inactivated in the presence of a psoralen under sterile conditions;
b) a compound absorption device (CAD) coupled to the first container such that the one or more units of plasma can be transferred from the first container to the compound absorption device under sterile conditions;
c) one or more second containers, each of which is coupled to the compound absorption device such that the one or more units of plasma can be transferred from the compound absorption device to the one or more second containers under sterile conditions to provide pathogen-inactivated plasma suitable for infusion into a subject; and
d) a third container, which is configured to be coupled to the one or more second containers such that the pathogen-inactivated plasma can be transferred from the one or more second containers to the third container under sterile conditions, wherein the third container is suitable for freezing the pathogen-inactivated plasma followed by thawing of the pathogen-inactivated plasma under conditions that provide for the formation of a precipitate and a supernatant.

Embodiment 120

The processing set of embodiment 119, wherein the third container is suitable for freezing the pathogen-inactivated plasma, followed by thawing of the pathogen-inactivated plasma under conditions that provide for the formation of the cryoprecipitate and a cryosupernatant, followed by removal of all or a portion of the cryosupernatant from the third container.

Embodiment 121

The processing set of any one of embodiments 117-120, further comprising an additional container suitable for mixing the one or more units of plasma with a pathogen inactivation compound, wherein the additional container is coupled to the first container such that the one or more units of plasma in admixture with the pathogen-inactivating compound can be transferred from the additional container to the first container under sterile conditions.

Embodiment 122

The processing set of any one of embodiments 117-121, further comprising:
one or more fourth containers, each of which is configured to be coupled to the one or more second containers or to the third container such that the supernatant can be transferred from the one or more second containers or the third container to the one or more fourth containers under sterile conditions to provide a pathogen-inactivated cryosupernatant contained within the one or more fourth containers and a pathogen-inactivated cryoprecipitate contained within the one or more second containers or the third container.

Embodiment 123

The processing set of any one of embodiments 119-122, wherein the third container is coupled to the one or more second containers such that the supernatant can be transferred from the one or more second containers to the third container under sterile conditions to afford a pathogen-inactivated cryosupernatant contained within the third container and a pathogen-inactivated cryoprecipitate contained within the one or more second containers.

Embodiment 124

The processing set of embodiment 122 or embodiment 123, wherein the third container is configured to be coupled to the one or more second containers such that the pathogen-inactivated plasma can be transferred from the one or more second containers to the third container under sterile conditions;
wherein the third container is suitable for freezing the pathogen-inactivated plasma followed by thawing of the pathogen-inactivated plasma under conditions that provide for the formation of a precipitate and a supernatant; and
wherein each of the one or more fourth containers is configured to be coupled to the third container such that the supernatant can be transferred from the third container to the one or more fourth containers under sterile conditions to afford a pathogen-inactivated cryosupernatant contained within the one or more fourth containers and a pathogen-inactivated cryoprecipitate contained within the third container.

Embodiment 125

A method of preparing a cryoprecipitate for infusion into a subject comprising:
a) preparing a cryoprecipitate from pathogen-inactivated plasma; and
b) freezing the cryoprecipitate;
wherein the cryoprecipitate is suitable for infusion into the subject for up to about 5 days after thawing.

Embodiment 126

The method of embodiment 125, wherein the cryoprecipitate is prepared from at least about 550 mL and less than about 650 mL of pathogen-inactivated plasma.

Embodiment 127

The method of embodiment 126, wherein the cryoprecipitate is prepared from about 600 mL of pathogen-inactivated plasma.

Embodiment 128

The method of embodiment 125, further comprising combining a first cryoprecipitate prepared from at least about 550 mL and less than about 650 mL of pathogen-inactivated plasma and a second cryoprecipitate prepared from at least about 550 mL and less than about 650 mL of pathogen-inactivated plasma, wherein the first and the second cryoprecipitates are combined prior to step b).

Embodiment 129

The method of embodiment 128, wherein the first cryoprecipitate is prepared from about 600 mL of pathogen-inactivated plasma, and wherein the second cryoprecipitate is prepared from about 600 mL of pathogen-inactivated plasma.

Embodiment 130

The method of embodiment 125, further comprising combining a first cryprecipitate prepared from 3 units of pathogen-inactivated plasma and a second cryoprecipitate prepared from 3 units of pathogen-inactivated plasma, wherein the first and the second cryoprecipitates are combined prior to step b).

Embodiment 131

A method of preparing a cryoprecipitate for infusion into a subject comprising:
  a) preparing a cryoprecipitate from plasma; and
  b) subjecting the cryoprecipitate to pathogen inactivation;
  wherein the pathogen-inactivated cryoprecipitate is suitable for infusion into the subject for up to about 5 days after storage at between about 2° C. and about 25° C.

Embodiment 132

The method of embodiment 126, further comprising, after step b):
  c) freezing the pathogen-inactivated cryoprecipitate; and
  d) thawing the frozen pathogen-inactivated cryoprecipitate;
  wherein the pathogen-inactivated cryoprecipitate is suitable for infusion into the subject for up to about 3 days after thawing.

Embodiment 133

The method of embodiment 132, wherein the pathogen-inactivated cryoprecipitate is suitable for infusion into the subject for up to about 5 days after thawing.

Embodiment 134

The method of any one of embodiments 131-133, wherein the cryoprecipitate is prepared from 1 unit of plasma.

Embodiment 135

The method of embodiment 134, wherein the cryoprecipitate is prepared from at least about 180 mL and less than about 250 mL of plasma.

Embodiment 136

The method of embodiment 135, wherein the prepared cryoprecipitate is resuspended in at least about 30 mL and less than about 70 mL of plasma.

Embodiment 137

The method of any one of embodiments 131-133, further comprising combining at least a first cryoprecipitate prepared from 1 unit of plasma and a second cryoprecipitate prepared from 1 unit of plasma, wherein the first and the second cryoprecipitates are combined prior to step b).

Embodiment 138

The method of any one of embodiments 131-133, further comprising combining at least a first cryoprecipitate prepared from 1 unit of plasma and a second cryoprecipitate prepared from 1 unit of plasma, wherein the first and the second cryoprecipitates are combined after step b).

Embodiment 139

The method of embodiment 137 or embodiment 138, wherein the first cryoprecipitate is prepared from at least about 180 mL and less than about 250 mL of plasma, and wherein the second cryoprecipitate is prepared from at least about 180 mL and less than about 250 mL of plasma.

Embodiment 140

The method of any one of embodiments 137-139, wherein combining at least a first cryoprecipitate and a second cryoprecipitate comprises combining 2-12 cryoprecipitates.

Embodiment 141

The method of any one of embodiments 137-140, wherein the volume of the combined cryoprecipitates is at least about 500 mL and less than about 700 mL.

Embodiment 142

The method of any one of embodiments 137-140, wherein the first and the second cryoprecipitates are prepared from plasma of the same ABO type.

Embodiment 143

The method of any one of embodiments 137-140, wherein the first and the second cryoprecipitates are prepared from plasma of different ABO types.

Embodiment 144

The method of any one of claims 137-140, wherein the combined cryopreciptiates are prepared from at least 3

Embodiment 145

The method of any one of embodiments 134-144, wherein the cryoprecipitate is prepared from whole-blood derived plasma.

Embodiment 146

The method of any one of embodiments 131-133, 136-138, and 140-143, wherein the cryoprecipitate is prepared from apheresis collected plasma.

Embodiment 147

The method of embodiment 146, wherein the apheresis collected plasma is between about 200 mL and about 800 mL.

What is claimed is:

1. A method of preparing a cryoprecipitate for infusion into a subject up to about 5 days after thawing the cryoprecipitate, the method comprising:
   a) preparing a cryoprecipitate from pathogen-inactivated plasma, wherein the plasma has been pathogen-inactivated by photochemical inactivation, and wherein the method comprises combining a first cryoprecipitate prepared from at least about 550 mL and less than about 650 mL of pathogen-inactivated plasma and a second cryoprecipitate prepared from at least about 550 mL and less than about 650 mL of pathogen-inactivated plasma;
   b) freezing the combined cryoprecipitate; and
   c) thawing the frozen, combined cryoprecipitate;
   wherein the cryoprecipitate for infusion comprises at least 750 mg of fibrinogen when tested at least 3 days and within 5 days after thawing; and
   wherein the method does not comprise determining a level of factor VIII in the thawed cryoprecipitate, either by determining the level of factor VIII in the thawed cryoprecipitate itself or by determining the level of factor VIII in one or more cryoprecipitate sample(s) held to be representative of the thawed cryoprecipitate.

2. The method of claim 1, wherein the cryoprecipitate comprises at least 1500 mg of fibrinogen when tested at least 3 days and within 5 days after thawing.

3. The method of claim 1, wherein the cryoprecipitate further comprises plasma of a volume from about 30 mL to about 150 mL.

4. The method of claim 1, wherein the first cryoprecipitate further comprises plasma of a volume from about 30 mL to about 150 mL and wherein the second cryoprecipitate comprises plasma of a volume from about 30 mL to about 150 mL.

5. The method of claim 1, wherein the cryoprecipitate is prepared from plasma obtained from 2-6 donors.

6. The method of claim 1, wherein the plasma has been pathogen-inactivated by photochemical inactivation with a psoralen.

7. The method of claim 1, wherein the plasma has been pathogen-inactivated by photochemical inactivation with amotosalen.

8. The method of claim 1, wherein a) further comprises preparing a third cryoprecipitate from at least about 550 mL and less than about 650 mL of pathogen-inactivated plasma and combining the first, second, and third cryoprecipitates.

9. The method of claim 1, wherein the pathogen inactivated plasma is prepared from whole-blood derived plasma.

10. The method of claim 1, wherein the pathogen inactivated plasma is prepared from apheresis collected plasma.

11. The method of claim 1, wherein the cryoprecipitate is prepared from plasma frozen within 24 hours of donation.

12. The method of claim 1, further comprising storing the thawed cryoprecipitate at room temperature.

13. The method of claim 1, further comprising storing the thawed cryoprecipitate at between 2° C. and 25° C.

14. The method of claim 1, further comprising storing the thawed cryoprecipitate at between 20° C. and 24° C.

15. The method of claim 1, further comprising testing the thawed combined cryoprecipitate for fibrinogen to determine a level of fibrinogen in the thawed combined cryoprecipitate.

16. The method of claim 1, further comprising:
   d) preparing a thawed, combined cryoprecipitate for testing according to steps a), b), and c) of claim 1; and
   e) determining a level of fibrinogen in the thawed, combined cryoprecipitate for testing, wherein the thawed, combined cryoprecipitate for testing is held to be representative of the thawed, combined cryoprecipitate for infusion.

17. The method of claim 1, further comprising:
   d) preparing two or more additional thawed, combined cryoprecipitates for testing according to steps a), b), and c) of claim 1; and
   e) determining an average measurement of fibrinogen in the two or more additional thawed, combined cryoprecipitates for testing, wherein the average measurement of the two or more additional thawed, combined cryoprecipitates for testing is held to be representative of the thawed, combined cryoprecipitate for infusion.

18. The method of claim 1, wherein the cryoprecipitate is prepared from plasma that has been pathogen-inactivated in a first container suitable for photochemical inactivation of the plasma under sterile conditions;
   wherein the first container is coupled to a compound absorption device (CAD) such that the pathogen-inactivated plasma can be transferred from the first container to the CAD under sterile conditions;
   wherein the CAD is coupled to one or more second containers, each of which is coupled to the CAD such that the pathogen-inactivated plasma can be transferred from the CAD to the one or more second containers under sterile conditions; and
   wherein the cryoprecipitate is contained within a third container configured to be coupled to one or more second containers, such that the pathogen-inactivated plasma can be transferred from the CAD to the one or more second containers to the third container under sterile conditions, wherein the third container is suitable for freezing the pathogen-inactivated plasma followed by thawing of the pathogen-inactivated plasma under conditions that provide for the formation of the cryoprecipitate.

19. A method of preparing a cryoprecipitate for infusion into a subject up to about 5 days after thawing the cryoprecipitate, the method comprising:
   a) preparing a cryoprecipitate from plasma; and
   b) subjecting the cryoprecipitate to pathogen inactivation, wherein the cryoprecipitate has been pathogen-inactivated by photochemical inactivation;
   wherein the pathogen-inactivated cryoprecipitate comprises at least 750 mg of fibrinogen when tested at least 3 days and within 5 days after thawing.

20. The method of claim 19, further comprising, after step b):

c) freezing the pathogen-inactivated cryoprecipitate; and
d) thawing the frozen pathogen-inactivated cryoprecipitate;
wherein the pathogen-inactivated cryoprecipitate comprises at least 750 mg of fibrinogen when tested at least 3 days and within 5 days after thawing.

21. The method of claim 19, wherein the cryoprecipitate comprises at least 1500 mg of fibrinogen when tested at least 3 days and within 5 days after thawing.

22. The method of claim 18, wherein preparing the cryoprecipitate further comprises, prior to freezing the combined cryoprecipitate:

(1) separating the cryoprecipitate from a cryosupernatant; and
(2) resuspending the cryoprecipitate in a volume of the cryosupernatant.

* * * * *